US011369701B2

(12) United States Patent
Nakata et al.

(10) Patent No.: US 11,369,701 B2
(45) Date of Patent: Jun. 28, 2022

(54) RI-LABELED HUMANIZED ANTIBODY

(71) Applicants: NIHON MEDI-PHYSICS CO., LTD., Tokyo (JP); SUMITOMO PHARMA CO., LTD., Osaka (JP)

(72) Inventors: Norihito Nakata, Tokyo (JP); Nobuya Kobashi, Tokyo (JP); Yoshinari Shoyama, Tokyo (JP); Mitsuhiro Matono, Osaka (JP); Yasushi Ochiai, Tokyo (JP); Takayuki Murakami, Mie (JP)

(73) Assignees: NIHON MEDI-PHYSICS CO., LTD., Tokyo (JP); SUMITOMO PHARMA CO., LTD., Osaka (JP)

( * ) Notice: Subject to any disclaimer, the term of this patent is extended or adjusted under 35 U.S.C. 154(b) by 0 days.

(21) Appl. No.: 17/367,077

(22) Filed: Jul. 2, 2021

(65) Prior Publication Data
US 2021/0338852 A1 Nov. 4, 2021

Related U.S. Application Data

(63) Continuation of application No. PCT/JP2020/039074, filed on Oct. 16, 2020.

(30) Foreign Application Priority Data

Oct. 18, 2019 (JP) .............................. JP2019-191562

(51) Int. Cl.
| C07K 16/22 | (2006.01) |
| A61K 51/10 | (2006.01) |
| A61K 51/04 | (2006.01) |
| C07K 16/30 | (2006.01) |

(52) U.S. Cl.
CPC ...... *A61K 51/1045* (2013.01); *A61K 51/0482* (2013.01); *C07K 16/3092* (2013.01); *C07K 2317/24* (2013.01)

(58) Field of Classification Search
None
See application file for complete search history.

(56) References Cited

U.S. PATENT DOCUMENTS

| 9,629,926 B2 * | 4/2017 | Govindan ............ A61K 38/395 |
| 2016/0303258 A1 | 10/2016 | Cvet et al. |
| 2020/0181196 A1 | 6/2020 | Ito et al. |
| 2021/0170058 A1 | 6/2021 | Komoto et al. |

FOREIGN PATENT DOCUMENTS

| JP | 1995-07-203974 | 8/1995 |
| JP | 1999-11-5749 | 1/1999 |
| JP | 2017-503763 A | 2/2017 |
| WO | WO 2013/157102 A1 | 10/2013 |
| WO | WO2013/157105 A1 | 10/2013 |
| WO | WO 2017/217347 A1 | 12/2017 |
| WO | WO 2019/203191 A1 | 10/2019 |

OTHER PUBLICATIONS

Almagro & Fransson, Frontiers in Bioscience 2008; 13:1619-33 (Year: 2008).*
De Genst et al., Dev Comp Immunol 2006; 30:187-98 (Year: 2006).*
Yoshinaga et al., J. Biochem 2008; 143:593-601 (Year: 2008).*
Akimasa Inui, et al; Radioimmunotherapy for Pancreatic Carcinoma Using 1311-Labeled Monoclonal Antibody Nd2 in Xenografted Nude Mice; Japanese Journal of Cancer Research, 87, 977-984, 1996.
Japanese Journal of Clinical Medicine vol. 64 extra issue 1, 2006, p. 274-278.
Tetsuji Sawada, et al; Preoperative Clinical Radioimmunodetection of Pancreatic Cancer by $^{111}$In-labeled Chimeric Monoclonal Antibody Nd2; Japanese Journal of Cancer Research, 90, 1179-1186, 1999.
International Search Report issued in PCT/JP2020/039074, dated Jan. 12, 2021, citing references AQ, AS, AT and AU therein.

* cited by examiner

*Primary Examiner* — Meera Natarajan
(74) *Attorney, Agent, or Firm* — Oblon, McClelland, Maier & Neustadt, L.L.P.

(57) ABSTRACT

The RI-labeled anti-MUC5AC humanized antibody of the present invention is a conjugate of a chelating agent chelated with a radionuclide and an antibody (the radionuclide is a metal nuclide that emits α particle or positron, and the antibody is a humanized antibody specifically binding to MUC5AC), and is superior in specificity for MUC5AC and accumulation in tumor. Therefore, it is extremely useful for the treatment and/or diagnosis of diseases in which MUC5AC is overexpressed, particularly cancer.

18 Claims, 31 Drawing Sheets

Specification includes a Sequence Listing.

◆ :mean, error bar: standard deviation
● :plotted results of each individual

◆ :mean, error bar: standard deviation
● :plotted results of each individual

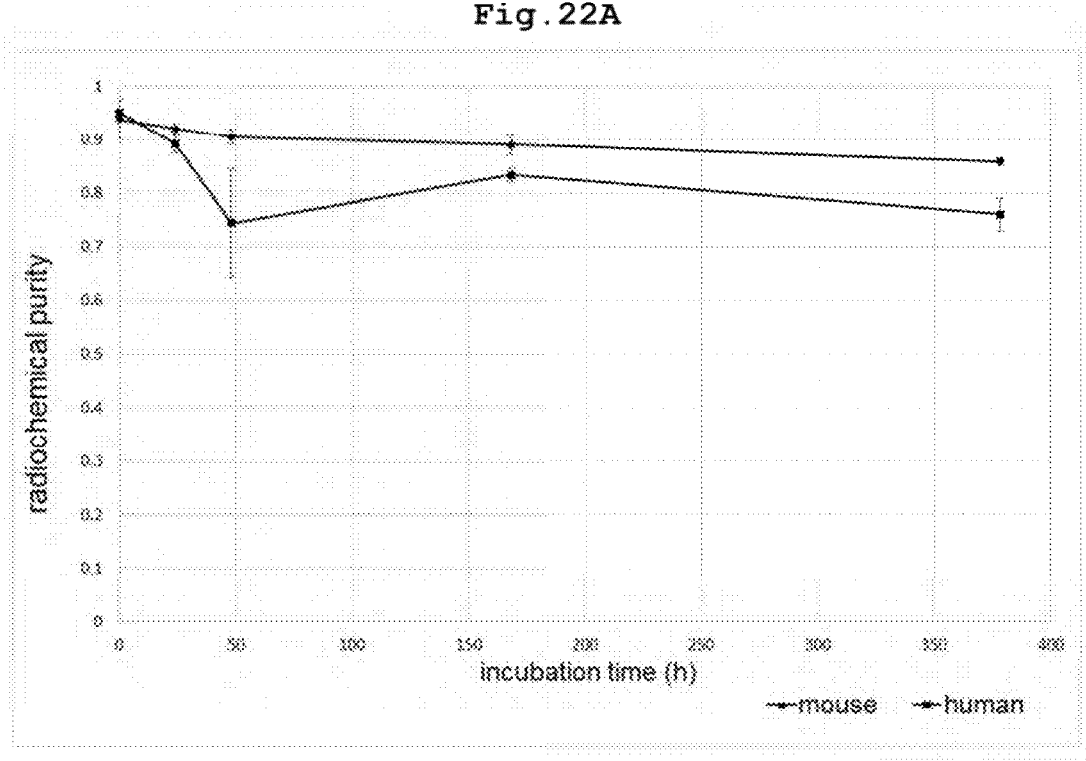
Fig.22A
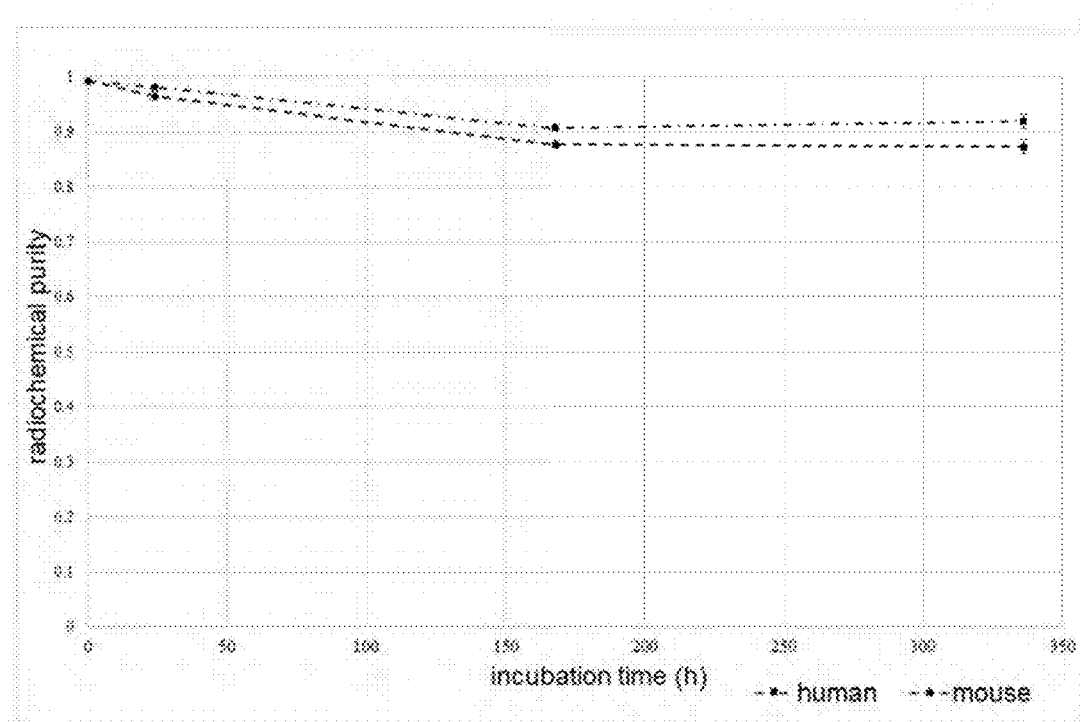

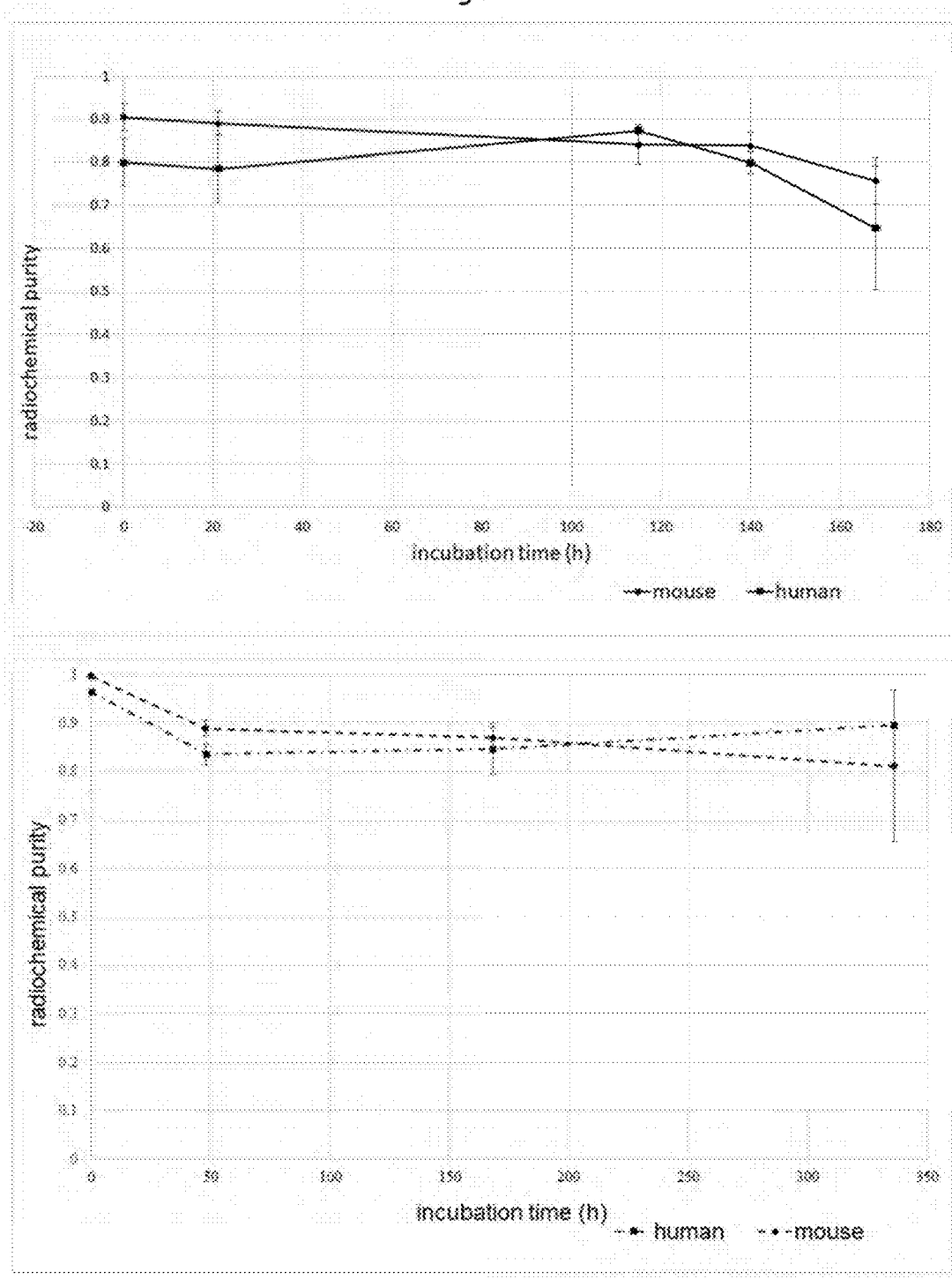

$^{225}$Ac-labeled anti-MUC5AC humanized antibody (DBCO-DOTAGA)

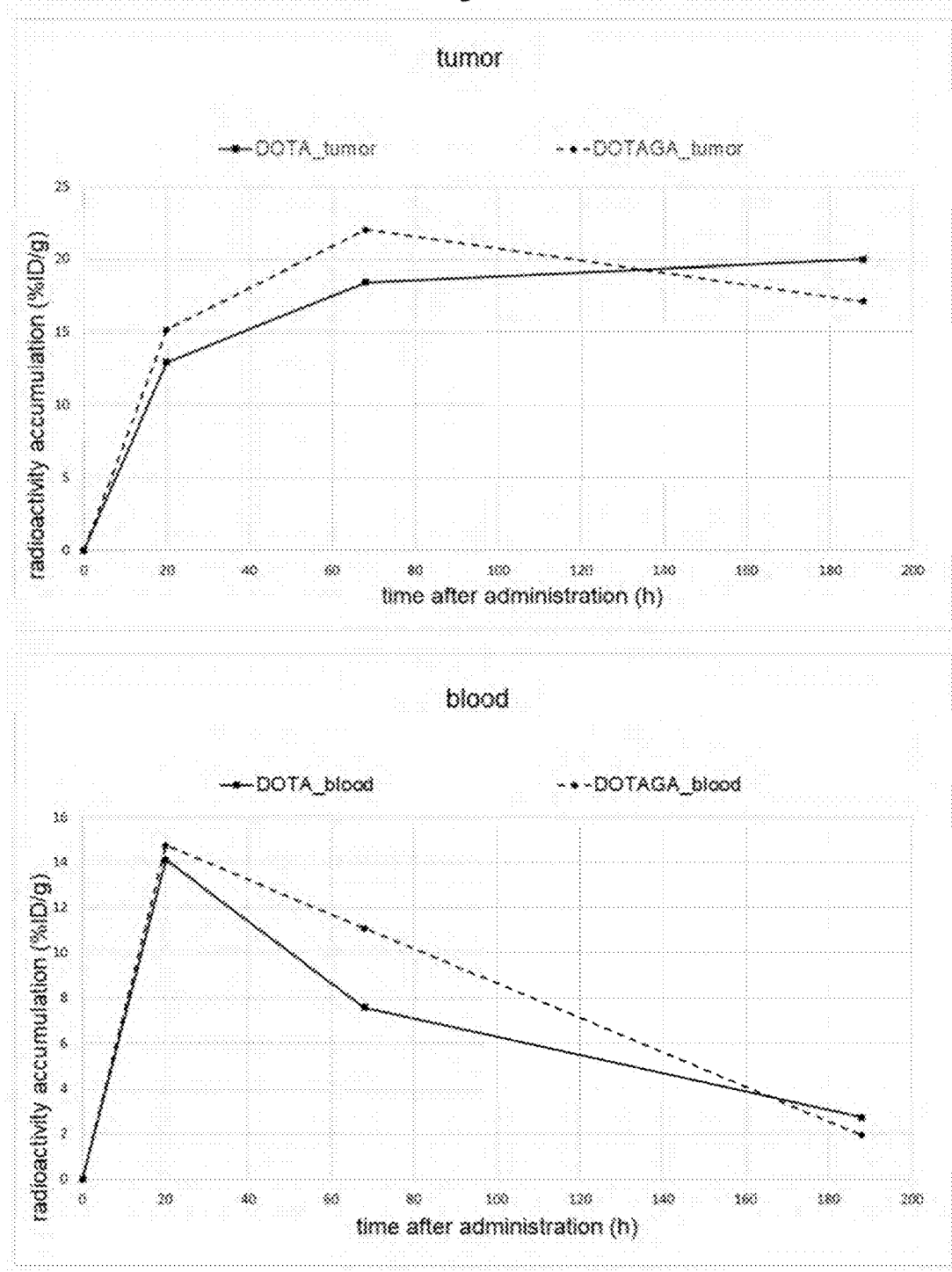

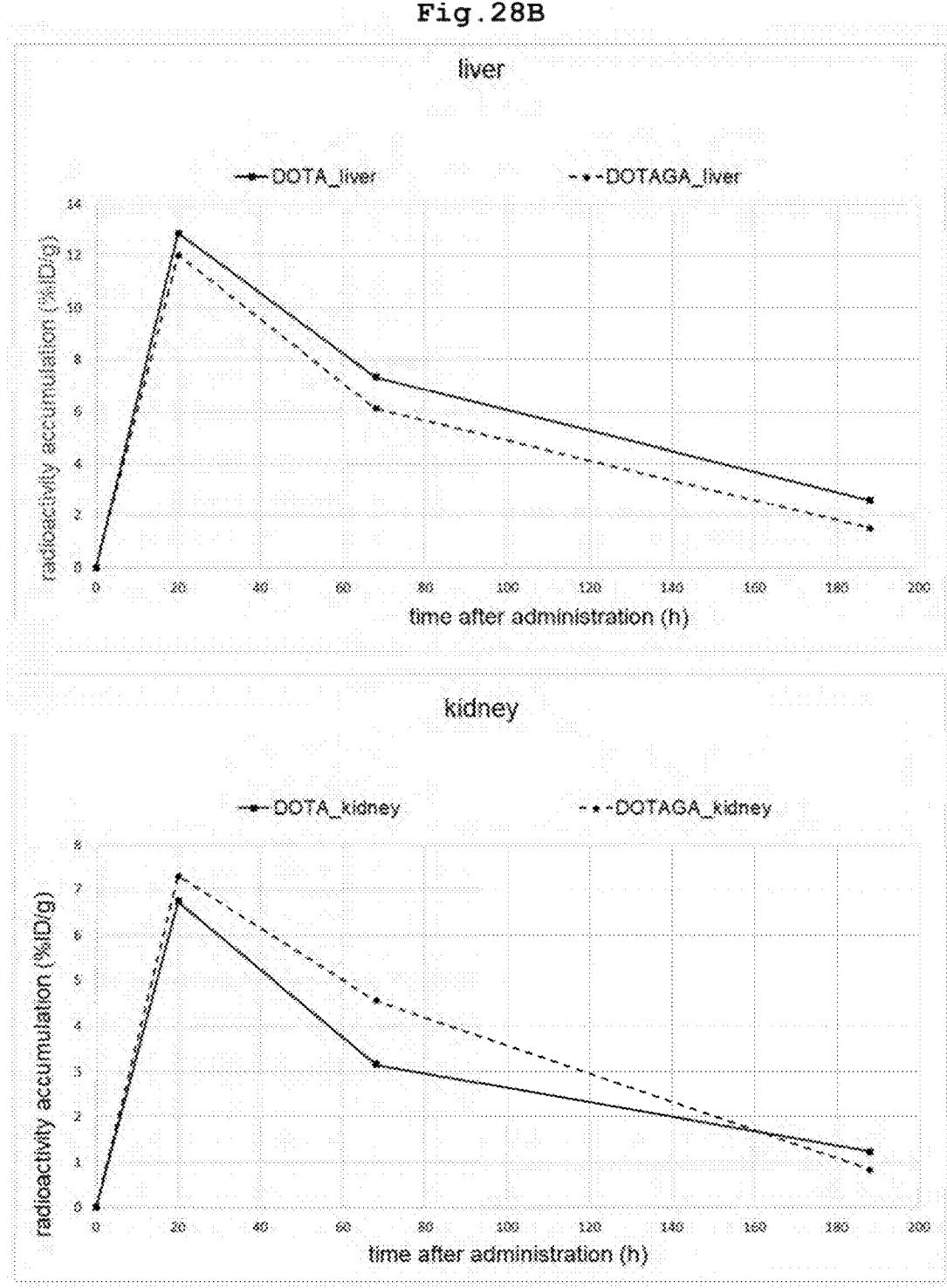

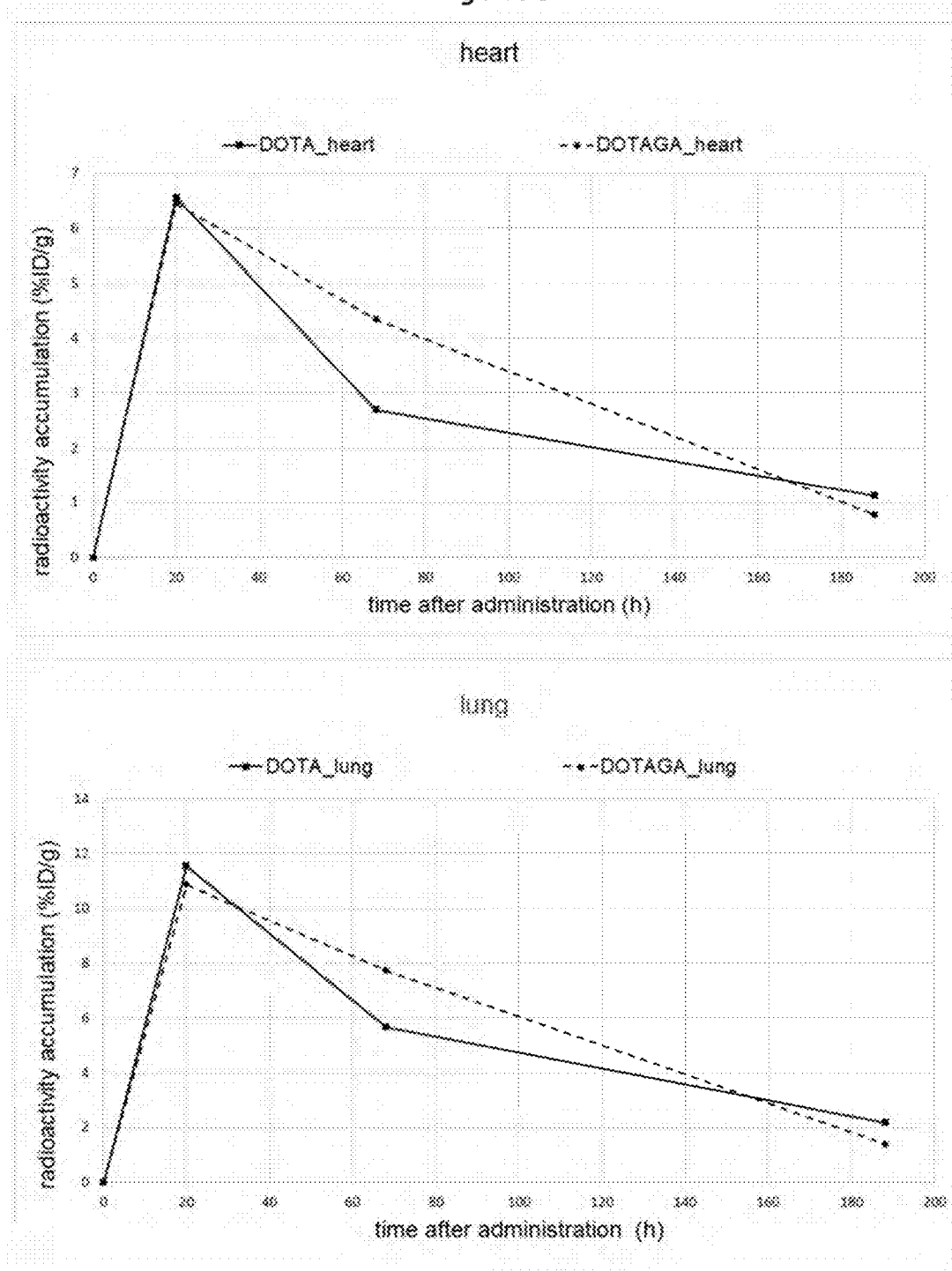

SEQUENCE LISTING

```
<160> NUMBER OF SEQ ID NOS: 26

<210> SEQ ID NO 1
<211> LENGTH: 121
<212> TYPE: PRT
<213> ORGANISM: Artificial Sequence
<220> FEATURE:
<223> OTHER INFORMATION: Humanized antibody heavy chain variable region
      1 (H01)

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ser Thr Ile Ser Asn Ser Gly Arg Tyr Thr Tyr Phe Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
```

```
                    85                  90                  95
Thr Arg His Leu Asp Tyr Ala Asn Tyr Asp Ala Met Asp Tyr Trp Gly
                100                 105                 110

Gln Gly Thr Leu Val Thr Val Ser Ser
            115                 120

<210> SEQ ID NO 2
<211> LENGTH: 121
<212> TYPE: PRT
<213> ORGANISM: Artificial Sequence
<220> FEATURE:
<223> OTHER INFORMATION: Humanized antibody heavy chain variable region
      2 (H02)

<400> SEQUENCE: 2

Leu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Ser Asn Tyr
                20                  25                  30

Gly Met Ser Trp Ile Arg Gln Ala Pro Gly Lys Gly Leu Glu Trp Val
            35                  40                  45

Ser Thr Ile Ser Asn Ser Gly Arg Tyr Thr Tyr Phe Pro Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Thr Arg His Leu Asp Tyr Ala Asn Tyr Asp Ala Met Asp Tyr Trp Gly
                100                 105                 110

Gln Gly Thr Leu Val Thr Val Ser Ser
            115                 120

<210> SEQ ID NO 3
<211> LENGTH: 121
<212> TYPE: PRT
<213> ORGANISM: Artificial Sequence
<220> FEATURE:
<223> OTHER INFORMATION: Humanized antibody heavy chain variable region
      3 (H03)

<400> SEQUENCE: 3

Leu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
                20                  25                  30

Gly Met Ser Trp Val Arg Gln Ala Pro Gly Lys Gly Leu Glu Trp Val
            35                  40                  45

Ala Thr Ile Ser Asn Ser Gly Arg Tyr Thr Tyr Phe Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Thr Arg His Leu Asp Tyr Ala Asn Tyr Asp Ala Met Asp Tyr Trp Gly
                100                 105                 110

Gln Gly Thr Leu Val Thr Val Ser Ser
            115                 120
```

```
<210> SEQ ID NO 4
<211> LENGTH: 121
<212> TYPE: PRT
<213> ORGANISM: Artificial Sequence
<220> FEATURE:
<223> OTHER INFORMATION: Humanized antibody heavy chain variable region
      4 (H04)

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ser Thr Ile Ser Asn Ser Gly Arg Tyr Thr Tyr Phe Pro Asp Ser Val
    50                  55                  60

Lys Gly Arg Phe Thr Ile Ser Arg Asp Asn Ser Arg Asn Thr Leu Tyr
65                  70                  75                  80

Leu Gln Met Asn Thr Leu Arg Ala Glu Asp Thr Ala Val Tyr Tyr Cys
                85                  90                  95

Thr Arg His Leu Asp Tyr Ala Asn Tyr Asp Ala Met Asp Tyr Trp Gly
            100                 105                 110

Gln Gly Thr Pro Val Thr Val Ser Ser
        115                 120

<210> SEQ ID NO 5
<211> LENGTH: 111
<212> TYPE: PRT
<213> ORGANISM: Artificial Sequence
<220> FEATURE:
<223> OTHER INFORMATION: Humanized antibody light chain variable region
      1 (L01)

<400> SEQUENCE: 5

Asp Ile Val Met Thr Gln Ser Pro Ser Ser Leu Ser Ala Ser Val Gly
1               5                   10                  15

Asp Arg Val Thr Ile Thr Cys Arg Ala Ser Lys Ser Val Thr Thr Ser
            20                  25                  30

Asp Phe Ser Tyr Met His Trp Tyr Gln Gln Lys Pro Gly Lys Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gly Gly Thr Lys Val Glu Ile Lys
            100                 105                 110

<210> SEQ ID NO 6
<211> LENGTH: 111
<212> TYPE: PRT
<213> ORGANISM: Artificial Sequence
<220> FEATURE:
<223> OTHER INFORMATION: Humanized antibody light chain variable region
      2 (L02)

<400> SEQUENCE: 6

Asp Val Val Met Thr Gln Ser Pro Ser Thr Leu Ser Ala Ser Val Gly
1               5                   10                  15
```

```
Asp Arg Val Thr Ile Thr Cys Arg Ala Ser Lys Ser Val Thr Thr Ser
            20                  25                  30

Asp Phe Ser Tyr Met His Trp Tyr Gln Gln Lys Pro Gly Gln Ala Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gln Gly Thr Lys Leu Glu Ile Lys
            100                 105                 110

<210> SEQ ID NO 7
<211> LENGTH: 111
<212> TYPE: PRT
<213> ORGANISM: Artificial Sequence
<220> FEATURE:
<223> OTHER INFORMATION: Humanized antibody light chain variable region
      3 (L03)

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Lys Ser Val Thr Thr Ser
            20                  25                  30

Asp Phe Ser Tyr Met His Trp Tyr Gln Gln Lys Pro Gly Lys Ser Pro
        35                  40                  45

Lys Leu Leu Ile Tyr Leu Ala Ser Asn Leu Glu Ser Gly Val Pro Ser
    50                  55                  60

Arg Phe Ser Gly Ser Gly Ser Gly Thr Asp Phe Ser Leu Thr Ile Ser
65                  70                  75                  80

Ser Leu Gln Pro Glu Asp Phe Ala Thr Tyr Tyr Cys Gln His Ser Arg
                85                  90                  95

Glu Phe Pro Trp Thr Phe Gly Gly Gly Thr Lys Val Glu Ile Lys
            100                 105                 110

<210> SEQ ID NO 8
<211> LENGTH: 111
<212> TYPE: PRT
<213> ORGANISM: Artificial Sequence
<220> FEATURE:
<223> OTHER INFORMATION: Humanized antibody light chain variable region
      4 (L04)

<400> SEQUENCE: 8

Asp Ile Val Met Thr Gln Ser Pro Asp Ser Leu Ala Val Ser Leu Gly
1               5                   10                  15

Glu Arg Ala Thr Ile Asn Cys Lys Ala Ser Lys Ser Val Thr Thr Ser
            20                  25                  30

Asp Phe Ser Tyr Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95
```

Glu Phe Pro Trp Thr Phe Gly Gly Gly Thr Lys Leu Glu Ile Lys
            100                 105                 110

<210> SEQ ID NO 9
<211> LENGTH: 13
<212> TYPE: PRT
<213> ORGANISM: Artificial
<220> FEATURE:
<223> OTHER INFORMATION: antibody-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
      acid, 2-amino suberic acid, or diaminopropionic acid

<400> SEQUENCE: 9

Asp Cys Ala Tyr His Xaa Gly Glu Leu Val Trp Cys Thr
1               5                   10

<210> SEQ ID NO 10
<211> LENGTH: 17
<212> TYPE: PRT
<213> ORGANISM: Artificial
<220> FEATURE:
<223> OTHER INFORMATION: antibody-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid

<400> SEQUENCE: 10

Gly Pro Asp Cys Ala Tyr His Xaa Gly Glu Leu Val Trp Cys Thr Phe
1               5                   10                  15

His

<210> SEQ ID NO 11
<211> LENGTH: 13
<212> TYPE: PRT
<213> ORGANISM: Artificial
<220> FEATURE:
<223> OTHER INFORMATION: antibody-binding peptide
<220> FEATURE:
<221> NAME/KEY: misc_feature
<222> LOCATION: (6)..(6)
<223> OTHER INFORMATION: Xaa is lysine, cystein, aspartic acid, glutamic
      acid, 2-amino suberic acid, or diaminopropionic acid

<400> SEQUENCE: 11

Arg Cys Ala Tyr His Xaa Gly Glu Leu Val Trp Cys Ser
1               5                   10

<210> SEQ ID NO 12
<211> LENGTH: 17
<212> TYPE: PRT
<213> ORGANISM: Artificial
<220> FEATURE:
<223> OTHER INFORMATION: antibody-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid

<400> SEQUENCE: 12

Gly Pro Arg Cys Ala Tyr His Xaa Gly Glu Leu Val Trp Cys Ser Phe
1               5                   10                  15

His

```
<210> SEQ ID NO 13
<211> LENGTH: 17
<212> TYPE: PRT
<213> ORGANISM: Artificial
<220> FEATURE:
<223> OTHER INFORMATION: antibody-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid

<400> SEQUENCE: 13

Ser Pro Asp Cys Ala Tyr His Xaa Gly Glu Leu Val Trp Cys Thr Phe
1               5                   10                  15

His

<210> SEQ ID NO 14
<211> LENGTH: 17
<212> TYPE: PRT
<213> ORGANISM: Artificial
<220> FEATURE:
<223> OTHER INFORMATION: antibody-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid

<400> SEQUENCE: 14

Gly Asp Asp Cys Ala Tyr His Xaa Gly Glu Leu Val Trp Cys Thr Phe
1               5                   10                  15

His

<210> SEQ ID NO 15
<211> LENGTH: 17
<212> TYPE: PRT
<213> ORGANISM: Artificial
<220> FEATURE:
<223> OTHER INFORMATION: antibody-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid

<400> SEQUENCE: 15

Gly Pro Ser Cys Ala Tyr His Xaa Gly Glu Leu Val Trp Cys Thr Phe
1               5                   10                  15

His

<210> SEQ ID NO 16
<211> LENGTH: 17
<212> TYPE: PRT
<213> ORGANISM: Artificial
<220> FEATURE:
<223> OTHER INFORMATION: antibody-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid

<400> SEQUENCE: 16

Gly Pro Asp Cys Ala Tyr His Xaa Gly Glu Leu Val Trp Cys Ser Phe
1               5                   10                  15
```

His

<210> SEQ ID NO 17
<211> LENGTH: 17
<212> TYPE: PRT
<213> ORGANISM: Artificial
<220> FEATURE:
<223> OTHER INFORMATION: antibody-binding peptide
<220> FEATURE:
<221> NAME/KEY: misc_feature
<222> LOCATION: (8)..(8)
<223> OTHER INFORMATION: Xaa is lysine, cystein, aspartic acid, glutamic acid, 2-amino suberic acid, or diaminopropionic acid

<400> SEQUENCE: 17

Gly Pro Asp Cys Ala Tyr His Xaa Gly Glu Leu Val Trp Cys Thr His
1               5                   10                  15

His

<210> SEQ ID NO 18
<211> LENGTH: 17
<212> TYPE: PRT
<213> ORGANISM: Artificial
<220> FEATURE:
<223> OTHER INFORMATION: antibody-binding peptide
<220> FEATURE:
<221> NAME/KEY: misc_feature
<222> LOCATION: (8)..(8)
<223> OTHER INFORMATION: Xaa is lysine, cystein, aspartic acid, glutamic acid, 2-amino suberic acid, or diaminopropionic acid

<400> SEQUENCE: 18

Gly Pro Asp Cys Ala Tyr His Xaa Gly Glu Leu Val Trp Cys Thr Phe
1               5                   10                  15

Tyr

<210> SEQ ID NO 19
<211> LENGTH: 17
<212> TYPE: PRT
<213> ORGANISM: Artificial
<220> FEATURE:
<223> OTHER INFORMATION: antibody-binding peptide
<220> FEATURE:
<221> NAME/KEY: misc_feature
<222> LOCATION: (8)..(8)
<223> OTHER INFORMATION: Xaa is lysine, cystein, aspartic acid, glutamic acid, 2-amino suberic acid, or diaminopropionic acid

<400> SEQUENCE: 19

Ser Pro Asp Cys Ala Tyr His Xaa Gly Glu Leu Val Trp Cys Thr Phe
1               5                   10                  15

Tyr

<210> SEQ ID NO 20
<211> LENGTH: 17
<212> TYPE: PRT
<213> ORGANISM: Artificial
<220> FEATURE:
<223> OTHER INFORMATION: antibody-binding peptide
<220> FEATURE:
<221> NAME/KEY: misc_feature
<222> LOCATION: (8)..(8)
<223> OTHER INFORMATION: Xaa is lysine, cystein, aspartic acid, glutamic acid, 2-amino suberic acid, or diaminopropionic acid

<400> SEQUENCE: 20

Ser Asp Asp Cys Ala Tyr His Xaa Gly Glu Leu Val Trp Cys Thr Phe
1               5                   10                  15

Tyr

<210> SEQ ID NO 21
<211> LENGTH: 17
<212> TYPE: PRT
<213> ORGANISM: Artificial
<220> FEATURE:
<223> OTHER INFORMATION: antibody-binding peptide
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid

<400> SEQUENCE: 21

Arg Gly Asn Cys Ala Tyr His Xaa Gly Gln Leu Val Trp Cys Thr Tyr
1               5                   10                  15

His

<210> SEQ ID NO 22
<211> LENGTH: 17
<212> TYPE: PRT
<213> ORGANISM: Artificial
<220> FEATURE:
<223> OTHER INFORMATION: antibody-binding peptide
<220> FEATURE:
<221> NAME/KEY: misc_feature
<222> LOCATION: (2)..(2)
<223> OTHER INFORMATION: Xaa is homocysteine
<220> FEATURE:
<221> NAME/KEY: misc_feature
<222> LOCATION: (8)..(8)
<223> OTHER INFORMATION: Xaa is lysine, cystein, aspartic acid, glutamic
      acid, 2-amino suberic acid, or diaminopropionic acid
<220> FEATURE:
<221> NAME/KEY: misc_feature
<222> LOCATION: (16)..(16)
<223> OTHER INFORMATION: Xaa is homocysteine

<400> SEQUENCE: 22

Gly Xaa Asp Cys Ala Tyr His Xaa Gly Glu Leu Val Trp Cys Thr Xaa
1               5                   10                  15

His

<210> SEQ ID NO 23
<211> LENGTH: 121
<212> TYPE: PRT
<213> ORGANISM: Artificial Sequence
<220> FEATURE:
<223> OTHER INFORMATION: Kimeric antibody heavy chain variable region 7
      (H07)

<400> SEQUENCE: 23

Glu Val Lys Leu Val Glu Ser Gly Gly Val Leu Val Lys Ser Gly Gly
1               5                   10                  15

Ser Leu Lys Leu Ser Cys Ala Val Ser Gly Phe Thr Phe Ser Asn Tyr
            20                  25                  30

Gly Met Ser Trp Val Arg Gln Thr Pro Glu Lys Arg Leu Glu Trp Val
        35                  40                  45

Ala Thr Ile Ser Asn Ser Gly Arg Tyr Thr Tyr Phe Pro Asp Ser Val
    50                  55                  60

Lys Gly Pro Phe Ala Ile Ser Arg Asp Asn Ala Lys Asn Asn Leu Tyr
65                  70                  75                  80

Leu Gln Met Ser Ser Leu Arg Ser Ala Asp Thr Ala Leu Tyr Tyr Cys
                85                  90                  95

```
Thr Arg His Leu Asp Tyr Ala Asn Tyr Asp Ala Met Asp Tyr Trp Gly
            100                 105                 110

Gln Gly Thr Ser Val Thr Val Ser Ser
        115                 120

<210> SEQ ID NO 24
<211> LENGTH: 111
<212> TYPE: PRT
<213> ORGANISM: Artificial Sequence
<220> FEATURE:
<223> OTHER INFORMATION: Kimeric antibody light chain variable region 8
      (L08)

<400> SEQUENCE: 24

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Thr Thr Ser
            20                  25                  30

Asp Phe Ser Tyr Met His Trp Tyr Gln Gln Lys Pro Gly Gln Pro Pro
        35                  40                  45

Lys Leu Leu Leu Tyr Leu Ala Ser Asn Leu Glu Ser Gly Val Pro Asp
    50                  55                  60

Arg Phe Ser Gly Ser Gly Ser Gly Tyr Asp Phe Tyr Leu Asn Ile His
65                  70                  75                  80

Pro Val Glu Glu Glu Asp Ala Ala Thr Tyr Tyr Cys Gln His Ser Arg
                85                  90                  95

Glu Phe Pro Trp Thr Phe Gly Gly Gly Thr Lys Leu Glu Ile Lys
            100                 105                 110

<210> SEQ ID NO 25
<211> LENGTH: 330
<212> TYPE: PRT
<213> ORGANISM: Artificial Sequence
<220> FEATURE:
<223> OTHER INFORMATION: Heavy chain constant region

<400> SEQUENCE: 25

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 26
<211> LENGTH: 107
<212> TYPE: PRT
<213> ORGANISM: Artificial Sequence
<220> FEATURE:
<223> OTHER INFORMATION: Light chain constant region

<400> SEQUENCE: 26

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
                100                 105
```

RI-LABELED HUMANIZED ANTIBODY

CROSS REFERENCES TO RELATED APPLICATIONS

This application is a continuation of International Patent Application No. PCT/JP2020/039074, filed on Oct. 16, 2020, and claims priority to Japanese Patent Application No. 2019-191562, filed on Oct. 18, 2019, both of which are incorporated herein by reference in their entireties.

BACKGROUND OF THE INVENTION

Field of the Invention

The present invention relates to a conjugate of a chelating agent chelated with a radionuclide, and a mucin subtype 5AC specific humanized antibody, a radiopharmaceutical containing same and use thereof.

Description of the Related Art

Mucin is the main component of mucus secreted from epithelial cell and the like of animal and is a glycoprotein containing a large amount of sugar with a molecular weight of 1-10 million. Mucin includes secretory mucin produced by epithelial cell and the like and membrane-bound mucin that has a hydrophobic transmembrane site and exists while being bound to the cell membrane. The core proteins of mucin are collectively called MUC, and it is known that there are at least 20 types of genes encoding core proteins. One of them, mucin subtype 5AC (MUC5AC), belongs to secretory mucin.

MUC5AC is expressed in the stomach and trachea in normal tissues, and overexpression in pancreatic cancer has been reported. Overexpression has also been reported in thyroid cancer, liver cancer, colorectal cancer, gastric cancer, urothelial cancer, breast cancer, cervical cancer, ovarian cancer, endometrial cancer, and bile duct cancer. As antibodies to MUC5AC, a mouse antibody (non-patent document 1) prepared using, as an antigen, a pancreatic cancer mucin fraction purified from xenograft of human pancreatic cancer cell line SW1990, and chimeric antibodies (patent documents 1, 2, non-patent documents 2, 3) and humanized antibody (patent documents 3, 4) produced based thereon have been reported.

An antibody is used as a reagent for detecting a target molecule, a diagnostic agent, or a pharmaceutical product for treating a disease by utilizing the specificity of the antibody for a target molecule. To further improve the detection performance and therapeutic effect, studies on antibodies bound to radionuclides and drugs are underway. Non-patent document 1 has reported radioimmunotherapy of pancreatic carcinoma model mice using mouse antibody labeled with $^{131}$I which is a β-ray emitting nuclide. Non-patent document 3 has reported SPECT imaging of pancreatic cancer patients using a chimeric antibody labeled with $^{111}$In which is a γ-ray emitting nuclide. Patent documents 3 and 4 describe MUC5AC-specific humanized antibody which is labeled with $^{90}$Y, $^{111}$In, etc.

DOCUMENT LIST

Patent Documents

Patent document 1: JP-A-H7-203974
Patent document 2: JP-A-H11-5749
Patent document 3: WO 2013/157102
Patent document 4: WO 2013/157105

Non-Patent Documents

Non-patent document 1: Japanese Journal of Cancer Research, 87, 977-984, 1996
Non-patent document 2: Japanese Journal of Clinical Medicine vol. 64 extra issue 1, 2006, p274-278
Non-patent document 3: Japanese Journal of Cancer Research, 90, 1179-1186, 1999

SUMMARY OF INVENTION

The present invention aims to provide an anti-MUC5AC humanized antibody labeled with a radionuclide, that is superior in the specificity for mucin subtype 5AC (MUC5AC) and accumulation in tumor.

The present inventors have conducted intensive studies in view of the above-mentioned problems. As a result, they have succeeded in producing a conjugate of a chelating agent chelated with a radionuclide, which is a metal nuclide, and an anti-MUC5AC humanized antibody composed of a specific amino acid sequence, found that the conjugate is superior in specificity for MUC5AC and accumulation in tumor, and confirmed the effects thereof, which resulted in the completion of the present invention.

In one embodiment of the present invention, a conjugate of an antibody and a chelating agent chelated with a radionuclide, wherein the radionuclide is a metal nuclide that emits α particle or positron, and the humanized antibody specifically binding to MUC5AC is provided as the conjugate.

According to the present invention, an anti-MUC5AC humanized antibody labeled with a radionuclide and superior in specificity for MUC5AC and accumulation in tumor, and use of the antibody can be provided.

BRIEF DESCRIPTION OF DRAWINGS

FIG. 22A evaluates the stability of $^{89}$Zr-labeled anti-MUC5AC humanized antibody in human (-■-, ... ■ ... ) plasma and mouse (-●-, ... ● ... ) plasma. Various $^{89}$Zr-labeled antibodies were mixed with human or mouse plasma, and incubated at 37° C. The graph shows time-course changes in the radiochemical purity at each time lapse point. The upper panel shows the results of $^{89}$Zr-labeled anti-MUC5AC humanized antibody prepared using $^{89}$Zr-labeled DOTA-Bn-DBCO (at 24 hr, 48 hr, 168 hr and 378 hr after incubation), and the lower panel shows the results of $^{89}$Zr-labeled anti-MUC5AC humanized antibody prepared using $^{89}$Zr-labeled DOTAGA-DBCO (24 hr, 168 hr and 336 hr after incubation).

FIG. 22B evaluates the stability of $^{225}$Ac-labeled anti-MUC5AC humanized antibody in human (-■-, ... ■ ... ) plasma and mouse (-●-, ... ● ... ) plasma. Various $^{225}$Ac-labeled antibodies were mixed with human or mouse plasma, and incubated at 37° C. The graph shows time-course changes in the radiochemical purity at each time lapse point. The upper panel shows the results of $^{225}$Ac-labeled anti-MUC5AC humanized antibody prepared using $^{225}$Ac-labeled DOTA-Bn-DBCO (at 21 hr, 115 hr, 140 hr and 168 hr after incubation), and the lower panel shows the results of $^{225}$Ac-labeled anti-MUC5AC humanized antibody prepared using $^{225}$Ac-labeled DOTAGA-DBCO (at 48 hr, 168 hr and 336 hr after incubation).

FIG. 28A shows graphs showing the results of the amount of radioactivity per unit weight (% ID/g) in each organ in the biodistribution after 20, 68 and 188 hr from the administration of respective $^{89}$Zr-labeled antibodies prepared using $^{89}$Zr-labeled DOTA-Bn-DBCO (-■-) and $^{89}$Zr-labeled DOTAGA-DBCO ( ... ● ... ). The upper panel shows the results of tumor, and the lower panel shows hematological results.

FIG. 28B shows graphs showing the results of the amount of radioactivity accumulated per unit weight (% ID/g) in each organ in the biodistribution after 20, 68 and 188 hr from the administration of respective $^{89}$Zr-labeled antibodies prepared using $^{89}$Zr-labeled DOTA-Bn-DBCO (-■-) and $^{89}$Zr-labeled DOTAGA-DBCO ( ... ● ... ). The upper panel shows the results of liver, and the lower panel shows the results of kidney.

FIG. 28C shows graphs showing the results of the amount of radioactivity per unit weight (% ID/g) in each organ in the biodistribution after 20, 68 and 188 hr from the administration of respective $^{89}$Zr-labeled antibodies prepared using $^{89}$Zr-labeled DOTA-Bn-DBCO (-■-) and $^{89}$Zr-labeled DOTAGA-DBCO ( ... ● ... ). The upper panel shows the results of heart, and the lower panel shows the results of lung.

DESCRIPTION OF EMBODIMENTS

Figure 1:
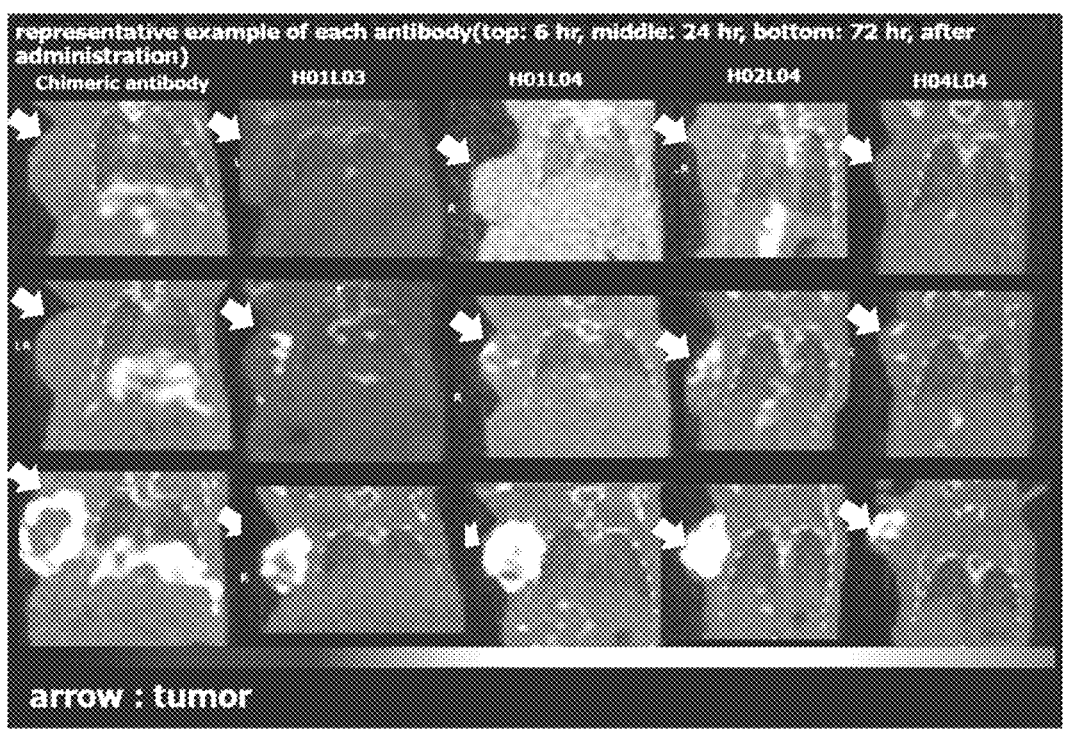
FIG. 1 shows the results of SPECT-CT imaging using respective $^{111}$In-labeled antibodies. The SPECT images of $^{111}$In-labeled antibody are shown.

Unless otherwise specified, the terms used in the present specification can be used in the meaning generally used in the art.

(1) Conjugate 1

The present invention provides a conjugate of an antibody and a chelating agent chelated with a radionuclide (hereinafter to be also referred to as the chelating agent of the present invention), wherein the aforementioned radionuclide is a metal nuclide that emits α particle, and the aforementioned antibody is a humanized antibody specifically binding to MUC5AC (hereinafter to be also referred to as the conjugate of the present invention).

(1-1) Radionuclide

The radionuclide contained in the conjugate of the present invention is a metal nuclide that emits α particles. The metal nuclide may be any nuclide that emits α particles in the decay process of a radioactive metal. Specifically, $^{212}$Bi, $^{213}$Bi, $^{227}$Th, $^{225}$Ac, or the like is preferably used. More preferred is $^{227}$Th or $^{225}$Ac, and further preferred is $^{225}$Ac (actinium-225).

The metal nuclide that emits α particle in the present invention can be produced by a known method using an accelerator such as a cyclotron, a linear accelerator, or the like. For example, $^{225}$Ac can be produced by a nuclear reaction of (p,2n), by irradiating a $^{226}$Ra target with proton by using a cyclotron. The produced metal nuclide that emits α particles can be purified by separating and purifying from the target. For example, purified $^{225}$Ac can be obtained by dissolving the target containing $^{225}$Ac with an acid or the like, adding alkali to the solution to precipitate a salt containing $^{225}$Ac, and separating and purifying the salt. The α particle emitting nuclide purified in this manner can be used for RI labeling by subjecting the nuclide to a chemical treatment as necessary to obtain a chemical form suitable for RI labeling.

(1-2) Antibody

The antibody contained in the conjugate of the present invention is a humanized antibody specifically binding to MUC5AC (hereinafter to be also referred to as the humanized antibody used in the present invention). The antibody is not particularly limited as long as it is a humanized antibody having the ability to specifically bind to MUC5AC. The antibody preferably has stable physical properties and is superior in tumor accumulation. The antibody may be used as an antigen-binding fragment thereof, and such embodiment is also encompassed in the present invention. Specifically, it is contains a specific heavy chain variable region and a specific light chain variable region described below and, when desired, may contain an appropriate heavy chain constant region and an appropriate light chain constant region. In the present specification, the "antigen-binding fragment" means an antibody fragment consisting of a part of the humanized antibody used in the present invention, and having the binding ability to MUC5AC. The number of amino acids contained in the polypeptide constituting the antigen-binding fragment is not particularly limited as long as it has the binding ability to MUC5AC.

An amino acid sequence preferred as the heavy chain variable region of the humanized antibody used in the present invention is shown below. The heavy chain variable region 1 (H01), heavy chain variable region 2 (H02), heavy chain variable region 3 (H03), and heavy chain variable region 4 (H04) respectively correspond to SEQ ID NO: 1-4 in the Sequence Listing attached to the present specification. The underlined part is the CDR site.

```
[heavy chain variable region 1 (H01)]
E V Q L L E S G G G L V Q P G G S L R L S C A

A S G F T F S N Y G M S W V R Q A P G K G L E

W V S T I S N S G R Y T Y F P D S V K G R F T

I S R D N S K N T L Y L Q M N S L R A E D T A

L Y Y C T R H L D Y A N Y D A M D Y W G Q G T

L V T V S S

[heavy chain variable region 2 (H02)]
L V Q L V E S G G G V V R P G G S L R L S C A

A S G F T F S N Y G M S W I R Q A P G K G L E

W V S T I S N S G R Y T Y F P D S V K G R F T

I S R D N A K N S L Y L Q M N S L R A E D T A

L Y Y C T R H L D Y A N Y D A M D Y W G Q G T

L V T V S S

[heavy chain variable region 3 (H03)]
L V Q L V E S G G G V V Q P G R S L R L S C A

A S G F T F S N Y G M S W V R Q A P G K G L E

W V A T I S N S G R Y T Y F P D S V K G R F T

I S R D N S K N T L Y L Q M N S L R A E D T A

V Y Y C T R H L D Y A N Y D A M D Y W G Q G T

L V T V S S
```

```
-continued
[heavy chain variable region 4 (H04)]
E V Q L L E S G G G L V Q P G G S L R L S C A

V S G F T F S N Y G M S W V R Q A P G K G L E

W V S T I S N S G R Y T Y F P D S V K G R F T

I S R D N S R N T L Y L Q M N T L R A E D T A

V Y Y C T R H L D Y A N Y D A M D Y W G Q G T

P V T V S S
```

An amino acid sequence preferred as the light chain variable region of the humanized antibody used in the present invention is shown below. The light chain variable region 1 (L01), light chain variable region 2 (L02), light chain variable region 3 (L03), and light chain variable region 4 (L04) respectively correspond to SEQ ID NO: 5-8 in the Sequence Listing attached to the present specification. The underlined part is the CDR site.

```
[light chain variable region 1 (L01)]
D I V M T Q S P S S L S A S V G D R V T I T C

R A S K S V T T S D F S Y M H W Y Q Q K P G K

A P K L L I Y L A S N L E S G V P S R F S G S

G S G T D F T L T I S S L Q P E D F A T Y Y C

Q H S R E F P W T F G G G T K V E I K

[light chain variable region 2 (L02)]
D V V M T Q S P S T L S A S V G D R V T I T C

R A S K S V T T S D F S Y M H W Y Q Q K P G Q

A P K L L I Y L A S N L E S G V P S R F S G S

G S G T D F T L T I S S L Q P E D P A T Y Y C

Q H S R E F P W T F G Q G T K L E I K

[light chain variable region 3 (L03)]
D I Q M T Q S P S S L S A S V G D R V T I T C

R A S K S V T T S D F S Y M H W Y Q Q K P G K

S P K L L I Y L A S N L E S G V P S R F S G S

G S G T D F S L T I S S L Q P E D F A T Y Y C

Q H S R E F P W T F G G G T K V E I K

[light chain variable region 4 (L04)]
D I V M T Q S P D S L A V S L G E R A T I N C

K A S K S V T T S D F S Y L H W Y Q Q K P G Q

P P K L L I Y L A S N L E S G V P D R P S G S

G S G T D F T L T I S S L Q A E D V A V Y Y C

Q H S R E F P W T F G G G T K L E I K
```

In other words, the heavy chain variable region of the humanized antibody preferred in the present invention consists of the amino acid sequence shown in any one of SEQ ID NO: 1 to SEQ ID NO: 4, and the light chain variable region consists of the amino acid sequence shown in any one of SEQ ID NO: 5 to SEQ ID NO: 8. That is, the humanized antibody used in the present invention consists of a combination of the above-mentioned four heavy chain variable regions (H01-H04) and four light chain variable regions (L01-L04).

A preferable humanized antibody in the present invention has heavy chain variable region H01, H03, or H04, and any one of L01-L04 as the light chain variable region.

The most preferable humanized antibody in the present invention has heavy chain variable region H01 and light chain variable region L03.

The heavy chain variable region of the humanized antibody in the present invention is not limited to those defined by the amino acid sequence shown in SEQ ID NO: 1 to SEQ ID NO: 4 and also includes variants maintaining functions. That is, a mutated heavy chain variable region consisting of an amino acid sequence having not less than 90%, preferably not less than 95%, further preferably not less than 98%, most preferably not less than 99%, sequence identity with the amino acid sequence shown in SEQ ID NO: 1 to SEQ ID NO: 4 is also used as the heavy chain variable region of the humanized antibody to be used in the present invention as long as it can bind to MUC5AC when combined with the light chain variable region in the present invention.

In the present specification, the identity of the amino acid sequence refers to the identity of the amino acid sequences between the two proteins of interest, and is shown by the percentage (%) of amino acid residues that match in the optimal alignment of the amino acid sequences prepared using mathematical algorithms known in the pertinent technical field. The identity of an amino acid sequence can be determined by visual inspection and mathematical calculation, and can be calculated using a homology search program (e.g., BLAST, FASTA) or sequence alignment program (e.g., ClustalW) known to those skilled in the art, or genetic information processing software (e.g., GENETYX [registered trade mark]), and the like. To be specific, the identity of the amino acid sequence in the present specification can be determined using systematic analysis program ClustalW (http://clustalw.ddbj.nig.ac.jp/index.php?lang=ja) published on the website of DDBJ (DNA DataBank of Japan) by the initial setting conditions (Version2.1, Alignment type:slow, DNA Weight Matrix: Gonnet, GAP OPEN: 10, GAP EXTENSION: 0.1).

In addition, as the heavy chain variable region of the humanized antibody to be used in the present invention, a mutated heavy chain variable region consisting of the amino acid sequence shown in SEQ ID NO: 1 to SEQ ID NO: 4, wherein not more than 10, preferably not more than 8, further preferably not more than 5, most preferably not more than 3, amino acids are deleted, substituted, or added, is also used as the heavy chain variable region of the humanized antibody to be used in the present invention as long as it can bind to MUC5AC when combined with the light chain variable region in the present invention.

The light chain variable region of the humanized antibody to be used in the present invention is not limited to the amino acid sequence shown in SEQ ID NO: 5 to SEQ ID NO: 8 and also includes variants maintaining functions. That is, a mutated light chain variable region consisting of an amino acid sequence having not less than 90%, preferably not less than 95%, further preferably not less than 98%, most preferably not less than 99%, sequence identity with the amino acid sequence shown in SEQ ID NO: 5 to SEQ ID NO: 8 is also used as the light chain variable region of the humanized antibody to be used in the present invention as long as it can bind to MUC5AC when combined with the heavy chain variable region in the present invention.

In addition, as the light chain variable region of the humanized antibody to be used in the present invention, a mutated light chain variable region consisting of the amino acid sequence shown in SEQ ID NO: 5 to SEQ ID NO: 8, wherein not more than 10, preferably not more than 8, further preferably not more than 5, most preferably not more than 3, amino acids are deleted, substituted, or added, is also encompassed in the light chain variable region of the humanized antibody to be used in the present invention as long as it can bind to MUC5AC when combined with the heavy chain variable region in the present invention.

The humanized antibody to be used in the present invention can be produced by a method generally performed in the art or a method analogous thereto. Specifically, the following steps can be performed.

Since the amino acid sequences of the heavy chain variable region and the light chain variable region of the humanized antibody to be used in the present invention are disclosed in SEQ ID NO: 1 to SEQ ID NO: 8, a nucleic acid encoding the antibody obtained based on the amino acid sequence information is constructed and inserted into a suitable expression vector. The expression vector can optionally contain, in addition to the nucleic acid encoding the humanized antibody to be used in the present invention, Kozak sequence to improve translation efficiency, a signal sequence that promotes secretion of the humanized antibody to be used in the present invention into the medium when introduced into a host, a promoter sequence, and the like. The vector that can be used in the present invention can be selected from those generally used in the pertinent technical field, and plasmid vector pcDNA3.4 is preferred. Introduction of an expression vector into the host cell is not particularly limited. As a method for introducing a gene into a cell, a method conventionally used in the pertinent technical field, for example, a method known to those skilled in the art such as calcium phosphate method, electroporation method, lipofection method, and DEAE-dextran method can be used. An introduction method using the lipofection method is particularly preferred, as performed in the following Example. As the host cell used for this purpose, those conventionally used in the pertinent technical field can be used. Examples of such host cell include CHO cell, 293 cell, *Escherichia coli*, *Pichia* yeast, Sf9 cell and the like. Currently, an expression system kit for expressing the protein of interest is also commercially available. The ExpiCHO System (Thermo Fisher Scientific) used in the following Example is particularly preferred for rapid and reliable expression of the protein of interest.

The humanized antibody to be used in the present invention can be obtained by inserting a nucleic acid encoding the humanized antibody to be used in the present invention into an expression vector, introducing the nucleic acid into a host cell by the expression vector containing the nucleic acid, culturing the host cell after introduction of the nucleic acid, and obtaining the humanized antibody of the present invention from the culture supernatant thereof by a purification means such as chromatography and the like. In this method, the humanized antibody to be used in the present invention is secreted in a culture supernatant by culturing the host cell. The humanized antibody or an antigen-binding fragment thereof to be used in the present invention can be obtained from the culture supernatant by using a purification means such as chromatography, and the like. As the means for chromatography, various means known in the pertinent technical field such as affinity chromatography, ion exchange chromatography, size-exclusion chromatography and the like can be used. Affinity chromatography with the protein A column used in the following Example is particularly preferred.

In addition, the above-mentioned humanized antibody may be a polyclonal antibody or a monoclonal antibody.

(1-3) Chelating Agent

In the present invention, the chelating agent is not particularly limited as long as it has a site in the structure thereof where radionuclide is coordinated. Preferably, it has a substituent that enables formation of a conjugate of the antibody with the chelate site which is the site where the radionuclide is coordinated. Examples of the chelate site include CB-TE2A (1,4,8,11-Tetraazabicyclo[6.6.2]hexadecane-4,11-diacetic acid), CDTA (Cyclohexane-trans-1,2-diamine tetraacetic acid), CDTPA (4-cyano-4-[[(dodecylthio)thioxomethyl]thio]-Pentanoic acid), DOTA (1,4,7,10-Tetraazacyclododecane-1,4,7,10-tetraacetic acid), DOTMA ((1R,4R,7R,10R)-α,α',α'',α'''-tetramethyl-1,4,7,10-tetraazacyclododecane-1,4,7,10-tetraacetic acid), DOTAM (1,4,7,10-tetrakis(carbamoylmethyl)-1,4,7,10-tetraazacyclododecane), DOTA-GA (α-(2-Carboxyethyl)-1,4,7,10-tetraazacyclododecane-1,4,7,10-tetraacetic acid), DOTP (((1,4,7,10-Tetraazacyclododecane-1,4,7,10-tetrayl)tetrakis(methylene))tetraphosphonic acid), DOTMP (1,4,7,10-Tetraazacyclododecane-1,4,7,10-tetrakis(methylenephosphonic acid)), DOTA-4AMP (1,4,7,10-tetraazacyclododecane-1,4,7,10-tetrakis(acetamidomethylenephosphonic acid), D02P (Tetraazacyclododecane dimethanephosphonic acid), Deferoxamine (DFO), DTPA (Glycine, N,N-bis[2-25 [bis(carboxymethyl)amino]ethyl]-), DTPA-BMA (5,8-Bis(carboxymethyl)-11-[2-(methylamino)-2-oxoethyl]-3-oxo-2,5,8,11-tetraazatridecan-13-oic acid), EDTA (2,2',2'',2'''-(ethane-1,2-diylbis(azanetriyl))tetraacetic acid), NOTA (1,4,7-Triazacyclononane-1,4,7-triacetic acid), NOTP (1,4,7-Triazacyclononane-1,4,7-triyltris(methylenephosphonic acid), TETPA (1,4,8,11-tetraazacyclotetradecane-1,4,8,11-tetrapropionic acid), TETA (1,4,8,11-Tetraazacyclotetradecane-N,N',N'',N'''-tetraacetic acid), TTHA (3,6,9,12-Tetrakis(carboxymethyl)-3,6,9,12-tetraazatetradecanedioic acid), HEHA (1,2,7,10,13-hexaazacyclooctadecane-1,4,7,10,13,16-hexaacetic acid), 1,2-HOPO (N,N',N'',N'''-tetra(1,2-dihydro-1-hydroxy-2-oxopyridine-6-carbonyl)-1,5,10,14-tetraazatetradecane), PEPA(1,4,7,10,13-pentaazacyclopentadecane-N,N',N'',N''',N''''-penta-acetic acid), H4octapa (N,N'-bis(6-carboxy-2-pyridylmethyl)-ethylenediamine-N,N'-diacetic acid), H2bispa2 (6,6'-({9-hydroxy-1,5-bis(methoxycarbonyl)-2,4-di(pyridin-2-yl)-3,7-diazabicyclo[3.3.1]nonane-3,7-diyl}bis(-methylene))dipicolinic acid), H2dedpa (1,2-[{6-(carboxy)-pyridin-2-yl}-methylamino]ethane), H2macropa (6-(1,4,10,13-tetraoxa-7,16-diazacyclooctadecan-N,N'-methyl)picolinic acid), H5decapa (N,N''-bis(6-carboxy-2-pyridylmethyl)-diethylenetriamine-N,N',N''-triacetic acid), H6phospa (N,N'-(methylenephosphonate)-N,N'-[6-(methoxycarbonyl)pyridin-2-yl]-methyl-1,2-diaminoethane), HP-D03A (Hydroxypropyltetraazacyclododecanetriacetic acid), and porphyrin. It is preferable to have a structure derived from a compound represented by the following formula (A).

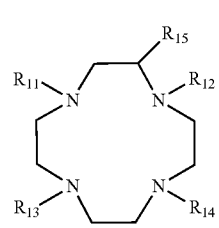

(A)

wherein in the formula (A), $R_{11}$, $R_{13}$ and $R_{14}$ are each independently a group consisting of —$(CH_2)_p$COOH, —$(CH_2)_pC_5H_5N$, —$(CH_2)_pPO_3H_2$, —$(CH_2)_pCONH_2$ or —$(CHCOOH)(CH_2)_pCOOH$, one of $R_{12}$ and $R_{15}$ is a hydrogen atom, a carboxyl group, or a carboxyalkyl group having 2 or 3 carbon atoms, the other is a substituent for conjugating with the aforementioned antibody, p is an integer of not less than 0 and not more than 3, $R_{15}$ is a hydrogen atom when $R_{12}$ is a substituent for conjugating with the aforementioned antibody, and $R_{15}$ is a substituent for conjugating with the aforementioned antibody when $R_{12}$ is not a substituent for conjugating with the aforementioned antibody.

Examples of the specific structure represented by the formula (A) include structures derived from the compounds represented by the following formulas (A-1) to (A-12).

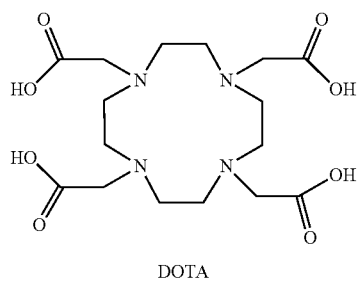

DOTA (A-1)

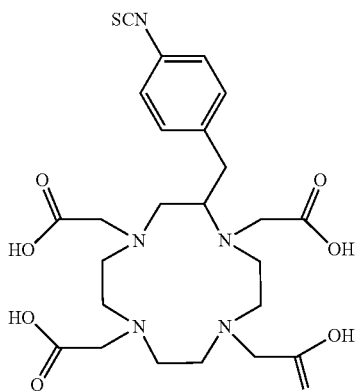

p-SCN-Bn-DOTA (A-2)

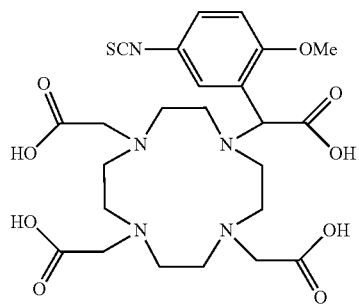

MeO-DOTA-NCS (A-3)

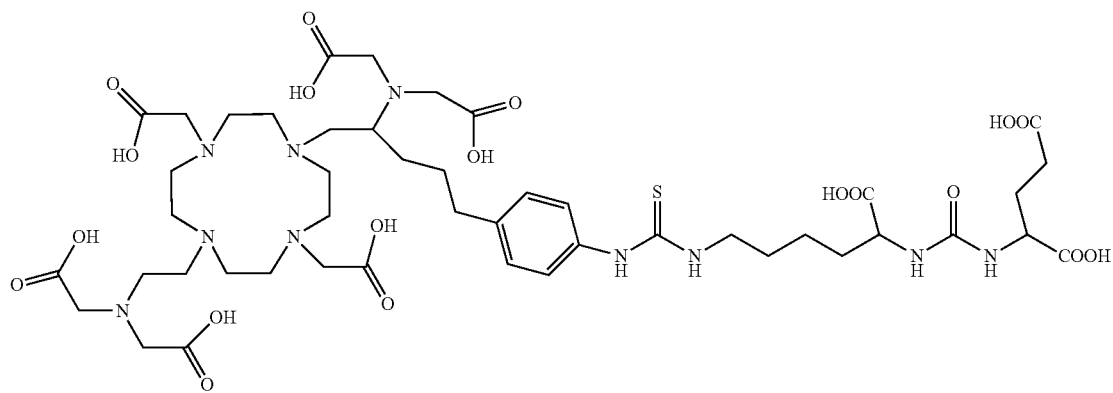

EuK-106 (A-4)

-continued
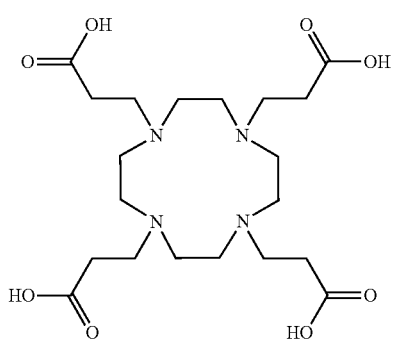
DOTPA
(A-5)
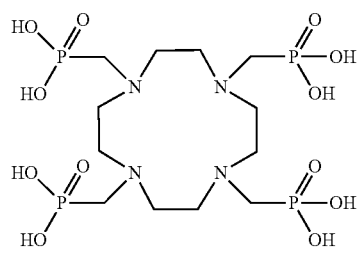
DOTMP
(A-6)
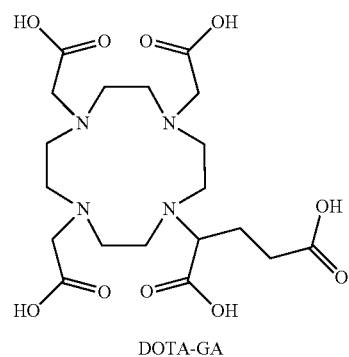
L^py
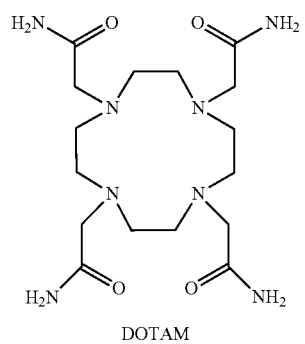
DOTAM
(A-8)
(A-7)
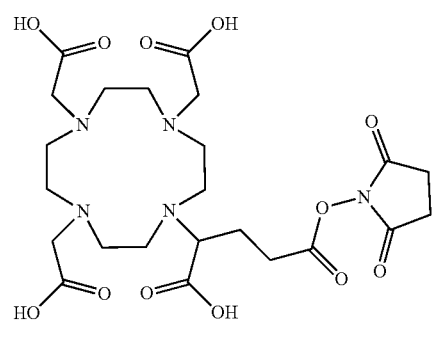
DOTA-GA
(A-9)
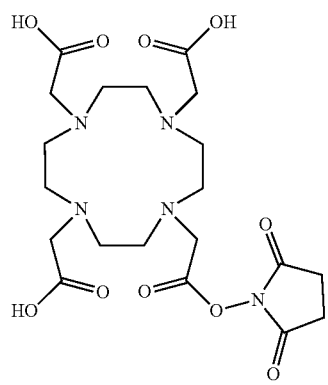
DO3A-NHS
(A-10)
DOTA-GA-NHS
(A-11)
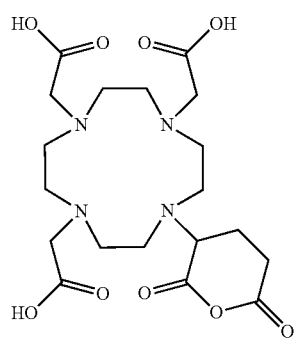
DOTA-GA-anhydride
(A-12)

The linkage site between the chelate site and the substituent that enables formation of a conjugate with the antibody is preferably an amide bond or a thiourea bond, more preferably an amide bond from the aspect of stability.

The amide bond can be formed, for example, by the reaction of an N-hydroxysuccinimidoester (NHS) group of the above-mentioned formula (A-10) or (A-11), or a 2,6-dioxo tetrahydro-2H-pyranyl group of the above-mentioned (A-12) with primary amine. The thiourea bond can be formed by the reaction of an isothiocyanate group of the compound of the above-mentioned formula (A-2), (A-3) with primary amine or a maleimide group.

In the conjugate of the present invention, the chelating agent may be provided at least not less than one molecule, preferably not less than 1 molecule and not more than 8 molecules, per one molecule of the antibody. To maintain the activity of the antibody itself (antigen recognition action, neutralizing action, complement activating action and/or opsonin action), a chelating agent is preferably introduced site-specifically into the Fc region (constant region) of the antibody. In the present invention, the chelating agent is preferably provided at one or two molecules per one molecule of the antibody.

In the conjugate of the present invention, the chelating agent may be connected to the antibody via a linker. Examples of the linker include substituted or unsubstituted alkyl group, substituted or unsubstituted heteroalkyl group, polyethylene glycol (PEG) group, peptides, sugar chain, disulfide group, combination of these and the like.

Preferably, the chelating agent modifies the antibody site-specifically, more preferably in the Fc region, via a linker. In this case, the linker contains a peptide consisting of not less than 13 and not more than 17 amino acid residues represented by the following formula (i) (hereinafter, to be also referred to as "antibody-modification peptide"), and one formed by a cross-linking reaction between the antibody-modification peptide modified with a crosslinking agent and the antibody can be used. In the explanation of the formula (i), the left side of the paper surface of the amino acid sequence indicates the N-terminal side, and the right side of the paper surface of the amino acid sequence indicates the C-terminal side. When the chelating agent is connected to the antibody via the antibody-modification peptide as a linker, the position where the chelating agent and the antibody-modification peptide are linked is not particularly limited. For example, it can be directly or indirectly linked at the N-terminal or C-terminal of the antibody-modification peptide, preferably at the N-terminal. In addition, the C-terminal of the antibody-modification peptide may be modified by, for example, amidation or the like to improve its stability and the like.

(Xa)-Xaa1-(Xb)-Xaa2-(Xc)-Xaa3-(Xd)　　(i)

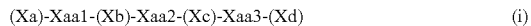

In the formula (i), Xa, Xb, Xc and Xd are each continuous X in the number of a, continuous X in the number of b, continuous X in the number of c, and continuous X in the number of d, respectively,
X is an amino acid residue having neither a thiol group nor a haloacetyl group in the side chain,
a, b, c and d are each independently an integer of not less than one and not more than 5, and satisfy a+b+c+d≤14,
Xaa1 and Xaa3 are each independently an amino acid residue derived from an amino acid having a thiol group in the side chain, or
one is an amino acid residue derived from an amino acid having a thiol group in the side chain and the other is an amino acid residue derived from an amino acid having a haloacetyl group in the side chain, and Xaa1 and Xaa3 are linked, and
Xaa2 is a lysine residue, arginine residue, cysteine residue, aspartic acid residue, glutamic acid residue, 2-aminosuberic acid, or diamino propionic acid, and modified with a crosslinking agent.

Examples of the amino acid residue that may be contained in X in the above-mentioned formula (i) include those derived from amino acids such as glycine, alanine, phenylalanine, proline, asparagine, aspartic acid, glutamic acid, arginine, histidine, serine, threonine, tyrosine, methionine and the like, and X may be an amino acid residue consisting of the same type of amino acid, or different types of amino acids.

In the formula (i), a, b, c and d are not particularly limited as long as they are numbers within the aforementioned range. From the aspect of the stability of binding between the peptide and antibody, a+b+c+d≤14 is to be satisfied, and a is preferably an integer of not less than 1 and not more than 3, b is preferably an integer of not less than 1 and not more than 3, c is preferably an integer of not less than 3 and not more than 5, and d is preferably an integer of not less than 1 and not more than 3.

Xaa1 and Xaa3 are amino acid residues derived from an amino acid having a thiol group in the side chain, and may be the same or different. Examples of the amino acid having a thiol group in the side chain include cysteine and homocysteine. Such amino acid residues are preferably bonded by a disulfide bond, or a sulfide group is preferably bonded thereto via a linker shown by the following formula (4). In the formula (4), the wavy line indicates the binding part with the sulfide group.

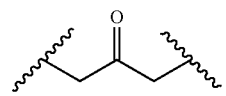

(4)

Instead of the aforementioned combination of Xaa1 and Xaa3, one of Xaa1 and Xaa3 may be an amino acid residue derived from an amino acid having a thiol group in the side chain, and the other may be an amino acid residue derived from an amino acid having a haloacetyl group in the side chain. These are bonded via a thioether bond. The terminal of the haloacetyl group is substituted with a halogen such as iodine or the like, and the halogen is eliminated by a reaction with the thiol group in the other side chain, whereby a thioether bond is formed.

Specific examples of the amino acid sequence of the antibody-modification peptide represented by the formula (i) include the peptides described in WO 2016/186206, WO 2017/217347 and WO 2018/230257, and these can also be used.

Among these, the amino acid sequence of the antibody-modification peptide preferably has any one of the following sequences (1)-(14), more preferably the following sequence (1), (2), (13) or (14). In the following amino acid sequences (1)-(14), (Xaa2) is a lysine residue, a cysteine residue, an aspartic acid residue, a glutamic acid residue, a 2-aminosuberic acid, or a diamino propionic acid, and (Xaa1) and (Xaa3) are each a homocysteine residue. In the following amino acid sequences (1)-(14), the amino acids other than (Xaa1), (Xaa2) and (Xaa3) are indicated by one-letter abbreviations.

(1) DCAYH(Xaa2)GELVWCT (SEQ ID NO: 9)

(2) GPDCAYH(Xaa2)GELVWCTFH (SEQ ID NO: 10)

(3) RCAYH(Xaa2)GELVWCS (SEQ ID NO: 11)

(4) GPRCAYH(Xaa2)GELVWCSFH (SEQ ID NO: 12)

(5) SPDCAYH(Xaa2)GELVWCTFH (SEQ ID NO: 13)

(6) GDDCAYH(Xaa2)GELVWCTFH (SEQ ID NO: 14)

(7) GPSCAYH(Xaa2)GELVWCTFH (SEQ ID NO: 15)

(8) GPDCAYH(Xaa2)GELVWCSFH (SEQ ID NO: 16)

(9) GPDCAYH(Xaa2)GELVWCTHH (SEQ ID NO: 17)

(10) GPDCAYH(Xaa2)GELVWCTFY (SEQ ID NO: 18)

(11) SPDCAYH(Xaa2)GELVWCTFY (SEQ ID NO: 19)

(12) SDDCAYH(Xaa2)GELVWCTFY (SEQ ID NO: 20)

(13) RGNCAYH(Xaa2)GQLVWCTYH (SEQ ID NO: 21)

(14) G(Xaa1)DCAYH(Xaa2)GELVWCT(Xaa3)H (SEQ ID NO: 22)

(1-4) Production Method of Conjugate

The production method of the conjugate of the present invention includes two steps which are a conjugation step of conjugating a chelating agent and an antibody, and a complex formation step of forming a complex of a radionuclide and a chelating agent. The conjugation step may be performed before the complex formation step or after the complex formation step.

In the conjugation step, various methods for chemical modification of antibody are used. Specifically, the methods (a)-(f) can be mentioned:
(a) amine coupling method (a method for modifying the amino group of a lysine residue of an antibody by using a chelating agent or chelate having a carboxyl group activated by an N-hydroxysuccimidyl (NHS) group)
(b) method for modifying a sulfhydryl (SH) group generated by partially reducing a disulfide bond (SS bond) between polypeptide chains at the hinge site of an antibody with a chelating agent or linker having a maleimide group reactive with the SH group
(c) method for modifying cysteine newly introduced into an antibody by an amino acid mutation by genetic engineering with a chelating agent or linker having a maleimide group
(d) method for modifying an azide group of lysine azide newly introduced into an antibody by an amino acid mutation by genetic engineering with a chelating agent or linker having alkyne (e.g., Dibensylciclooctene: DBCO) by using a click reaction
(e) method for modifying glutamine introduced into a specific position of an antibody with a chelating agent or linker having a side chain of lysine by using transglutaminase
(f) method for site-specifically modifying the Fc region of an antibody with a chelating agent or linker having the antibody-modification peptide shown in the aforementioned (i)

In the complex formation step, the chelating agent is chelated with a radionuclide (complex formation). The radionuclide used here is preferably used in a manner permitting ionization, more preferably in the form of an ion, from the viewpoint of increasing the complex formation efficiency. In the complex forming step, the order of addition of the radionuclide to the chelating agent does not matter as long as a complex can be formed with the radionuclide. For example, a solution in which radioactive metal ions are dissolved in a solvent mainly composed of water can be used as a radionuclide.

After complex formation, the obtained complex may be purified using a filtration filter, a membrane filter, a column filled with various fillers, chromatography or the like.

In the production method of the conjugate of the present invention, a conjugation step is preferably performed after the complex formation step.

In a more preferred embodiment, in complex formation step (A), a complex is formed between a radionuclide and a chelating agent having a first atomic group capable of click reaction as a substituent for enabling conjugate formation with the antibody. Then, in conjugation step (B), using an antibody-modification peptide shown by the aforementioned (i) and an antibody-modification linker having a second atomic group capable of click reaction, a click reaction is performed between the peptide-modified antibody in which Fc region is site-specifically modified and the chelating agent with a formed complex which is obtained in step (A) to obtain the conjugate of the present invention.

The steps (A) and (B) are described in detail below.

As the combination of the first atomic group and the second atomic group capable of click reaction, an appropriate combination is selected according to the type of the click reaction. For example, a combination of alkyne and azide, a combination of 1,2,4,5-tetrazine and alkene, and the like can be mentioned. In these atomic groups, the first atomic group has one of the above-mentioned atomic group combination, and the second atomic group has one atomic group which is different from the first atomic group of the above-mentioned atomic group combination. To achieve both the stability of the chelating agent and the antibody and the improvement of the binding efficiency thereof, the chelate linker is preferably alkyne and the antibody-modification linker is preferably azide, or the chelate linker is preferably 1,2,4,5-tetrazine and the antibody-modification linker is preferably alkene. Specific examples of the click reaction by such combinations of atomic groups include a Husgen cyclization addition reaction, an inverse electron-requested Diels-Alder reaction, and the like.

Specific examples of the combination of the atomic groups capable of click reaction include, as shown in the following formulas, a combination of an atomic group containing dibenzylcyclooctyne (DBCO) as alkyne of the first atomic group (the formula (1a)) and an atomic group containing an azide group as azide of the second atomic group (the formula (2a)), and a combination of an atomic group containing 1,2,4,5-tetrazine as the first atomic group (the formula (1b)) and an atomic group containing trans-cyclooctene (TCO) as alkene of the second atomic group (the formula (2b)). Preferred is the combination of the formula (1a) and the formula (2a).

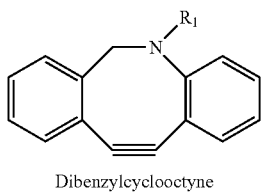

Dibenzylcyclooctyne (1a)

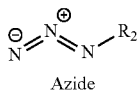

Azide (2a)

wherein $R_1$ is a linkage site with a chelating agent, and $R_2$ is a linkage site with an antibody-modification peptide in the antibody.

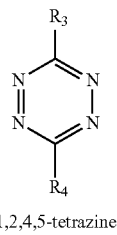

1,2,4,5-tetrazine (1b)

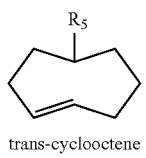

trans-cyclooctene (2b)

wherein one of $R_3$ and $R_4$ is a linkage site with any one chelating agent or an antibody-modification peptide in the antibody, and the other is a hydrogen atom, a methyl group, a phenyl group or a pyridyl group, and $R_5$ is a linkage site with any one chelating agent or an antibody-modification peptide in the antibody depending on $R_3$ or $R_4$.

When an atomic group containing dibenzylcyclooctyne (DBCO) represented by the above-mentioned formula (1a) as alkyne of the first atomic group is used, various commercially available DBCO reagents can be mentioned. Specifically, for example, DBCO-C6-Acid, Dibenzylcyclooctyne-Amine, Dibenzylcyclooctyne Maleimide, DBCO-PEG acid, DBCO-PEG-NHS ester, DBCO-PEG-Alcohol, DBCO-PEG-amine, DBCO-PEG-NH-Boc, Carboxyrhodamine-PEG-DBCO, Sulforhodamine-PEG-DBCO, TAMRA-PEG-DBCO, DBCO-PEG-Biotin, DBCO-PEG-DBCO, DBCO-PEG-Maleimide, TCO-PEG-DBCO, DBCO-mPEG and the like can be selected, and Dibenzylcyclooctyne Maleimide is preferably used.

In step (A), more preferably, a chelating agent having a structure represented by the following formula (ii) is used.

A-B—C (ii)

In the formula (ii), A is a chelate site represented by the following formula (iia).

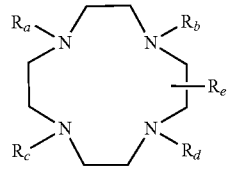

(iia)

In the formula (iia), $R_a$, $R_b$ and $R_c$ are each independently a group consisting of —$(CH_2)_p$COOH, —$(CH_2)_p$C$_5$H$_5$N, —$(CH_2)_p$PO$_3$H$_2$, —$(CH_2)_p$CONH$_2$ or —(CHCOOH)$(CH_2)_p$COOH, p is an integer of not less than 0 and not more than 3, one of Rd and Re is a binding site (*) with B, and other is a hydrogen atom or a group consisting of —$(CH_2)_p$COOH, —$(CH_2)_p$C$_5$H$_5$N, —$(CH_2)_p$PO$_3$H$_2$, —$(CH_2)_p$CONH$_2$ or, —(CHCOOH)(CH$_2$), COOH, and p is an integer of not less than 0 and not more than 3.

In the formula (ii), B is represented by the following formula (iib).

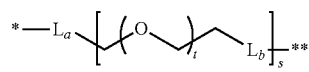

(iib)

In the formula (iib), $L_a$ and $L_b$ are each independently a bond linker containing at least an amide bond or a thiourea bond and not less than 1 and not more than 50 carbon atoms, t is an integer of not less than 0 and not more than 30, s is 0 or 1, * is a binding site with A, and ** is a binding site with C.

In the formula (ii), C is either an alkyne derivative represented by the following formula (iic) or a tetrazine derivative represented by the formula (iid).

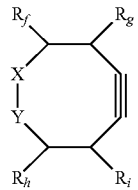

(iic)

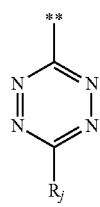

(iid)

In the formula (iic), X is CHR$_k$— or N—, Y is CHR$_k$ or C=O, R$_k$ is independently a hydrogen atom or an alkyl group having not less than 1 and not more than 5 carbon atoms, when X is CHR$_k$— and Y is CHR$_k$, then R$_k$ moieties may be joined to form a cycloalkyl group, R$_f$, R$_g$, R$_h$ and R$_i$ are each independently a hydrogen atom, a halogen atom, or an alkyl group having not less than 1 and not more than 5 carbon atoms, R$_f$ and N may be joined, or R$_h$ and R$_i$ may be joined to form a hydrocarbon ring,  is a binding site with B, in the formula (iid), ** is a binding site with B, and R$_j$ is a hydrogen atom, a methyl group, a phenyl group or a pyridyl group.

As the chelating agent used in step (A), a DOTA derivative of the above-mentioned formula (iia) wherein $R_a$ to $R_d$ are $-(CH_2)_pCOOH$, p is 1, Re is a binding site with B; or DO3A derivative or DOTAGA derivative wherein $R_a$ to $R_c$ are $-(CH_2)_pCOOH$, p is 1, $R_d$ is a binding site (*) with B, and $R_e$ is a hydrogen atom is more preferred.

In the formula (ii), a DOTA-PEGt-DBCO derivative wherein A is the above-mentioned DOTA derivative, in B, $L_a$ is a bond linker containing a thiourea bond and having not less than 1 and not more than 50 carbon atoms, s is 0 or 1, when s is 1, t is an integer of not less than 0 and not more than 30, $L_b$ is a bond linker containing an amide bond or a thiourea bond and having not less than 1 and not more than 50 carbon atoms, and C is an alkyne derivative represented by the formula (iic), wherein, in the formula (iic), X is N—, Y is $CHR_k$, $R_k$ is a hydrogen atom, $R_f$ and $R_g$ are jointed to form a benzene ring, $R_h$ and $R_i$ are jointed to form a benzene ring, and  is a binding site with B; or a DOTA-PEGt-Tz derivative wherein, in B, $L_a$ is a bond linker containing a thiourea bond and having not less than 1 and not more than 50 carbon atoms, s is 0 or 1, when s is 1, t is an integer of not less than 0 and not more than 30, $L_b$ is a bond linker containing an amide bond or a thiourea bond and having not less than 1 and not more than 50 carbon atoms, and C is a tetrazine derivative represented by the formula (iid), is further more preferred.

In the formula (ii), a DO3A-PEGt-DBCO derivative wherein A is the above-mentioned DO3A derivative, in B, $L_a$ is a bond linker containing an amide bond or a thiourea bond and having not less than 1 and not more than 50 carbon atoms, s is 0 or 1, when s is 1, t is an integer of not less than 0 and not more than 30, $L_b$ is a bond linker containing an amide bond and having not less than 1 and not more than 50 carbon atoms, and C is an alkyne derivative represented by the formula (iic), wherein, in the formula (iic), X is N—, Y is $CHR_k$, $R_k$ is a hydrogen atom, $R_f$ and Rg are jointed to form a benzene ring, $R_h$ and $R_i$ are jointed to form a benzene ring, and  is a binding site with B is further more preferred.

In the formula (ii), a DOTAGA-PEGt-DBCO derivative wherein A is the above-mentioned DOTAGA derivative, in B, $L_a$ is a bond linker containing an amide bond or a thiourea bond and having not less than 1 and not more than 50 carbon atoms, s is 0 or 1, when s is 1, t is an integer of not less than 0 and not more than 30, $L_b$ is a bond linker containing an amide bond or a thiourea bond and having not less than 1 and not more than 50 carbon atoms, and C is an alkyne derivative represented by the formula (iic), wherein, in the formula (iic), X is N—, Y is $CHR_k$, $R_k$ is a hydrogen atom, $R_f$ and $R_g$ are jointed to form a benzene ring, $R_h$ and $R_i$ are jointed to form a benzene ring, and  is a binding site with B is further more preferred.

In the molar ratio of the chelating agent and radionuclide as chelate site/radionuclide, the lower limit is preferably not less than 10/1, more preferably not less than 100/1, further preferably not less than 500/1, and the upper limit is preferably not more than 10000/1, more preferably not more than 8000/1, further preferably not more than 7000/1. For example, the range of not less than 100/1 and not more than 7000/1 is preferred, and not less than 500/1 and not more than 7000/1 is more preferred.

The complex formation reaction is preferably performed in a solvent. As the solvent, water, saline, buffers such as sodium acetate buffer, ammonium acetate buffer, phosphate buffer, phosphate buffered saline, tris hydroxymethylaminomethane buffer (Tris buffer), 4-(2-hydroxyethyl)-1-piperazineethanesulfonic acid buffer (HEPES buffer), tetramethylammonium acetate buffer and the like, and the like can be used.

While the amount of the solvent is not particularly limited, from the aspect of practicality in the production step, the lower limit at the start of step (A) is not less than 0.01 mL, preferably not less than 0.1 mL, more preferably not less than 1.0 mL, further preferably not less than 10 mL, further more preferably not less than 100 mL, and upper limit is preferably not more than 1000 mL, more preferably not more than 100 mL, further preferably not more than 10 mL, further more preferably not more than 1.0 mL. For example, it is within the range of not less than 0.01 mL and not more than 100 mL.

As the concentration of the chelating agent in the reaction mixture of the complex formation reaction, from the aspect of the yield of the desired chelating agent, the lower limit at the start of step (A) is each independently preferably not less than 0.001 µmol/L, more preferably not less than 0.01 µmol/L, further preferably not less than 0.1 µmol/L, more preferably not less than 1 µmol/L, and the upper limit is preferably not more than 1000 µmol/L, more preferably not more than 100 µmol/L, further preferably not more than 10 µmol/L. For example, it is within the range of not less than 1 µmol/L and not more than 100 µmol/L.

The temperature of the complex formation reaction may be, for example, room temperature (25° C.) or under heating conditions. To simultaneously achieve suppression of decomposition of the chelating agent and improvement of complex formation efficiency, the lower limit is preferably not less than 20° C., more preferably not less than 30° C., further preferably not less than 35° C., further more preferably not less than 37° C., particularly preferably not less than 45° C. The upper limit is preferably not more than 150° C., more preferably not more than 120° C., further preferably not more than 100° C., further more preferably not more than 90° C. For example, a range of not less than 30° C. and not more than 100° C. is preferred, and a range of not less than 35° C. and not more than 90° C. is more preferred.

As the reaction time, the aforementioned reaction temperature should be satisfied, and the lower limit is preferably not less than 5 min, more preferably not less than 10 min, further preferably not less than 20 min, further more preferably not less than 30 min, particularly preferably not less than 45 min, and the upper limit is preferably not more than 180 min, more preferably not more than 150 min, further preferably not more than 120 min, further more preferably not more than 90 min, particularly preferably not more than 60 min. For example, the range of not less than 10 min and not more than 150 min is preferred, and the range of not less than 10 min and not more than 60 min is more preferred.

The antibody to be used in step (B) is a peptide-modified antibody in which Fc region (constant region) of humanized antibody as described in detail in the above-mentioned "(1-2) Antibody" is site-specifically modified using the antibody-modification peptide shown in the aforementioned (i), and an antibody-modification linker having the second atomic group capable of click reaction.

The antibody-modification peptide can be produced using a combination of amino acids regardless of natural amino acids and unnatural amino acids, by subjecting to peptide synthesis methods such as liquid phase synthesis process, solid phase synthesis process, automatic peptide synthesis method, gene recombinant method, phage display method and the like. In the synthesis of the peptide, where necessary, the functional groups of the amino acids to be used may be protected. These methods can be performed according to the method described in, for example, WO 2017/217347 and WO 2018/230257.

The antibody-modification linker may be one in which an antibody-modification peptide and a linker represented by the following formula (S1) are bonded.

*-((L$_1$)$_m$-Z)$_k$-L$_2$-AG$_2$ (S1)

wherein * is a binding site with the N-terminal or C-terminal of peptide,
L$_1$ is a linker moiety of polyethylene glycol (PEG),
m is an integer of not less than 1 and not more than 50,
Z is a second linker moiety that binds (L$_1$)$_m$ and L$_2$,
k is 0 or 1,
L$_2$ is the second PEG linker moiety, and
AG$_2$ is a second atomic group.

In the aforementioned formula (S1), the structure of Z is not particularly limited as long as it is a linker structure that binds (L$_1$)$_m$ and L$_2$ to each other, and includes, for example, an amino acid sequence consisting of not less than 1 and not more than 5 amino acid residues. In this case, the amino acid sequence contained in Z preferably contains a cysteine residue, and is more preferably bonded to L$_2$ via a thioether group formed by the bond between the thiol group of the cysteine residue and a maleimide group.

In the present invention, the PEG linker moiety constituting L$_2$ preferably has the structure shown by the following formula (P2). In the formula (P2), n is an integer of preferably not less than 1 and not more than 50, more preferably not less than 1 and not more than 20, further preferably not less than 2 and not more than 10, further more preferably not less than 2 and not more than 6.

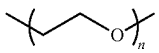
(P2)

One end of the structure of the PEG linker moiety may be modified by a structure derived from a commercially available PEGylation reagent or a structure derived from a reagent generally used for PEGylation. Although not particularly limited, examples thereof include structures derived from diglycolic acid or a derivative thereof, and maleimide or a derivative thereof.

As a method for introducing the aforementioned second atomic group into an antibody-modification linker, an introduction method including obtaining an antibody-modification peptide having a desired amino acid sequence by the aforementioned method, dissolving the peptide in a solution containing a solubilizing agent and a reducing agent and, where necessary, an acid, adding an organic solvent solution of an atomic group containing an azide group or trans-cyclooctene (TCO) as the second atomic group to the solution, and stirring the mixture at room temperature can be mentioned.

When an atomic group containing an azide group is introduced as the second atomic group, the azide group is directly introduced into the N-terminal or C-terminal of a peptide by using a commercially available azide group-introducing reagent according to a conventional method, or an atomic group containing an azide group can be introduced via the aforementioned linker structure. Examples of the azide group-introducing reagent to be used include silyl azide, azide phosphate, alkyl ammonium azide, inorganic azide, sulfonyl azide, PEG azide, and the like.

When an atomic group containing TCO is introduced as the second atomic group, TCO is directly introduced into the N-terminal or C-terminal of a peptide by using a commercially available click chemistry reagent containing TCO according to a conventional method, or an atomic group containing TCO can be introduced via the aforementioned linker structure.

The method for binding an antibody-modification peptide to an antibody to obtain a peptide-modified antibody can be performed using, for example, a crosslinking agent. A crosslinking agent is a chemical substance for linking an antibody-modification peptide and an antibody by a covalent bond. Examples thereof include a crosslinking agent preferably containing two or more succinimidyl groups such as disuccinimidyl glutarate (DSG), disuccinimidyl suberate (DSS) and the like, a crosslinking agent consisting of a compound containing two or more imidic acid moieties such as dimethyl adipimidate and the like, or a salt thereof, a crosslinking agent consisting of a compound having a disulfide bond such as dimethyl 3,3'-dithiobispropionimidate, dithiobissuccinimidylpropionic acid, and the like, or a salt thereof, and the like. Using such crosslinking agent, a crosslinking reaction can be caused between an amino acid residue of Xaa2 in the antibody-modification peptide and an antibody. When, for example, the humanized antibody of the present invention is used as the antibody, the crosslinking reaction in the antibody occurs site-specifically between an amino acid residue of Xaa2 and a Lys252 residue according to the Eu numbering in the humanized antibody of the present invention. These Lys residues are present in the Fc region of the humanized antibody of the present invention.

The method for binding the antibody-modification peptide to the antibody can be performed, for example, by dispersing the aforementioned antibody-modification peptide, an antibody, a crosslinking agent, and a catalyst as necessary in an appropriate buffer at not less than 10° C. and not more than 30° C. The reaction time may be about not less than 10 min to 2 hr. The molar ratio at the time of reaction of the peptide and the antibody is preferably not less than ⅕, more preferably not less than ⅓, further preferably not less than 1/1.5 as the lower limit of the antibody/peptide, and the upper limit is preferably not more than 20/1, more preferably not more than 10/1, further preferably not more than 5/1, further more preferably not more than 1/1, particularly preferably not more than 1/1.7. For example, the range of not less than ⅕ and not more than 20/1 is preferable, and not less than 1/1.5 and not more than 1/1.7 is more preferable.

The peptide-modification antibody obtained through the above steps is a mixture containing an antibody in which one molecule of antibody-modification peptide is bound to one molecule of antibody (hereinafter referred to as "monovalent antibody") and an antibody in which two molecules of antibody-modification peptide are bound to one molecule of antibody (hereinafter referred to as "divalent antibody") at any ratio. This may be used as it is for the subsequent steps, or an unmodified antibody, a monovalent antibody, and a divalent antibody are separated and purified by a method such as filtration filter, membrane filter, column filled with various fillers, various chromatographies and the like, and only the antibody having any valence may be subjected to the subsequent steps. When the unmodified antibody cannot be separated from the antibody having other valence as a result of purification, a mixture containing these may be subjected to the subsequent steps.

When an unmodified antibody, a monovalent antibody, and a divalent antibody are separated and purified, any of the above-mentioned purification methods may be used for separation and purification. It is preferable to use a column filled with various fillers, and it is more preferable to use a column filled with a filler suitable for separation and purification of protein such as antibody and the like.

The filler suitable for separation and purification of protein such as antibody and the like is not particularly limited as long as it is a filler in which an immunoglobulin-binding protein is immobilized on a carrier composed of a water-insoluble substrate, and which specifically binds to an antibody. Examples of the immunoglobulin-binding protein include protein A, protein G, protein L and the like. These immunoglobulin-binding proteins may be genetically engineered recombinants. Examples of the recombinant immunoglobulin-binding protein include genetically-engineered protein A, genetically-engineered protein G, and fused protein A domain and protein G domain. In the present invention, as a filler suitable for separation and purification of at least a monovalent antibody and a divalent antibody, protein A is more preferred, and genetically-engineered protein A is more preferred. As used herein, protein A and protein G are protein molecules that can specifically bind to an antibody molecule IgG, and classified as protein A (*Staphylococcus aureus*) or protein G (*streptococcus: Streptococcus* genus) depending on the difference in the origin of the isolated microorganisms. The genetically-engineered protein A is a protein A in which at least one amino acid mutation has been introduced into an amino acid residue of any of the IgG binding domains (E, D, A, B and C domains) of protein A. In the present invention, genetically-engineered protein A in which the domain into which at least one amino acid mutation has been introduced is multimerized is preferable, genetically-engineered protein A in which A, B or C domain into which at least one amino acid mutation of protein A has been introduced is multimerized is more preferable, and genetically-engineered protein A multimerized to not less than a dimer and not more than a pentamer is further more preferable. The amino acid mutation may be derived from any mutation such as substitution, deletion, insertion and the like of the amino acid sequence or the base sequence encoding the amino acid in the transcriptional translation step of the gene. Examples thereof that are not particularly limited include the genetically-engineered protein A described in WO 2003/080655, WO 2011/118699 and the like.

Examples of the water-insoluble substrate on which immunoglobulin-binding proteins are immobilized include inorganic carriers such as glass beads, silica gel and the like, organic carriers such as synthetic polymers (e.g., crosslinked poly(vinyl alcohol), crosslinked polyacrylate, crosslinked polyacrylamide, crosslinked polystyrene) and polysaccharides (e.g., crystalline cellulose, crosslinked cellulose, crosslinked agarose, crosslinked dextran), and organic-organic, organic-inorganic conjugate carriers and the like obtained from combinations of these, and the like.

The column filled with the aforementioned genetically-engineered protein A as a filler is commercially available as, for example, KanCap (registered trade mark) series (KANEKA KanCapA prepacked column) of KANEKA CORPORATION, HiTrap (registered trade mark) series (HiTrap Mabselect, HiTrap Mabselect SuRe, HiTrap Mabselect Xtra) of GE Healthcare, HiScreen series (HiScreen Mabselect SuRe) of GE Healthcare, TOYOPEARL (registered trade mark) series (TOYOPEARL AF-rProtein A-650F) of Tosoh Corporation, and the like.

The separation and purification of peptide-modified antibody used for click reaction in step (B) is explained below as an example.

A peptide-modified antibody is subjected to a click reaction in step (B) after an antibody modification step in which a modified antibody is obtained by site-specifically modifying an Fc region of an antibody by a linker provided with an antibody-modification peptide (antibody-modification linker), and an antibody purification step in which the modified antibody is purified using the aforementioned carrier with an immunoglobulin-binding protein immobilized thereon. In addition, the antibody purification step further includes a retention step of retaining the modified antibody retained on the carrier, a washing step of washing the modified antibody not retained on the carrier, and an elution step of eluting the modified antibody retained on the carrier in the retention step.

More specifically, in the antibody modification step, a modified antibody is obtained as a mixture containing an unmodified antibody not modified by an antibody-modification linker, a monovalent antibody, and a divalent antibody and, in the antibody purification step, the first antibody composition containing relatively large amounts of the unmodified antibody and the monovalent antibody and the second antibody composition containing a relatively large amount of the divalent antibody are respectively eluted utilizing the difference in the interaction of the unmodified antibody, monovalent antibody and divalent antibody with immunoglobulin-binding proteins. That is, in the retention step and washing step among the antibody purification steps, the second antibody composition containing a relatively large amount of peptide-modified antibody (divalent antibody) having a low degree of interaction with immunoglobulin-binding proteins is eluted and, in the elution step among the antibody purification steps, the first antibody composition containing a relatively large amount of peptide-modified antibody (unmodified antibody and monovalent antibody) having a high degree of interaction with immunoglobulin-binding proteins is eluted. As used herein, "containing a relatively large amount of unmodified antibody and monovalent antibody" means that the total amount of unmodified antibody and monovalent antibody contained in the first antibody composition is larger than that of the divalent antibody contained in the antibody composition, preferably that the total amount of the unmodified antibody and monovalent antibody is not less than 55%, not less than 63%, not less than 70%, not less than 80%, or not less than 90%, of the total amount (100%) of the unmodified antibody and modified antibody contained in the antibody composition. In addition, "containing a relatively large amount of divalent antibody" means that the amount of divalent antibody contained in the second antibody composition is larger than that of the monovalent antibody contained in the antibody composition, preferably that the amount of divalent antibody is not less than 55%, not less than 63%, not less than 70%, not less than 80%, or not less than 90%, of the total amount (100%) of the unmodified antibody and modified antibody contained in the antibody composition.

In the retention step, a solution containing the mixture of the unmodified antibody, monovalent antibody and divalent antibody obtained in the antibody modification step is added to a column, and unmodified antibody and monovalent antibody retained on the carrier are retained on the column and the divalent antibody not retained on the carrier is allowed to pass through. The solution that passed through in the retention step constitutes a part of the second antibody composition. To facilitate retention of the unmodified antibody and monovalent antibody on the column and to prevent aggregation or denaturation of these, it is preferable to dilute the mixed solution of the peptide-modified antibody with an appropriate dilution solvent and add same to the column. The dilution solvent is not particularly limited as long as the peptide-modified antibody dissolves and does not easily aggregate or denature in the solvent, and water, saline, buffers such as sodium acetate buffer, ammonium acetate buffer, phosphate buffer, phosphate buffered saline, 2-amino-2-(hydroxymethyl)propane-1,3-diol (Tris) buffer, 2-[4-(2-hydroxyethyl)-1-piperazinyl]-ethanesulfonic acid (HEPES) buffer and the like, and the like can be used. It is preferable to use any of the aforementioned buffers, more preferably sodium acetate buffer. When a buffer is used as a dilution solvent, the concentration of the buffering agent is not less than 10 mmol/L, preferably not less than 15 mmol/L, more preferably not less than 20 mmol/L as the lower limit, and not more than 1000 mmol/L, preferably not more than 500 mmol/L, more preferably not more than 100 mmol/L as the upper limit. In addition, to reduce non-specific binding of the divalent antibody and antibody-modification peptide to the column carrier, the elution solvent may contain an additive such as sodium chloride, potassium chloride and the like. The concentration of the additive contained in the elution solvent is not particularly limited and may be, for example, 0.15 mol/L.

In the washing step, the modified antibody remaining in the column is eluted from the column by using a wash solvent. The solution that passed through the column in the aforementioned retention step and the solution eluted from the column in the washing step contain a relatively large amount of the divalent antibody, and therefore, these can be combined and used as the second antibody composition.

The wash solvent is not particularly limited as long as the peptide-modified antibody dissolves and does not easily aggregate or denature in the solvent, and it is a buffer having appropriate pH buffering capacity, and buffers such as sodium acetate buffer, ammonium acetate buffer, phosphate buffer, phosphate buffered saline, 2-amino-2-(hydroxymethyl)propane-1,3-diol (Tris) buffer, 2-[4-(2-hydroxyethyl)-1-piperazinyl]-ethanesulfonic acid (HEPES) buffer and the like, and the like can be used. It is preferable to use any of the aforementioned buffers, more preferably sodium acetate buffer. The concentration of the buffering agent used as the wash solvent is not less than 20 mmol/L, preferably not less than 30 mmol/L as the lower limit, and not more than 200 mmol/L, preferably not more than 70 mmol/L as the upper limit. The pH of the wash solvent is not less than 4.0, preferably not less than 4.5, more preferably not less than 4.8 as the lower limit, and not more than 7.4, preferably not more than 6.0, more preferably not more than 5.2 as the upper limit. Furthermore, to reduce non-specific binding of the divalent antibody and antibody-modification peptide to the column carrier, the elution solvent may contain an additive such as sodium chloride, potassium chloride and the like. The concentration of the additive contained in the elution solvent is not particularly limited and may be, for example, 0.15 mol/L.

In the elution step, the modified antibody retained on the carrier is eluted from the column by using an elution solvent. That is, the first antibody composition containing a relatively large amount of unmodified antibody and monovalent antibody is eluted from the column by using an elution solvent.

As the elution solvent, a buffer such as sodium acetate buffer, ammonium acetate buffer, citrate buffer and the like can be used. In addition, to reduce non-specific binding to the antibody-modification linker, unmodified antibody and modified antibody column carrier, the elution solvent may contain an additive such as sodium chloride, potassium chloride and the like. The concentration of the additive contained in the elution solvent is not particularly limited and may be, for example, 0.15 mol/L.

When the elution solvent contains a buffering agent, the concentration of the buffering agent is not less than 20 mmol/L, preferably not less than 30 mmol/L as the lower limit, and not more than 200 mmol/L, preferably not more than 70 mmol/L as the upper limit. In addition, to weaken the interaction between the unmodified antibody and monovalent antibody, and the immunoglobulin-binding protein, and to prevent denaturation and aggregation of the antibody, the pH of the elution solvent is not less than pH 3.0 as the lower limit, and not more than pH 4.2 as the upper limit.

The first antibody composition or the second antibody composition obtained in the antibody purification step may be used as it is for the click reaction in the subsequent step (B), or may be used for the click reaction in step (B) after adjusting the protein concentration of the peptide-modified antibody contained.

The click reaction in step (B) is performed between the first atomic group capable of click reaction which is contained in the chelating agent, and the second atomic group capable of click reaction which is contained in the peptide-modified antibody. By such click reaction, a binding group (substituent capable of forming conjugate with antibody) that links a chelating agent and an antibody is formed.

When the peptide-modified antibody and the complex obtained in step (A) are capable of click reaction, the order of addition of these does not matter. For example, one of the complex and the peptide-modified antibody is added to a reaction container containing a solvent, and then the other is added to perform the reaction, or one of the chelating agent and the antibody is dispersed in a solvent and the other is added to the dispersion to perform the reaction. Alternatively, these may be simultaneously added to a reaction container containing a solvent to perform the reaction.

As the solvent to be used for the click reaction in step (B), a solvent containing water can be used. For example, water, saline, buffers such as sodium acetate buffer, ammonium acetate buffer, phosphate buffer, phosphate buffered saline, Tris buffer, HEPES buffer, tetramethylammonium acetate buffer and the like, and the like can be used. When a buffer is used, to simultaneously achieve the stability of the complex and the antibody, and the bond efficiency of these, the pH at 25° C. is preferably set to not less than 4.0 and not more than 10.0, further preferably not less than 5.5 and not more than 8.5.

While the amount of the reaction mixture is not particularly limited, from the aspect of practicality in the production step, the lower limit at the start of step (B) is preferably not less than 0.001 mL, more preferably not less than 0.01 mL, further preferably not less than 0.1 mL, further more preferably not less than 1 mL, and the upper limit is preferably not more than 1000 mL, more preferably not more than 100 mL, further preferably not more than 10 mL, further more preferably not more than 1 mL. For example, the range of not less than 0.001 mL and not more than 1000 mL is preferable, and the range of not less than 0.1 mL and not more than 10 mL is more preferable.

As the concentrations of the chelating agent and the antibody in the reaction mixture, each independently, the lower limit at the start of step (B) is preferably not less than 0.001 μmol/L, more preferably not less than 0.01 μmol/L, further preferably not less than 0.1 μmol/L, further more preferably not less than 1.0 μmol/L, and the upper limit is preferably not more than 1000 μmol/L, more preferably not more than 100 μmol/L. For example, the range of not less than 0.1 μmol/L and not more than 1000 μmol/L is preferable, and the range of not less than 1 μmol/L and not more than 100 μmol/L is more preferable, from the aspect of the yield of the desired conjugate.

To prevent unintended denaturation of the antibody and increase the reaction efficiency, the upper limit of the reaction temperature of the click reaction in step (B) is preferably not more than 50° C., more preferably not more than 40° C. The lower limit of the reaction temperature is not particularly limited as long as the reaction proceeds, and is preferably not less than 15° C. The reaction time of the click reaction is, on the condition that it is the aforementioned reaction temperature, preferably not less than 5 min, more preferably not less than 10 min, preferably not more than 24 hr, more preferably not more than 20 hr. For example, the range of not less than 5 min and not more than 24 hr is preferable, and the range of not less than 10 min and not more than 20 hr is more preferable.

The obtained conjugate may be used as it is or purified using a filtration filter, a membrane filter, a column filled with various fillers, chromatography or the like.

In the conjugate produced by steps (A) and (B), a specific site of a humanized antibody specifically binding to MUC5AC (e.g., lysine residue in the Fc region of antibody) is specifically modified with a chelating agent. This conjugate comprises one or two molecules of the aforementioned chelating agent per one molecule of the antibody. The chelating agent site-specifically modifies the Fc region of the antibody of the present invention via a linker. The linker is constituted of a chelate linker connecting to a chelating agent, a first atomic group that connects to the linker, a second atomic group that can perform click reaction with the first atomic group, and an antibody-modification linker connecting to the second atomic group, which includes an antibody-modification peptide represented by the above-mentioned formula (i). Therefore, the linker has a chemical structure derived from the first atomic group and the second atomic group. As such chemical structure, a triazole skeleton-containing structure represented by the following formula (10a) or (10b) or a pyridazine skeleton-containing structure represented by the following formula (10c) can be considered. Since the formula (10a) and the formula (10b) are isomers, they may be contained at any ratio.

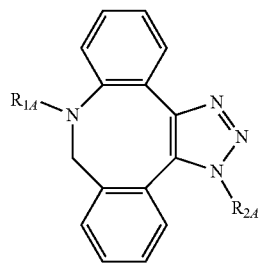

(10a)

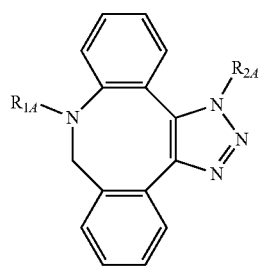

(10b)

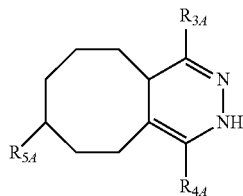

(10c)

In the formula (10a) and the formula (10b), $R_{1A}$ is a binding site with a chelate linker, and $R_{2A}$ is a binding site with an antibody-modification linker. In the formula (10c), one of $R_{3A}$ and $R_{4A}$ is a hydrogen atom, a methyl group, a phenyl group or a pyridyl group, and the other is a binding site with a chelate linker, and $R_{5A}$ is a binding site with an antibody-modification linker.

(1-5) Radiopharmaceutical

The conjugates produced by the methods of the aforementioned (1-4) may also be used as they are or after purification for the preparation of radiopharmaceuticals containing the conjugate as the active ingredient. A radiopharmaceutical refers to a composition containing the conjugate of the present invention, namely, an anti-MUC5AC humanized antibody labeled with a radionuclide (metal nuclide emitting a particle) or a derivative thereof, and in a form suitable for administration to the body of a subject. A radiopharmaceutical can be produced, for example, by dissolving the conjugate of the present invention produced by the aforementioned method in a solvent mainly composed of water and substantially isotonic with a living body. In this case, the radiopharmaceutical is preferably in the form of an aqueous solution, and may contain other pharmaceutically acceptable components as necessary. An effective amount of the radiopharmaceutical is orally or parenterally, for example, intravenously, subcutaneously, intraperitoneally, intramuscularly, or the like, administered to a living body, and is used for treatment of a disease, diagnosis of a disease, detection of a lesion, or the like.

As used herein, the subject of administration is a human, or an animal such as mouse, rat, monkey, guinea pig, chimpanzee, sheep, goat, dog, cat, swine, bovine, horse or the like, but is not particularly limited. Preferred is a human.

As a preferred target disease, cancer can be mentioned. Examples of the cancer to be treated and diagnosed by the present invention include pancreatic cancer, thyroid cancer, liver cancer, colorectal cancer, gastric cancer, urothelial cancer, breast cancer, cervical cancer, ovarian cancer, and endometrial carcinoma, and particularly, application to pancreatic cancer is preferred.

Examples of the cancer to be treated and diagnosed by the present invention also include bile duct cancer.

There are plural reports stating that MUC5AC is an antigen carrier for CA19-9 (PLoS ONE (December 2011, Volume 6, Issue 12, e29180, p1-10)). Therefore, examples of the cancer to be treated by the present invention also include biliary tract cancer, uterine cancer, lung cancer, and esophageal cancer overexpressing CA19-9, and these can be treated efficiency.

As used herein, the "effective amount" is an amount that can afford useful therapeutic effects in a subject of administration. The effective amount to be administered to a subject varies depending on the type of subject, body weight of the subject, dosage form (tablet, injection, etc.) and route (oral administration, parenteral administration, etc.) of administration, severity of disease (e.g., cancer), and the like. Physicians and veterinarians can consider these factors and determine the appropriate effective amount.

By selecting a radionuclide having a therapeutic effect, the conjugate of the present invention can be used for targeted radionuclide therapy (RI internal therapy). In RI internal therapy, a radiopharmaceutical is administered intravenously or orally, this radiopharmaceutical is accumulated in a lesion site such as a primary cancer lesion or a metastatic lesion, and the cancer cells in the lesion site are destroyed by radiation emitted from the radiopharmaceutical. Therefore, the conjugate of the present invention can be preferably used for RI internal therapy of cancer. In this case, the amount of radioactivity to be administered and dose of the pharmaceutical are appropriately selected according to the effectiveness of the active ingredient, the form and route of administration, the stage of progression of the disease (particularly cancer), body shape, body weight, age of the patient, and the kind and amount of other therapeutic agent to be used in combination for the disease. Generally, it can be administered at not more than 250 kBq/kg one time. The effect can be exhibited even at a dose of not more than 80 kBq/kg one time.

In addition, as another embodiment of the present invention, a radiopharmaceutical containing the aforementioned conjugate in which only the radionuclide is replaced with, from the α particle emitting nuclides, a radionuclide ($^{68}$Ga, $^{64}$Cu, $^{86}$Y, $^{89}$Zr, $^{111}$In) that emits positron or γ-ray as the active ingredient may be prepared and used for the diagnosis of cancer in the aforementioned RI internal therapy for cancer. The radioactive drug for cancer diagnosis of the present invention may be used for diagnosis before performing RI internal therapy for cancer, or may be used for diagnosis after performing RI internal therapy for cancer. When used for diagnosis before performing RI internal therapy for cancer, it can be used for the determination of treatment selection of whether to perform RI internal therapy for cancer using the conjugate of the present invention with a metal nuclide that emits α particle. In addition, when used for diagnosis after performing RI internal therapy for cancer, it can be used for the determination of the effect of RI internal therapy for cancer using the conjugate of the present invention with a metal nuclide that emits α particle, and optimization of the treatment plan such as increase or decrease of the dose, and the like.

(2) Conjugate 2

In another embodiment, the present invention provides a conjugate of an antibody and a chelating agent chelated with a radionuclide, wherein the above-mentioned radionuclide is a metal nuclide that emits positron, and the above-mentioned antibody is a humanized antibody specifically binding to MUC5AC.

The same definition as in the above-mentioned "(1) Conjugate 1" applies, except that the radionuclide in the chelating agent is a metal nuclide that emits positron.

Metal nuclide that emits positron may be a nuclide that emits a positively charged electron (positron) in the decay process of the radioactive metal. In detail, $^{68}$Ga, $^{64}$Cu, $^{86}$Y, $^{89}$Zr and the like are preferably used, and more preferred is $^{89}$Zr (zirconium-89). An antibody labeled with a positron-emitting nuclide can be suitably used for PET (Positron Emission Tomography) examinations.

In addition, conjugate 2 using the positron-emitting nuclide as the radionuclide can also be used as a radiopharmaceutical for cancer diagnosis for RI internal therapy using the above-mentioned conjugate 1 using an α particle emitting nuclide as the radionuclide. In this case, the dose of the pharmaceutical is not particularly limited as long as it is an amount necessary and sufficient for depicting the lesion of the disease (particularly cancer) in the PET examination. The dose is preferably selected as appropriate according to the stage of progression of the disease (particularly cancer), body shape, body weight, age of the patient, and the kind and amount of other therapeutic agent to be used in combination for the disease.

According to the embodiment of the present invention described above, an anti-MUC5AC antibody, particularly a humanized antibody, labeled with a radionuclide, particularly an α particle emitting nuclide, which is superior in specificity for MUC5AC and accumulation in tumor is provided.

Moreover, according to the embodiment of the present invention, an RI-labeled anti-MUC5AC antibody which enables cancer diagnosis and/or cancer treatment for achieving theranostics is provided.

The above-mentioned embodiment of the present invention includes the following technical ideas.

[1] A conjugate of an antibody and a chelating agent chelated with a radionuclide, wherein the radionuclide is a metal nuclide emitting a particle, and the antibody is a humanized antibody specifically binding to MUC5AC.

[2] The conjugate of the above-mentioned [1], wherein the antibody is a humanized antibody having a heavy chain variable region consisting of
(1) the amino acid sequence shown in SEQ ID NO: 1 (H01),
(2) the amino acid sequence shown in SEQ ID NO: 2 (H02),
(3) the amino acid sequence shown in SEQ ID NO: 3 (H03), or
(4) the amino acid sequence shown in SEQ ID NO: 4 (H04), and
a light chain variable region consisting of
(5) the amino acid sequence shown in SEQ ID NO: 5 (L01),
(6) the amino acid sequence shown in SEQ ID NO: 6 (L02),
(7) the amino acid sequence shown in SEQ ID NO: 7 (L03), or
(8) the amino acid sequence shown in SEQ ID NO: 8 (L04).

[3] The conjugate of the above-mentioned [2], wherein the antibody is a humanized antibody having
(1) a heavy chain variable region consisting of the amino acid sequence shown in SEQ ID NO: 1 (H01), and
(7) a light chain variable region consisting of the amino acid sequence shown in SEQ ID NO: 7 (L03).

[4] The conjugate of any of the above-mentioned [1] to [3], wherein the metal nuclide emitting a particle is actinium-225.

[5] The conjugate of any of the above-mentioned [1] to [4], comprising not less than 1 molecule and not more than 8 molecules of the chelating agent per 1 molecule of the antibody.

[6] The conjugate of any of the above-mentioned [1] to [5], wherein the chelating agent site-specifically modifies an Fc region of the antibody via a linker.

[7] The conjugate of the above-mentioned [6], wherein the linker comprises an antibody-modification peptide consisting of not less than 13 and not more than 17 amino acid residues, and represented by the following formula (i);

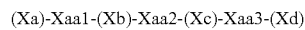

(Xa)-Xaa1-(Xb)-Xaa2-(Xc)-Xaa3-(Xd)     (i)

wherein Xa, Xb, Xc and Xd are each continuous X in the number of a, continuous X in the number of b, continuous X in the number of c, and continuous X in the number of d, respectively, X is an amino acid residue having neither a thiol group nor a haloacetyl group in the side chain, a, b, c and d are each independently an integer of not less than one and not more than 5, and satisfy a+b+c+d≤14, Xaa1 and Xaa3 are each independently an amino acid residue derived from an amino acid having a thiol group in the side chain, and they are linked via a disulfide bond or their sulfide groups are linked via a linker, or one is an amino acid residue derived from an amino acid having a thiol group in the side chain and the other is an amino acid residue derived from an amino acid having a haloacetyl group in the side chain, and they are linked via a thioether bond, and Xaa2 is a lysine residue, arginine residue, cysteine residue, aspartic acid residue, glutamic acid residue, 2-aminosuberic acid, or diamino propionic acid.

[8] The conjugate of the above-mentioned [7], wherein the antibody-modification peptide is the formula (i) wherein Xaa2 is a lysine residue.

[9] The conjugate of the above-mentioned [7] or [8], wherein the antibody-modification peptide comprises an antibody-modification peptide consisting of the amino acid sequence shown in SEQ ID NO: 10 (wherein Xaa2 is a lysine residue).

[10] The conjugate of any of the above-mentioned [1] to [9], wherein the chelating agent has a structure derived from a compound represented by the following formula (A) or a salt thereof:

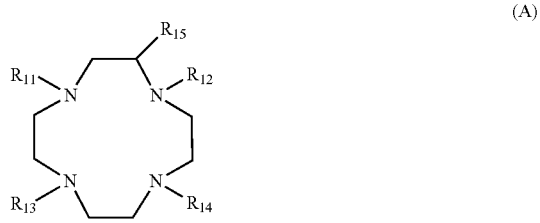

(A)

wherein in the formula (A), $R_{11}$, $R_{13}$ and $R_{14}$ are each independently a group consisting of —$(CH_2)_p$COOH, —$(CH_2)_p C_5 H_5 N$, —$(CH_2)_p PO_3 H_2$, —$(CH_2)_p CONH_2$ or —(CHCOOH)$(CH_2)_p$COOH, one of $R_{12}$ and $R_{15}$ is a hydrogen atom, a carboxyl group, or a carboxyalkyl group having 2 or 3 carbon atoms, the other is a substituent for conjugating with the antibody, p is an integer of not less than 0 and not more than 3, $R_{15}$ is a hydrogen atom when $R_{12}$ is a substituent for conjugating with the antibody, and $R_{15}$ is a substituent for conjugating with the antibody when $R_{12}$ is not a substituent for conjugating with the antibody.

[11] The conjugate of any of the above-mentioned [6] to [10], wherein the chelating agent site-specifically modifies an Fc region of the antibody via a linker, the linker has a connected group formed by a click reaction.

[12] The conjugate of the above-mentioned [11], wherein the linker has a chelate linker connecting the chelating agent and the connected group formed by the click reaction, and an antibody-modification linker connecting the antibody and the connected group formed by the click reaction, and the connected group formed by the click reaction comprises a triazole skeleton-containing structure represented by the following formula (10a) or a pyridazine skeleton-containing structure:

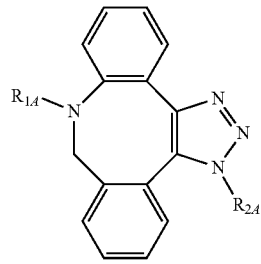

(10a)

wherein $R_{1A}$ is a binding site with the chelate linker, and $R_{2A}$ is a binding site with the antibody-modification linker.

[13] A radioactive drug comprising the conjugate of any of the above-mentioned [1] to [12] as the active ingredient.

[14] The radioactive drug of the above-mentioned [13] that is used for RI internal therapy for cancer.

[15] The radioactive drug of the above-mentioned [14] that is administered to a subject at a dose of not more than 250 kBq/kg one time in RI internal therapy.

[16] The radioactive drug of the above-mentioned [15], wherein the dose is not more than 80 kBq/kg one time.

[17] A radioactive drug for cancer diagnosis in RI internal therapy using the radioactive drug of any of the above-mentioned [14] to [16], wherein the drug is a radioactive drug comprising a conjugate of an antibody and a chelating agent chelated with a radionuclide, and the antibody is a humanized antibody specifically binding to MUC5AC.

[18] A conjugate of an antibody and a chelating agent chelated with a radionuclide, wherein the radionuclide is a metal nuclide emitting positron, and the antibody is a humanized antibody specifically binding to MUC5AC.

[19] The conjugate of the above-mentioned [18], wherein the antibody is a humanized antibody having a heavy chain variable region consisting of (1) the amino acid sequence shown in SEQ ID NO: 1 (H01),
(2) the amino acid sequence shown in SEQ ID NO: 2 (H02),
(3) the amino acid sequence shown in SEQ ID NO: 3 (H03), or
(4) the amino acid sequence shown in SEQ ID NO: 4 (H04), and a light chain variable region consisting of
(5) the amino acid sequence shown in SEQ ID NO: 5 (L01),
(6) the amino acid sequence shown in SEQ ID NO: 6 (L02),
(7) the amino acid sequence shown in SEQ ID NO: 7 (L03), or
(8) the amino acid sequence shown in SEQ ID NO: 8 (L04).

[20] The conjugate of the above-mentioned [19], wherein the antibody is a humanized antibody having (1) a heavy chain variable region consisting of the amino acid sequence shown in SEQ ID NO: 1 (H01), and
(7) a light chain variable region consisting of the amino acid sequence shown in SEQ ID NO: 7 (L03).

[21] The conjugate of any of the above-mentioned [18] to [20], wherein the metal nuclide emitting positron is zirconium-89.

[22] The conjugate of any of the above-mentioned [18] to [21], comprising 1-8 molecules of the chelating agent per 1 molecule of the antibody.

[23] The conjugate of any of the above-mentioned [18] to [21], wherein the chelating agent site-specifically modifies an Fc region of the antibody via a linker.

[24] The conjugate of the above-mentioned [23], wherein the linker comprises an antibody-modification peptide consisting of not less than 13 and not more than 17 amino acid residues, and represented by the following formula (i);

(Xa)-Xaa1-(Xb)-Xaa2-(Xc)-Xaa3-(Xd)  (i)

wherein Xa, Xb, Xc and Xd are each continuous X in the number of a, continuous X in the number of b, continuous X in the number of c, and continuous X in the number of d, respectively, X is an amino acid residue having neither a thiol group nor a haloacetyl group in the side chain, a, b, c and d are each independently an integer of not less than one and not more than 5, and satisfy a+b+c+d≤14, Xaa1 and Xaa3 are each independently an amino acid residue derived from an amino acid having a thiol group in the side chain, and they are linked via a disulfide bond or their sulfide groups are linked via a linker, or one is an amino acid residue derived from an amino acid having a thiol group in the side chain and the other is an amino acid residue derived from an amino acid having a haloacetyl group in the side chain, and they are linked via a thioether bond, and Xaa2 is a lysine residue, arginine residue, cysteine residue, aspartic acid residue, glutamic acid residue, 2-aminosuberic acid, or diamino propionic acid.

[25] The conjugate of the above-mentioned [24], wherein the antibody-modification peptide is the formula (i) wherein Xaa2 is a lysine residue.

[26] The conjugate of the above-mentioned [24] or [25], wherein the antibody-modification peptide comprises an antibody-modification peptide consisting of the amino acid sequence shown in SEQ ID NO: 10 (wherein Xaa2 is a lysine residue).

[27] The conjugate of any of the above-mentioned [18] to [26], wherein the chelating agent has a structure derived from a compound represented by the following formula (A) or a salt thereof:

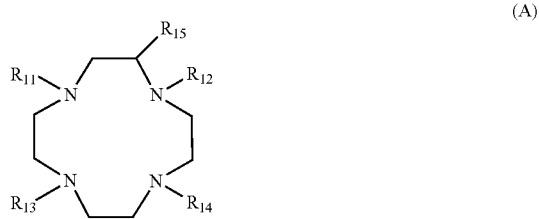

(A)

wherein in the formula (A), $R_{11}$, $R_{13}$ and $R_{14}$ are each independently a group consisting of —$(CH_2)_p COOH$, —$(CH_2)_p C_5H_5N$, —$(CH_2)_p PO_3H_2$, —$(CH_2)_p CONH_2$ or —$(CHCOOH)(CH_2)_p COOH$, one of $R_{12}$ and $R_{15}$ is a hydrogen atom, a carboxyl group, or a carboxyalkyl group having 2 or 3 carbon atoms, the other is a substituent for conjugating with the antibody, p is an integer of not less than 0 and not more than 3, $R_{15}$ is a hydrogen atom when $R_{12}$ is a substituent for conjugating with the antibody, and $R_{15}$ is a substituent for conjugating with the antibody when $R_{12}$ is not a substituent for conjugating with the antibody.

[28] A radioactive drug comprising the conjugate of any of the above-mentioned [18] to [27] as the active ingredient.

[29] A method for producing the conjugate of any of the above-mentioned [1] to [12] and [18] to [27], comprising a conjugating step of conjugating a chelating agent chelated with a radionuclide and an anti-MUC5AC antibody to produce a conjugate of the chelating agent and the anti-MUC5AC antibody.

[30] The production method of the above-mentioned [29], wherein the chelating agent is connected to a chelate linker, the anti-MUC5AC antibody has an Fc region specifically modified by an antibody-modification linker provided with an antibody-modification peptide, and the chelate linker and the antibody-modification linker are connected by performing a click reaction in the conjugating step.

[31] A modified antibody with an Fc region of the antibody specifically modified by an antibody-modification linker provided with an antibody-modification peptide, wherein the antibody is an anti-MUC5AC antibody, and the antibody-modification linker has an atomic group to connect to a chelate linker of a chelating agent chelated with a radionuclide by a click reaction.

[32] A method for producing a modified antibody in which an Fc region of the antibody is specifically modified by an antibody-modification linker provided with an antibody-modification peptide, comprising an antibody modification step of site-specifically modifying an Fc region of the antibody with a linker provided with an antibody-modification peptide to give a modified antibody, and an antibody purification step of purifying the antibody using a carrier with an immunoglobulin-binding protein immobilized thereon, wherein the antibody is an anti-MUC5AC antibody.

[33] The production method of the above-mentioned [32], wherein the immunoglobulin-binding protein is protein A or genetically-engineered protein A.

[34] The production method of the above-mentioned [32] or [33], wherein the antibody purification step is performed using a column filled with the carrier.

[35] The production method of any of the above-mentioned [32] to [34], wherein the antibody purification step comprises a retention step of retaining the modified antibody on the carrier, and an elution step of eluting the modified antibody retained on the carrier.

[36] The production method of the above-mentioned [35], wherein the modified antibody is obtained as a mixture containing an unmodified antibody not modified by the antibody-modification linker, a monovalent antibody modified by one molecule of the antibody-modification linker with respect to one molecule of the antibody, and a divalent antibody modified by two molecules of the antibody-modification linker with respect to one molecule of the antibody in the antibody modification step, and a first antibody composition containing relatively large amounts of the unmodified antibody and the monovalent antibody and a second antibody composition containing a relatively large amount of the divalent antibody are respectively obtained utilizing the difference in the interaction of the unmodified antibody, the monovalent antibody and the divalent antibody with immunoglobulin-binding proteins in the antibody purification step.

[37] A method for producing a conjugate, comprising a modified antibody production step of performing the production method of any of the above-mentioned [32] to [36] to obtain a modified antibody, and a conjugating step of conjugating the modified antibody and a chelating agent chelated with a radionuclide to produce a conjugate of the chelating agent and the modified antibody.

[38] The production method of the above-mentioned [37], wherein the first antibody composition in which the proportion of a total of the unmodified antibody not modified by the antibody-modification linker and the monovalent antibody modified by one molecule of the antibody-modification linker with respect to one molecule of the antibody is larger than the divalent antibody modified by two molecules of the antibody-modification linker with respect to one molecule of the antibody is obtained in the modified antibody production step, and the conjugate of the chelating agent and the monovalent antibody is formed in the conjugating step.

[39] The production method of the above-mentioned [37], wherein the second antibody composition in which the proportion of the divalent antibody modified by two molecules of the antibody-modification linker with respect to one molecule of the antibody is larger than a total of the unmodified antibody not modified by the antibody-modification linker and the monovalent antibody modified by one molecule of the antibody-modification linker with respect to one molecule of the antibody is obtained in the modified antibody production step, and the conjugate of the chelating agent and the divalent antibody is formed in the conjugating step.

[40] The production method of any of the above-mentioned [37] to [39], wherein the chelating agent is connected to the chelate linker, and the chelate linker and the antibody-modification linker are connected by performing the click reaction in the conjugating step.

[41] A kit for producing a conjugate of an antibody and a chelating agent chelated with a radionuclide, comprising (1) a chelating agent capable of chelating a radionuclide and (2) an anti-MUC5AC antibody, wherein the conjugate is the conjugate of any of the above-mentioned [1] to [12] and [18] to [27].

[42] The kit of [41], further comprising (1) a first atomic group capable of click reaction and (2) a second atomic group capable of click reaction.

[43] The kit of [41], further comprising a radionuclide capable of chelating with the chelating agent.

According to the radiopharmaceutical of the above-mentioned [14], since a conjugate containing a humanized antibody specifically binding to MUC5AC and a metal nuclide that emits α particle is contained as an active ingredient, when used for RI internal therapy of cancer, it accumulates specifically in tumor expressing MUC5AC, and can irradiate α particle specifically on tumor cells without affecting normal cells, whereby higher safety and higher therapeutic effect are obtained.

According to the radiopharmaceutical of the above-mentioned [28], since it contains a conjugate containing a humanized antibody specifically binding to MUC5AC and a metal nuclide that emits positron as an active ingredient, it is suitable for PET examination. In addition, since it exhibits the same accumulation property as the radiopharmaceutical used for RI internal therapy of the above-mentioned [14], it can be efficiently used as a diagnostic radiopharmaceutical for RI internal therapy of cancer expressing MUC5AC.

According to the above-mentioned method for producing a conjugate of the above-mentioned [29], since it includes a conjugate formation step of conjugating a chelating agent chelated with a radionuclide and an anti-MUC5AC antibody, the conjugate can be efficiently obtained by preventing denaturation of the antibody without subjecting the anti-MUC5AC antibody to a chelating step, which is a more severe condition for the antibody.

According to the method for producing a conjugate of the above-mentioned [30], since the click reaction is included in the conjugate formation step, the conjugate can be formed in a buffer solution under extremely mild condition of room temperature, and the conjugate can be obtained efficiently without denaturing the anti-MUC5AC antibody.

According to the modified antibody of the above-mentioned [31], since the Fc region of the anti-MUC5AC antibody is specifically modified by the antibody-modification linker, the modified antibody can be used in a click reaction with respect to a chelating agent chelated with a radionuclide, without impairing the antigen-binding ability of the anti-MUC5AC antibody.

According to the method for producing a modified antibody according to the above-mentioned [32], since it includes an antibody modification step of site-specifically modifying the Fc region of an anti-MUC5AC antibody with a linker provided with an antibody-modification peptide to obtain a modified antibody, and an antibody purification step of purifying the aforementioned antibody by using a carrier with an immunoglobulin-binding protein immobilized thereon, the purity of the modified antibody can be further increased.

According to the method for producing a conjugate of the above-mentioned [38] or [39], since the conjugate formation step is performed using an antibody conjugate in which the proportion of either the monovalent antibody or the divalent antibody is higher than the proportion of the other, the number of chelating agents that bind to the anti-MUC5AC antibody can be adjusted according to the purpose, and a conjugate having a desired valence can be obtained with higher purity.

According to the kit of the above-mentioned [41], since the conjugate of any of [1] to [12] and [18] to [27] can be prepared at the time of use by reacting a conjugate of a chelating agent capable of chelating a radionuclide and an antibody with the radionuclide at a required timing, efficient treatment or diagnosis is possible without impairing both the half-life of the radionuclide and antibody activity.

According to the kit of the above-mentioned [42], since a conjugate containing a chelating agent capable of chelating a radionuclide and an atomic group for click reaction and a conjugate containing an antibody and an atomic group for click reaction are separately provided, the conjugate of any of [1] to [12] and [18] to [27] can be prepared at the time of use by chelating the radionuclide with a chelating agent and click reaction thereof at a required timing, and efficient treatment or diagnosis is possible without impairing both the half-life of the radionuclide and antibody activity.

The present invention is explained in detail in the following by referring to Examples and the like. The present invention is not limited thereto.

EXAMPLE

Production Example 1: Production of Anti-MUC5AC Humanized Antibody

The amino acid sequences of various variable regions to which a signal sequence was added and the amino acid sequences of various constant regions were converted into base sequences while considering codon usage suitable for expression in CHO cells. A Kozak sequence was added to the initiation codon site of the signal sequence, and a stop codon was added to the C-terminal side of the constant region. Furthermore, restriction enzyme sites were added to the upstream of the Kozak sequence and downstream of the stop codon so that they could be introduced into the expression gene transfer site of a mammalian cell expression plasmid (pcDNA3.4). Each DNA fragment designed in this way was prepared by chemical synthesis. A DNA fragment containing a variable region to be a desired H chain and a desired L chain and a DNA fragment containing a constant region were ligated by fusion PCR.

The prepared various antibody genes were subjected to restriction enzyme treatment and then purified. Similarly, a mammalian cells transient expression plasmid (pcDNA3.4) was also treated with the same restriction enzyme and then purified. The both fragments were mixed at an appropriate mixing ratio and ligated. The ligation reaction solution was mixed with *Escherichia coli* DH5α competent cells to perform transformation. The resulting transformants were subjected to colony PCR, single colony isolation, plasmid extraction from small-scale culture medium, and nucleotide sequencing of the insert portion were performed. A plasmid (*Escherichia coli* clone) into which the full-length designed antibody gene was correctly inserted in the intended direction with the designed sequence (*Escherichia coli* clone) was selected. The selected *Escherichia coli* clone was subjected to large scale culture, and plasmid extraction and purification including an endotoxin removal step were performed. The concentration of the purified plasmid was calculated by measuring the absorbance at 260 nm.

1 (SEQ ID NO: 25) and light chain constant region 1 (SEQ ID NO: 26), and the heavy chain variable region and light chain variable region of the above-mentioned antibody 1 to antibody 4.

Production Example 2: Site-Specific Antibody Modification by Peptide Linker (1) Antibody Modification Step An antibody-modification peptide was produced by the method described in WO 2017/217347 to obtain a peptide containing 17 amino acid residues represented by the following formula (P3). The amino acid sequence of this peptide was the same as the sequence in which Xaa2 of SEQ ID NO: 10 was a lysine residue, and the side chain terminal amino group of the lysine residue was modified with the structure shown by $R_1$. In addition, two cysteine residues form a disulfide bond with each other, and to the N-terminal of the peptide is added ethyl azide as an atomic group containing an azide group, which is the second atomic group, via a linker structure having diglycolic acid and eight PEGs.

(P3)

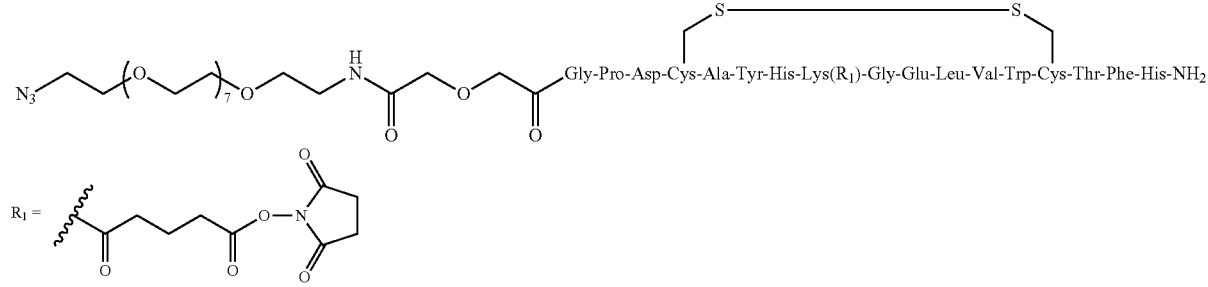

Transient expression by CHO cells was performed using the ExpiCHO System (Thermo Fisher Scientific). From each of the prepared H chain expression plasmids and each of the prepared L chain expression plasmid, one H chain and one L chain were selected to achieve the desired combination, transfected by the lipofection method, cultured, and fed. After 7 days-13 days from transfection, the culture medium was recovered. The culture supernatants after centrifugation and filtration were added to Protein A column and the antibody was purified by general affinity column chromatography (washing after adsorption, elution with acidic buffer, neutralization of eluate). The concentration of the purified antibody was calculated by measuring the absorbance at 280 nm.

The following anti-MUC5AC humanized antibodies were prepared using the method described above. The antibody numbers assigned to the combinations of the heavy chain variable region and the light chain variable region are shown below.
antibody 1: H01L03
antibody 2: H01L04
antibody 3: H02L04
antibody 4: H04L04

As used herein, H01, H02 and H04 are heavy chain variable regions respectively shown in SEQ ID NO: 1, SEQ ID NO: 2 and SEQ ID NO: 4, L03 and L04 are light chain variable regions respectively shown in SEQ ID NO: 7 and SEQ ID NO: 8. The antibodies used in the following Examples were combinations of heavy chain constant region (in the formula (P3), Gly is glycine, Pro is proline, Asp is aspartic acid, Cys is cysteine, Ala is alanine, Tyr is tyrosine, His is histidine, Glu is glutamic acid, Leu is leucine, Val is valine, Trp is tryptophan, Phe is phenylalanine.)

A mixture of the peptide and an anti-MUC5AC humanized antibody (antibody 1) produced in Production Example 1 in a sodium acetate buffer (pH 6.0) was reacted at room temperature for 30 min to give a solution containing a peptide-modified antibody. The peptide-modified antibody has an Fc region of the antibody site-specifically modified by the above-mentioned peptide.

(2) Peptide-Modified Antibody Separation Step

The peptide-modified antibody was diluted with 1 mol/L sodium acetate buffer (pH 6.0), added to Protein A column (manufactured by GE Healthcare, HiTrap MabSelect SuRe), and a 0.05 mol/L sodium acetate buffer (pH 5.7) containing 0.15 mol/L sodium chloride was flown. A peptide-modified antibody (hereinafter to be also referred to as "divalent antibody") to which two peptide molecules modify was recovered, and the concentration was adjusted such that the concentration of the divalent antibody contained in the recovered fraction was 15 mg/mL. Thereafter, 0.05 mol/L sodium acetate buffer (pH 3.5) containing 0.15 mol/L sodium chloride was flown, a peptide-modified antibody (hereinafter to be also referred to as "monovalent antibody") to which one molecule of peptide modify was recovered, and the concentration was adjusted such that the concentration of the monovalent antibody contained in the recovered fraction was 15 mg/mL.

Example 1: Production of $^{225}$Ac-Labeled Anti-MUC5AC Humanized Antibody ($^{225}$Ac-Labeled Monovalent Antibody)—1

(1) Chelating Agent Synthesis Step

The structure of the chelate site (manufactured by Iris Biotech GmbH) used in this Example is shown in the following formula (L1-3). The chelate site was dissolved in 0.1 mol/L sodium acetate buffer (pH 6.0) as a solvent to give a solution containing 1.7 mmol/L chelate site. A reaction mixture of the solution (0.005 mL), and $^{225}$Acion-containing solution (0.2 mol/L aqueous hydrochloric acid solution, radioactivity concentration 300 MBq/mL, prepared from one produced by Oak Ridge National Laboratory, liquid amount: 0.005 mL) 1.5 MBq (calculated by attenuation from the amount of radioactivity at test date and time) as a source of radioactive metal was reacted under heating conditions to give a $^{225}$Ac complex solution. The molar ratio of the chelate site and the radioactive metal ion was chelate site:$^{225}$Ac ion=about 2000:1, and the heating temperature of the reaction mixture was set to 70° C., and the heating time was set to 90 min.

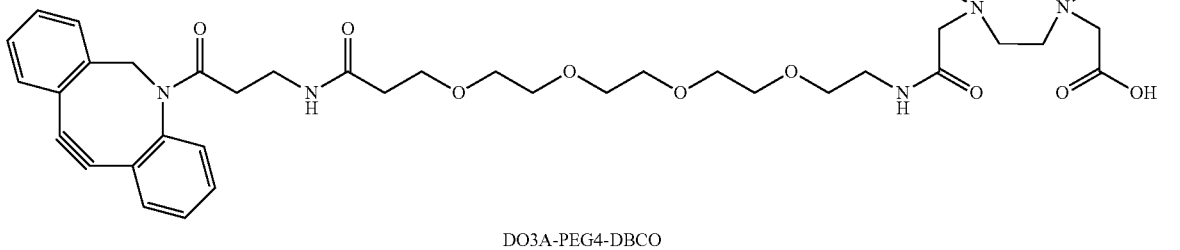

(L1-3)

DO3A-PEG4-DBCO

The radiochemical purity of the obtained $^{225}$Ac complex was measured by the following method. That is, a part of the $^{225}$Ac complex solution was developed by thin layer chromatography (manufactured by Agilent, model number: SGI0001, developing solvent: acetonitrile/water mixed solution (volume ratio 1:1)), and then measured by radio γ-TLC Analyzer (manufactured by raytest, MODEL GITA Star). The percentage of the radioactivity (count) of the peak detected near the origin with respect to the detected total radioactivity (count) was defined as the radiochemical purity (%) of the $^{225}$Ac complex. As a result, the radiochemical purity of the $^{225}$Ac complex was 86%. The obtained $^{225}$Ac complex solution was directly used for the next labeling step.

(2) Radiolabeling Step

The eluate of the monovalent antibody obtained in Production Example 2, and the solution of the $^{225}$Ac complex obtained in the aforementioned step (1) were each added to 0.02 mol/L (20 mM) ascorbic acid-containing 0.09 mol/L sodium acetate buffer, and click reacted at 37° C. for 120 min to give an $^{225}$Ac-labeled monovalent antibody. The amount of the $^{225}$Ac complex and the amount of the peptide-modified antibody were 44 μmol and 46 μmol, respectively, and the molar ratio of the first atomic group (DBCO) and the second atomic group (azide) was about 1:1.

Furthermore, a solution of the $^{225}$Ac-labeled monovalent antibody obtained by reacting at 37° C. for 2 hr was purified using ultrafiltration filter (manufactured by Merck, model number: UFC505096), and subjected to the subsequent experiments. The radiochemical purity of the $^{225}$Ac-labeled monovalent antibody after purification (amount of radioactivity calculated by attenuation from the amount of radioactivity at test date and time: 0.303 MBq) was 93%, and the radiochemical yield was 39%. As used herein, the radiochemical purity is the ratio (%) of the radioactivity count of the peak corresponding to the $^{225}$Ac-labeled monovalent antibody to the total radioactivity count of the thin layer plate when analyzed by thin layer chromatography, and the radiochemical yield is the ratio (%) of the radioactivity amount calculated from the radioactivity count of the $^{225}$Ac-labeled monovalent antibody to the radioactivity amount calculated from the radioactivity count at the start of the aforementioned step (1) measured by γ-ray spectrometer (Ge semiconductor detector: GMX10P4-70 (manufactured by ORTEC), Multi Channel Analyzer: M7-000 (manufactured by SEIKO EG&G), data processing: Spectrum Navigator: DS-P300 (manufactured by SEIKO EG&G) and Gamma Studio: DS-P600 (manufactured by SEIKO EG&G)).

Example 2: Production of $^{225}$Ac-Labeled Anti-MUC5AC Humanized Antibody ($^{225}$Ac-Labeled Monovalent Antibody)—2

(1) Chelating Agent Synthesis Step

The structure of the chelate site used in this Example is shown in the following formula (L1-4). DOTA-Bn-DBCO shown by the formula (L1-4) was produced according to the method described in Wang H, Wang R, Cai K, He H, Liu Y, Yen J et al. Selective in vivo metabolic cell-labeling-mediated cancer targeting. Nat Chem Biol. April; 13(4): 415-424. (2017). The chelate site was dissolved in 0.1 mol/L sodium acetate buffer (pH 6.0) as a solvent to give a solution containing 1.7 mmol/L chelate site. A reaction mixture of the solution (0.0025 mL), and $^{225}$Ac ion-containing solution (0.2 mol/L aqueous hydrochloric acid solution, radioactivity concentration 432 MBq/mL, manufactured by Oak Ridge National Laboratory, liquid amount: 0.0025 mL) 1.08 MBq (calculated by attenuation from the amount of radioactivity at test date and time) as a source of radioactive metal, and 0.1 mol/L sodium acetate buffer (pH 6.0, 0.0375 mL) was reacted under heating conditions to give a $^{225}$Ac complex solution. The molar ratio of the chelate site and the radioactive metal ion was chelate site:$^{225}$Ac ion=about 2000:1, and the heating temperature of the reaction mixture was set to 70° C., and the heating time was set to 90 min.

the radioactivity count at the start of the aforementioned step (1) measured by γ-ray spectrometer (Ge semiconductor detector: GMX10P4-70 (manufactured by ORTEC), Multi Channel Analyzer: M7-000 (manufactured by SEIKO EG&G), data processing: Spectrum Navigator: DS-P300 (manufactured by SEIKO EG&G) and Gamma Studio: DS-P600 (manufactured by SEIKO EG&G)).

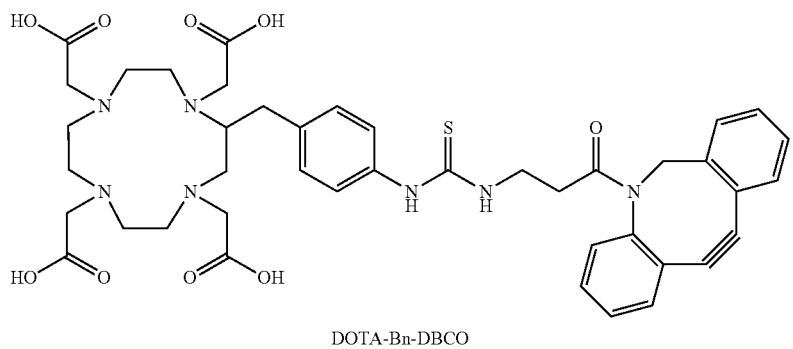

DOTA-Bn-DBCO

The radiochemical purity of the obtained $^{225}$Ac complex was measured by the following method. That is, a part of the $^{225}$Ac complex solution was developed by thin layer chromatography (manufactured by Agilent, model number: SGI0001, developing solvent: acetonitrile/water mixed solution (volume ratio 1:1)), and then measured by radio γ-TLC Analyzer (manufactured by raytest, MODEL GITA Star). The percentage of the radioactivity (count) of the peak detected near the origin with respect to the detected total radioactivity (count) was defined as the radiochemical purity (%) of the $^{225}$Ac complex. As a result, the radiochemical purity of the $^{225}$Ac complex was 98%. The obtained $^{225}$Ac complex solution was directly used for the next labeling step.

(2) Radiolabeling Step

The eluate of the monovalent antibody obtained in Production Example 2, and the solution of the $^{225}$Ac complex obtained in the aforementioned step (1) were each click reacted at 37° C. for 120 min to give an $^{225}$Ac-labeled monovalent antibody. The amount of the $^{225}$Ac complex and the amount of the peptide-modified antibody were 44 µmol and 46 µmol, respectively, and the molar ratio of the first atomic group (DBCO) and the second atomic group (azide) was about 1:1.

Furthermore, to a solution of the $^{225}$Ac-labeled monovalent antibody obtained by reacting at 37° C. for 120 min was added 20 mmol/L ascorbic acid-containing 90 mmol/L sodium acetate buffer (pH 6.0), and the mixture was purified using ultrafiltration filter (manufactured by Merck, model number: UFC505096), and subjected to the subsequent experiments. The radiochemical purity of the $^{225}$Ac-labeled monovalent antibody after purification (amount of radioactivity calculated by attenuation from the amount of radioactivity at test date and time: 0.231 MBq) was 86%, and the radiochemical yield was 21%. As used herein, the radiochemical purity is the ratio (%) of the radioactivity count of the peak corresponding to the $^{225}$Ac-labeled monovalent antibody to the total radioactivity count of the thin layer plate when analyzed by thin layer chromatography, and the radiochemical yield is the ratio (%) of the radioactivity amount calculated from the radioactivity count of the $^{225}$Ac-labeled antibody to the radioactivity amount calculated from Example 3: Production of $^{225}$Ac-Labeled Anti-MUC5AC Humanized Antibody ($^{225}$Ac-Labeled Divalent Antibody)

In the same manner as in Example 2 except that an eluate of the divalent antibody obtained in Production Example 2 was used instead of the eluate of the monovalent antibody, an $^{225}$Ac-labeled divalent antibody was obtained. The obtained radiochemical purity of the $^{225}$Ac-labeled divalent antibody (amount of radioactivity calculated by attenuation from the amount of radioactivity at test date and time: 0.168 MBq) was 99%, and the radiochemical yield was 20%.

Example 4: Screening of Humanized Antibody Using In-111($^{111}$In)-Labeled Antibody Example 4-1: Preparation of $^{111}$In-Labeled Antibody To find an anti-MUC5AC antibody with high tumor accumulation ability and high maximum tolerated dose, various antibodies were labeled with $^{111}$In, administered to tumor-bearing mice, and SPECT-CT imaging was performed. Cumulative amount of radioactivity and absorbed dose were calculated and compared using the obtained images.

The antibody used were 4 types of anti-MUC5AC humanized antibodies prepared in Production Example 1 and 1 type of anti-MUC5AC chimeric antibody disclosed in patent document 1, and they were labeled with $^{111}$In.

The amino acid sequences of the heavy chain variable region and the light chain variable region (SEQ ID NOs: 23 and 24, respectively) of the chimeric antibody disclosed in patent document 1 are as follows.

The $^{111}$In labeling was performed on complexes of a labeling precursor having a structure represented by the following formula and various antibodies.

[heavy chain variable region]
E V K L V E S G G V L V K S G G S L K L S C A

V S G F T F S N Y G M S W V R Q T P E K R L E

-continued

```
W V A T I S N S G R Y T Y F P D S V K G P F A

I S R D N A K N M L Y L Q M S S L R S A D T A

L Y Y C T R H L D Y A N Y D A M D Y W G Q G T

S V T V S S

[light chain variable region]
D I Y L T Q S P A S L A V S L G Q R A T I S C

R A S K S V T T S D F S Y M H W Y Q Q K P G Q

P P K L L L Y L A S N L E S G V P D R F S G S

G S G Y D F Y L N I H P V E E E D A A T Y Y C

Q H S R E F P W T F G G G T K L E I K
```

$^{111}$In-labeled antibodies are shown in Table 1. The radiochemical yield here refers to the amount of radioactivity of the $^{111}$In-labeled antibody with respect to the amount of radioactivity of $^{111}$In used. For the radioactivity measurement, a radioisotope Doze Calibrator (manufactured by CAPINTEC, model number: CRC-15R) was used. The radiochemical purity refers to the ratio (%) of the peak radioactivity count corresponding to the $^{111}$In-labeled antibody to the total radioactivity count of the filter paper as analyzed by filter paper chromatography. For filter paper chromatography, filter: manufactured by ADVANTEC, model number: No. 590, developing solvent: 0.01% EDTA, 50 mM citric acid-sodium citrate aqueous solution) was developed, and the radioactivity count was detected using a radio γ-TLC analyzer (manufactured by raytest, MODEL GITA Star).

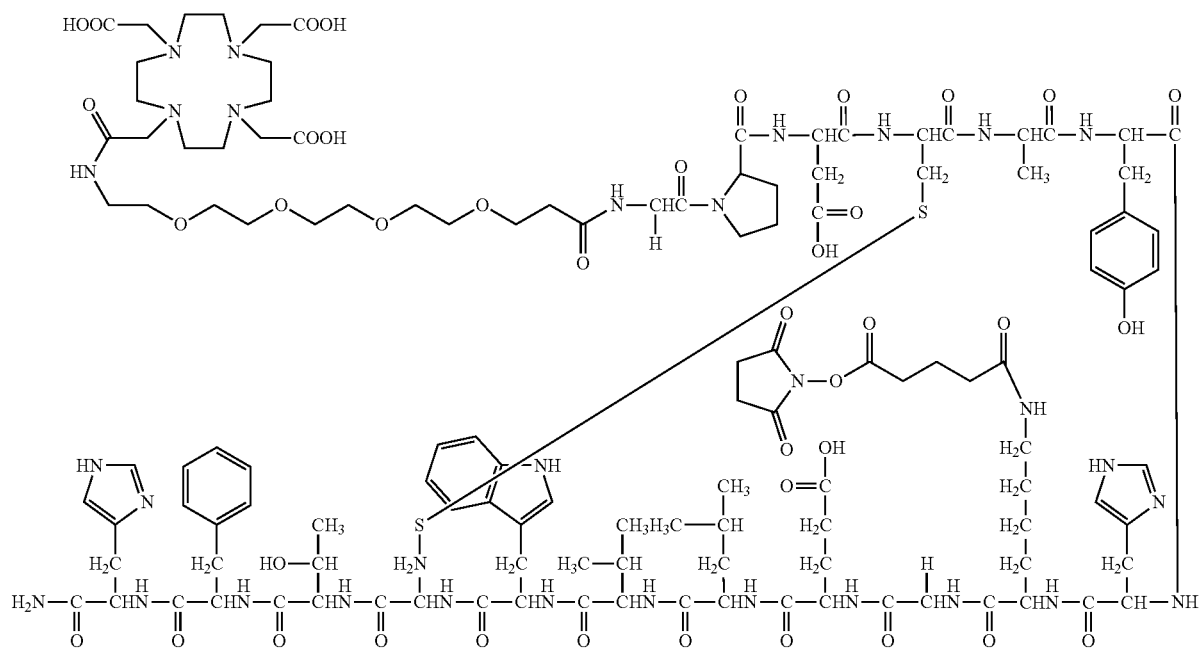

The above-mentioned labeled precursor had a structure in which DOTA as a chelate site is linked to the N-terminal of an antibody-modification peptide (peptide containing 17 amino acid residues having the same sequence as the sequence of SEQ ID NO: in which Xaa2 is a lysine residue) via 8 polyethylene glycols, and linked to the 252nd lysine residue by EU numbering in various antibodies via an N-hydroxysuccinimidoester group in the structure.

This labeled precursor (450 µg) was dissolved in 4-(2-hydroxyethyl)-1-piperazine ethanesulfonic acid buffer (pH 5.5) as a solvent at 100 mmol/L. This solution was mixed with a $^{111}$In ion-containing solution (indium ($^{111}$In) chloride Injection, manufactured by Nihon Medi-Physics Co., Ltd.) as a radioactive metal source at 10 MBq as a radioactive amount, and a labeling reaction was performed at 45° C. for 120 min.

The radiochemical yield, radiochemical purity, and amount of radioactivity administered to animal of various

TABLE 1

| | $^{111}$In labeling information | | | | |
|---|---|---|---|---|---|
| name of antibody | chimeric antibody | humanized antibody | | | |
| | | H01L03 | H01L04 | H02L04 | H04L04 |
| radiochemical yield (%) | 99.0 | 96.3 | 93.6 | 91.0 | 94.0 |
| radiochemical purity (%) | | | 100 | | |
| administered radioactivity amount (MBq) | 5.3 ± 1.0 | 5.5 ± 0.1 | 4.7 ± 0.2 | 4.6 ± 0.2 | 4.6 ± 1.3 |

(mean ± standard deviation, n = 4)

Example 4-2: Biodistribution Using Tumor-Bearing Mice (Production Method of Tumor-Bearing Mouse)

Human pancreatic cancer cell line SW1990 (0.7×10$^7$ cells) were subcutaneously administered to Balb/c nude mice (male) from the flank to the back thereof.

When the tumor size reached about 150-300 mm³ 14 days after transplantation of SW1990, various ¹¹¹In-labeled antibodies prepared in Example 4-1 were administered from the tail vein of the mice. The tumor volume was calculated from the following calculation formula.

tumor volume=(tumor minor axis²×tumor major axis)/2

TABLE 2

Animal information (on administration of each ¹¹¹In-labeled antibody)

| name of antibody | chimeric antibody | humanized antibody | | | |
|---|---|---|---|---|---|
| | | H01L03 | H01L04 | H02L04 | H04L04 |
| tumor volume (mm³) | 203 ± 110 | 201 ± 45 | 285 ± 24 | 209 ± 83 | 193 ± 80 |
| body weight (g) | 23.2 ± 1.3 | 23.4 ± 0.6 | 23.5 ± 0.7 | 22.1 ± 1.7 | 21.2 ± 1.8 |

(mean ± standard deviation, n = 4)

(Evaluation Method)

SPECT-CT imaging (small animal SPECT-CT apparatus: FX-3000, manufactured by Trifoil) was performed under the conditions in the following Table. The time points for imaging were 1, 6, 24, 48, 72, and 168 hr after administration. Image reconstruction was performed by the OSEM method for SPECT and the FBP method for CT. A VOI (volume of interest, three-dimensional ROI) analysis of the tumor and liver at each time point was performed. The count number per organ volume was corrected to % ID/g, the physical half-life was converted from ¹¹¹In to ²²⁵Ac, the difference in physical half-life was corrected, and the time activity curve with the biological half-life added was obtained. The cumulative radioactivity amount was calculated from the integrated value of this time activity curve, and the absorbed dose was calculated in a sphere model (OLINDA/EXM ver2.0), and this was compared and examined for each antibody. However, for H01L03, a decrease in the time activity curve was not observed 168 hr after administration. Thus, the biological half-life was not considered and only the physical half-life was added.

TABLE 3

SPECT imaging conditions

| Isotope | Indium-111 medium + high energy |
|---|---|
| Collimator | MMP952 |
| Radius of Rotation | 50 mm |
| Projection Limit | 150 sec |
| Projection Count | 16 |
| Rotation Angle | 90 degrees |

TABLE 4

CT imaging conditions

| Projection count | 207 views |
|---|---|
| Frames averaged | 1 frames |
| Detector binding | 2 × 2 |
| X-ray tube current | 270 uA |
| X-ray tube voltage | 60 kV |
| Exposure time | 230 ms |
| Magnification | 2.0 |

(Results)

Figure 2:
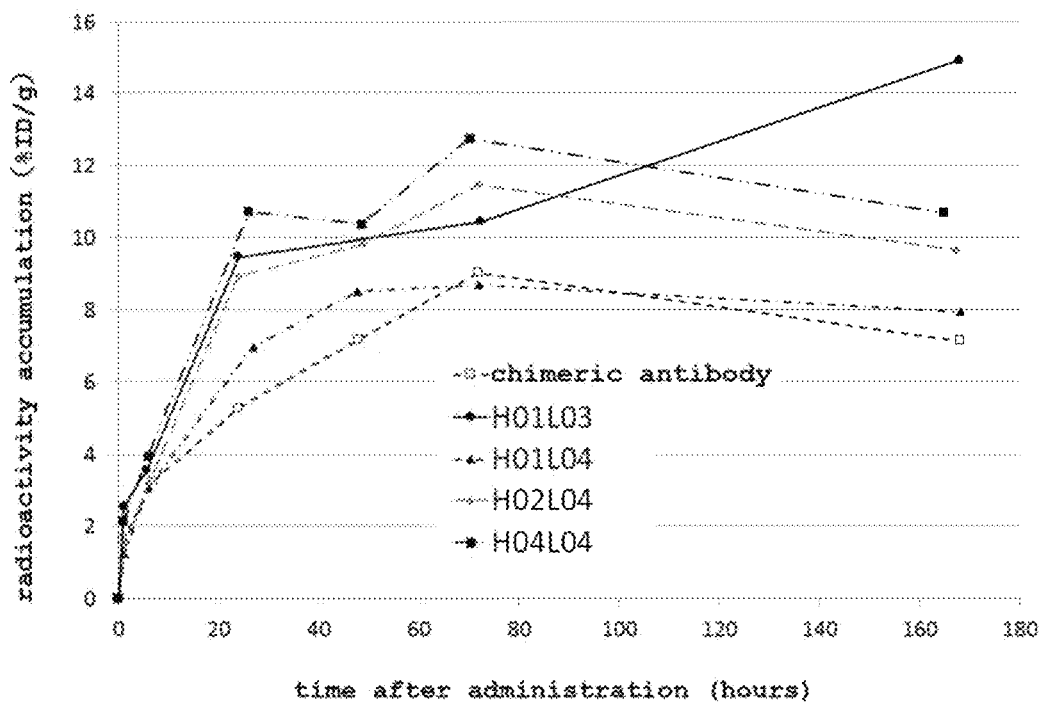
FIG. 2 shows graphs showing the results of VOI (volume of interest, three-dimensional ROI) analysis of the tumor and liver at each time point in SPECT images of respective $^{111}$In-labeled antibodies.
Figure 2:
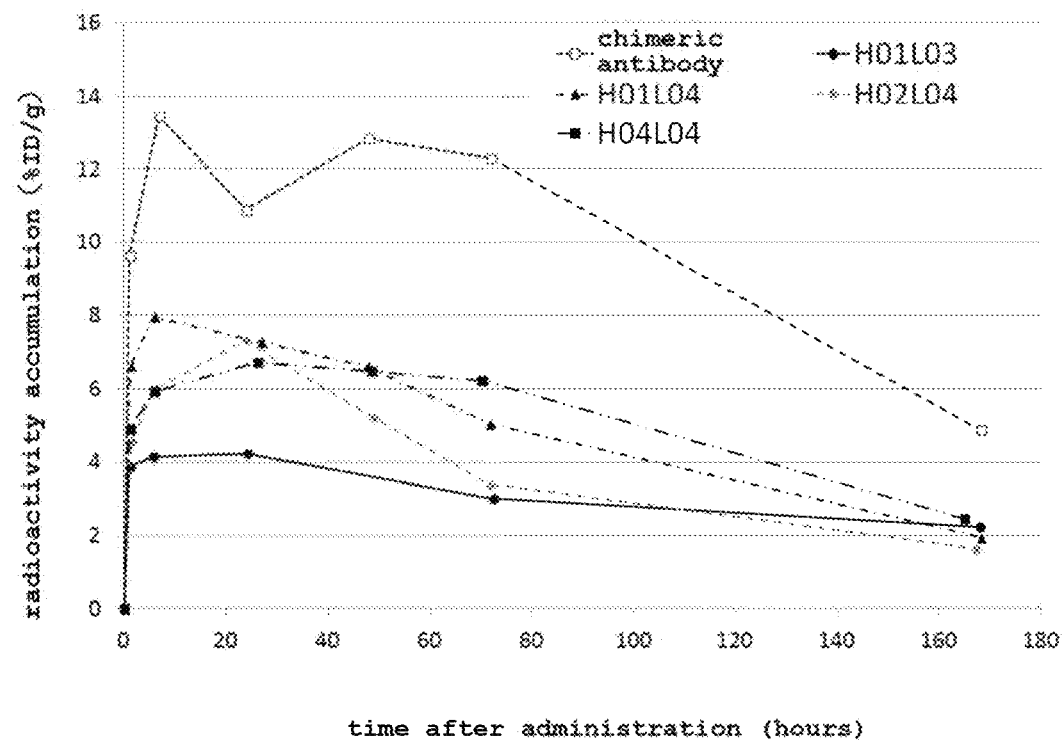
Figure 3:
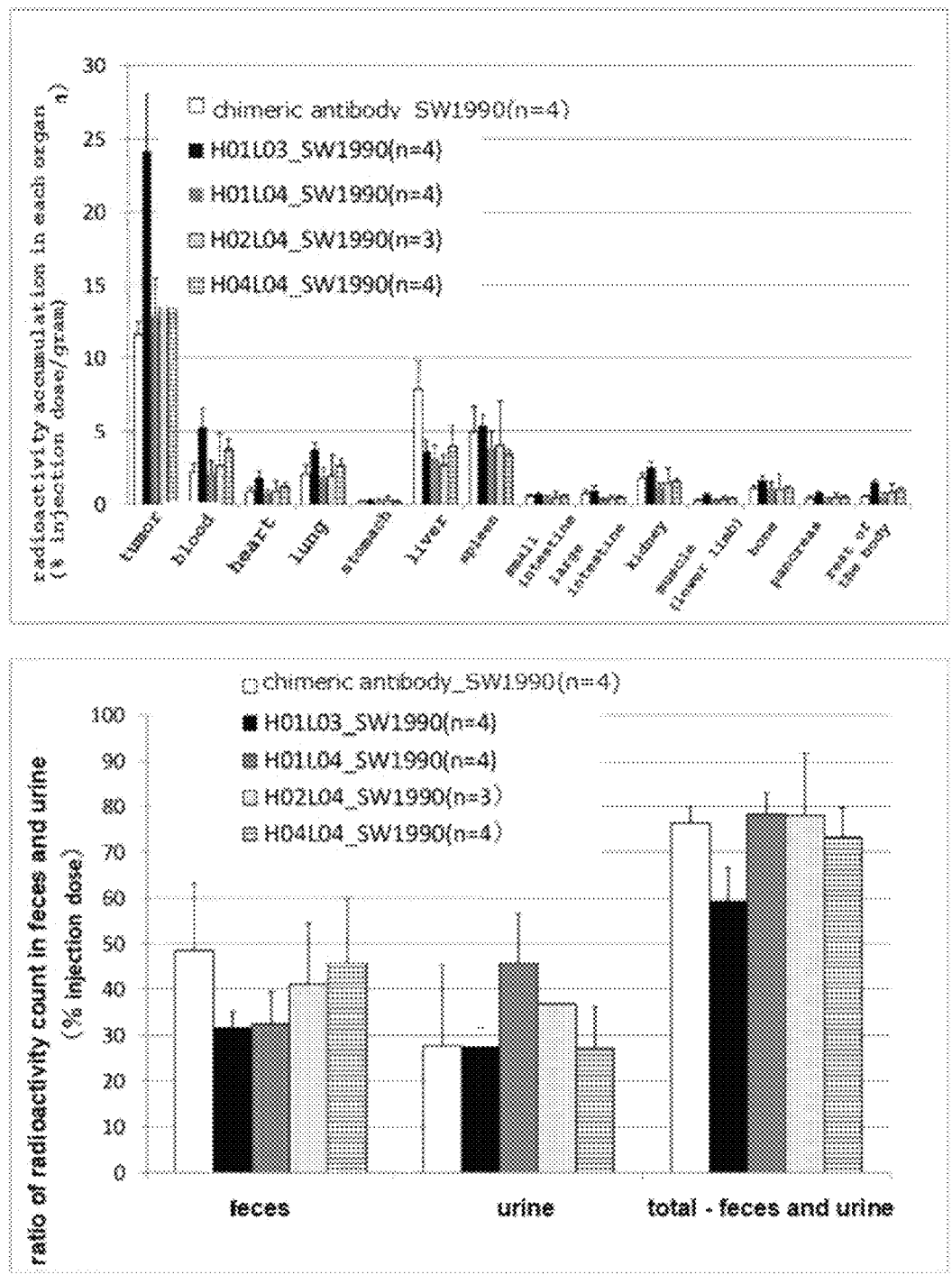
FIG. 3 is a graph showing the results of biodistribution and excretion pathway 168 hr after administration of respective $^{111}$In-labeled antibodies.

The results of performing SPECT-CT imaging are shown in FIG. 1. The results of VOI analysis of the tumor and liver at each time point are shown in FIG. 2. A graph showing the results of confirming the biodistribution and the excretion route after the completion of SPECT-CT imaging 168 hr after administration are shown in FIG. 3.

The accumulation in the tumor was highest when the humanized antibody (H01L03) was administered, and lowest when the chimeric antibody was administered. The accumulation in the liver was highest when chimeric antibody was administered, and lower when any humanized antibody was administered as compared to the chimeric antibody. When the humanized antibody (H01L03) was administered, the excretion was the slowest and the blood retention was high. Regardless of which antibody was administered, the accumulation in the liver and spleen was high among the normal organs, followed by the accumulation in the lung and kidney.

When the threshold of liver (absorbed dose) was assumed to be 30 Gy, the maximum tolerated dose was estimated to be 3.90 MBq with a humanized antibody (H01L03) and 0.43 MBq with a chimeric antibody. The maximum tolerated dose (MBq) was calculated by threshold dose (Gy)/absorbed dose (Gy/MBq).

Example 4-3: In Vitro Autoradiography

Figure 4:
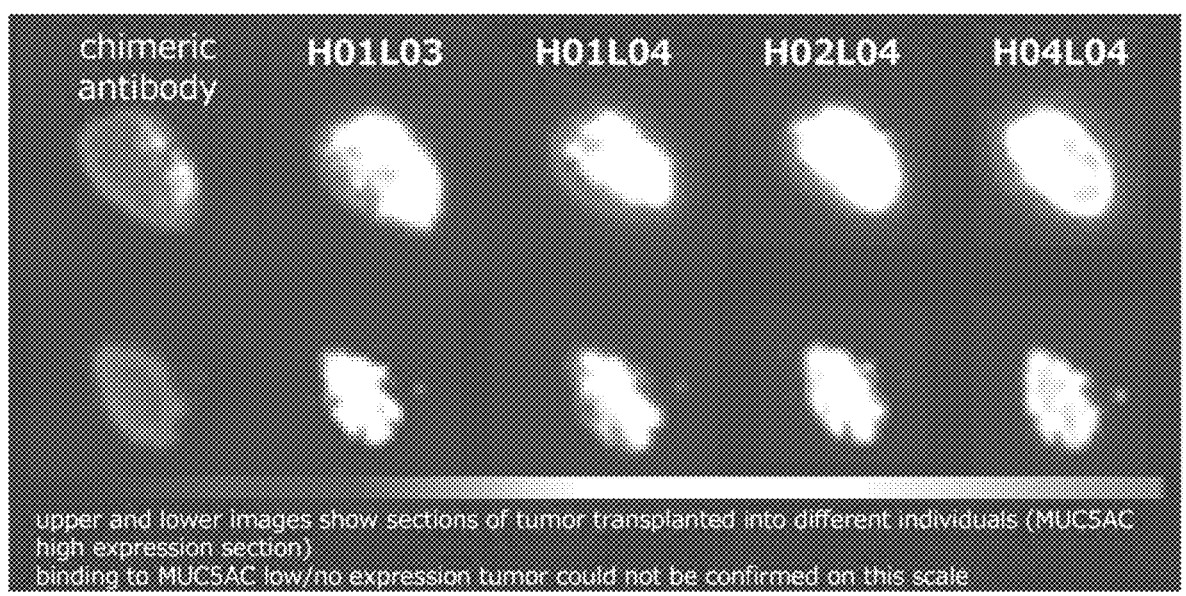
FIG. 4 is an image showing the results of the binding ability of respective $^{111}$In-labeled antibodies by in vitro ARG.
Figure 5:
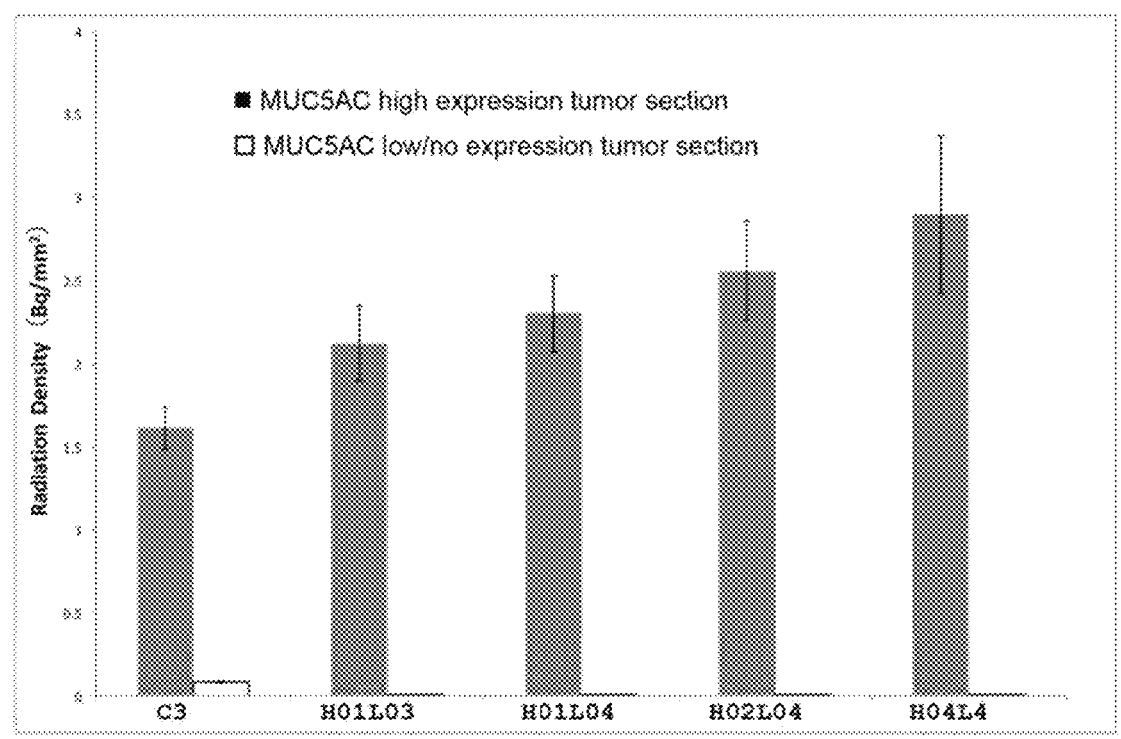
FIG. 5 shows graphs showing the results of the quantified binding ability of respective $^{111}$In-labeled antibodies by in vitro ARG.
Figure 5:
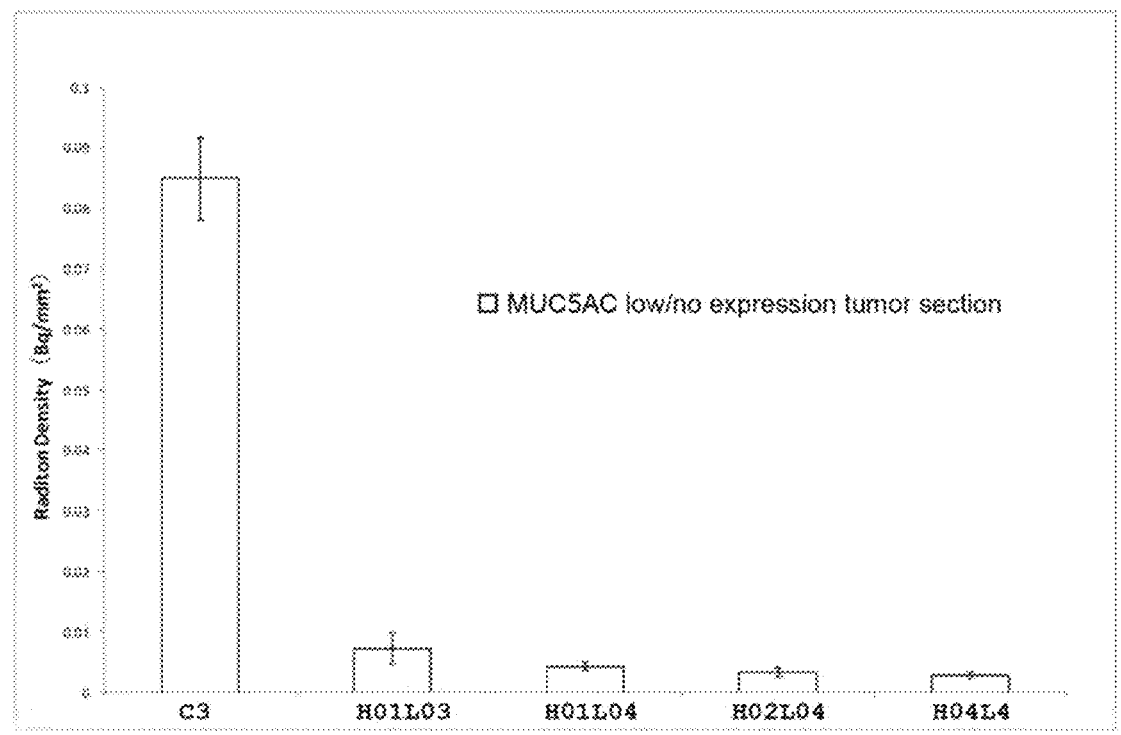

The results of images evaluating the binding property and specificity of various antibodies for MUC5AC by in vitro autoradiography (ARG) using various ¹¹¹In-labeled antibodies prepared in Example 4-1 are shown in FIG. 4. In addition, a graph of the numerical values of the radioactivity density (Bq/mm²) in the ROI calculated by setting the region of interest (ROI) in the entire section is shown in FIG. 5.

A section with a thickness of 10 μm was prepared using a cryostat (manufactured by Leica) from a frozen block obtained by freezing MUC5AC high expression tumor (SW1990 transplanted tumor tissue) or MUC5AC low expression tumor (MIAPaCa2 transplanted tumor tissue) in liquid nitrogen and used for in vitro ARG.

A section stored at −80° C. was returned to room temperature, dried for 30 min or longer, immersed in phosphate buffered saline for 30 min, and then in phosphate buffered saline containing 1% by volume bovine serum albumin for 30 min, whereby the section was hydrophilized.

The hydrophilized cryosection was immersed in 1% by volume bovine serum albumin-containing phosphate buffered saline containing 5 kBq/mL various ¹¹¹In-labeled antibodies for min each. Then, the section was washed by immersing for 5 min in each of 1% by volume bovine serum albumin-containing phosphate buffered saline, phosphate buffered saline, and phosphate buffered saline in this order. The section after washing was air dried, exposed in an imaging plate (BAS-SR2040, manufactured by Fujifilm Corporation) for about 15 hr, and an autoradiogram was obtained using a fluoroimage analyzer (Typhoon FLA 7000 IP, manufactured by GE Healthcare). Using the analysis software "Image Quant TL" attached to the fluoroimage analyzer, the obtained autoradiogram was used to set the ROI over the entire section, and the radioactivity density (Bq/mm$^2$) in the ROI was calculated.

It was confirmed that all $^{111}$In-labeled humanized antibodies retained binding property and specificity for MUC5AC (FIG. 5, data of MUC5AC high expression tumor). It was 25 confirmed that various humanized antibodies had less non-specific binding as compared with the chimeric antibody (FIG. 5, data of MUC5AC low, unexpressed tumor).

From the results of Examples 4-2 and 4-3, the humanized antibody has higher specificity for MUC5AC than the chimeric antibody, and has high accumulation in tumor and low accumulation in normal organs such as liver and the like. It was clarified that it provides a more superior delivery technique relating to RI-labeled antibodies.

The results of this Example are summarized in the following Table. In the Table, the tumor volume was calculated assuming 150 mm$^3$ in the absorbed dose of SPECT. The absorbed dose of the liver was calculated based on the mean (1.15±0.14 g, n=19) of the weight of the mouse liver used in this Example. The numerical value of the biodistribution was expressed by the mean±standard deviation of n=4 (however, n=3 for H02L04).

TABLE 5

| | | name of antibody | | | | |
|---|---|---|---|---|---|---|
| | | chimeric antibody | humanized antibody | | | |
| | | | H01L03 | H01L04 | H02L04 | H04L04 |
| SPECT absorbed dose | tumor (Gy/MBq) | 9.5 | 35.0 | 15.3 | 13.7 | 15.0 |
| | liver (Gy/MBq) | 70.1 | 7.7 | 33.4 | 27.0 | 35.4 |
| bio-distribution at 168 hr after administration | tumor (% ID/g) | 11.6 ± 0.9 | 24.2 ± 3.9 | 12.9 ± 2.6 | 15.6 ± 6.2 | 17.2 ± 4.2 |
| | liver (% ID/g) | 7.9 ± 1.9 | 3.6 ± 1.7 | 3.1 ± 0.9 | 2.7 ± 0.7 | 3.9 ± 1.4 |
| | spleen (% ID/g) | 5.0 ± 1.8 | 5.4 ± 0.8 | 3.8 ± 1.2 | 4.0 ± 3.0 | 3.4 ± 0.3 |
| | kidney (% ID/g) | 1.8 ± 0.3 | 2.5 ± 0.4 | 1.1 ± 0.3 | 1.4 ± 1.0 | 1.6 ± 0.2 |
| | blood (% ID/g) | 2.2 ± 0.6 | 5.3 ± 1.3 | 2.1 ± 0.8 | 2.6 ± 2.3 | 3.8 ± 0.7 |

Example 5: Evaluation of $^{225}$Ac-Labeled Monovalent Antibody Using Tumor-Bearing Mice The $^{225}$Ac-labeled monovalent antibody (H01L03) produced according to Example 1 was used. The tumor-bearing mice were divided into 3 groups of 2.5 kBq administration group, 5 kBq administration group, and 10 kBq administration group according to the administered radioactivity amount of the $^{225}$Ac-labeled monovalent antibody, and compared with a group administered with the humanized antibody (H01L03) produced in Production Example 1 (antibody control group). Each group contained 6 mice, and observation of general condition and measurement of the body weight and tumor volume were performed for 4 weeks after administration. The tumor-bearing mice used for the evaluation were prepared by the same procedure as in Example 4-2, and subjected to the experiment when the tumor size reached about 200 mm$^3$ 10 days after transplantation of SW1990. The animal information of each group is summarized below.

TABLE 6

Animal information (on administration of each $^{225}$Ac-labeled monovalent antibody)

| | antibody control group | $^{225}$Ac-labeled monovalent antibody group | | |
|---|---|---|---|---|
| administered radioactivity amount (kBq) | — | 2.5 | 5 | 10 |
| tumor volume (mm$^3$) | 194 ± 61 | 197 ± 51 | 184 ± 53 | 192 ± 72 |
| body weight (g) | 20.8 ± 1.1 | 20.1 ± 0.7 | 20.4 ± 0.7 | 21.4 ± 2.1 | mean ± standard deviation, n = 6

Figure 6:
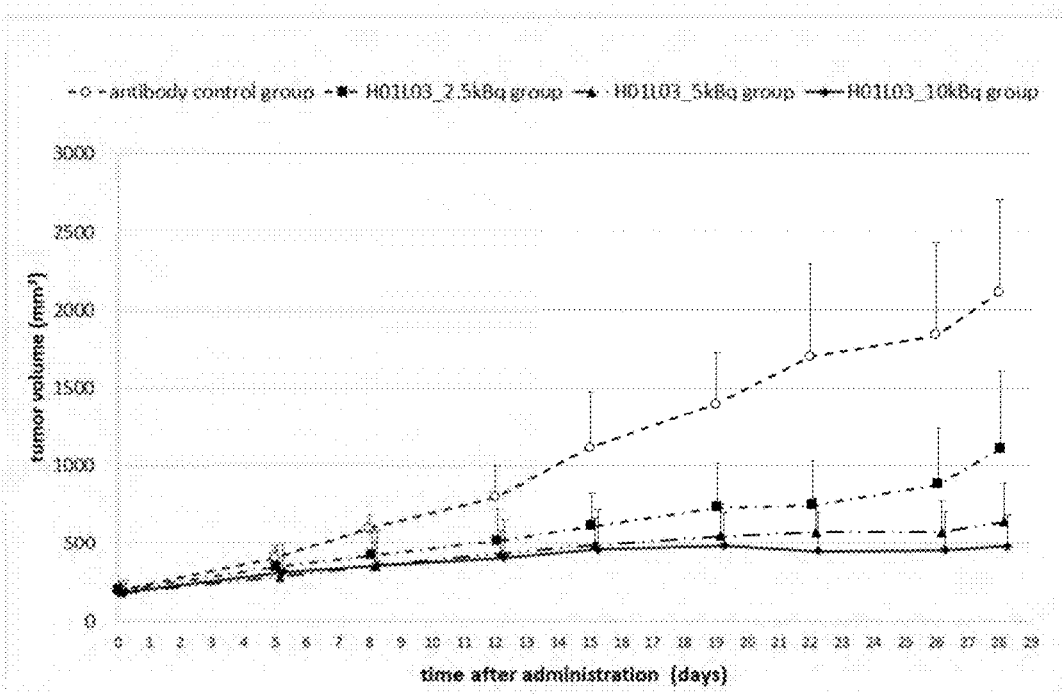
FIG. 6 is a graph showing the time-course changes in the tumor volume in tumor-bearing mice after administration of a $^{225}$Ac-labeled monovalent antibody.

The changes in tumor volume over time are shown in FIG. 6, and the relative ratio of tumor volume on the last day of the observation period when the tumor volume before administration is 1.0 is shown in the following Table. The $^{225}$Ac-labeled monovalent antibody showed a dose-dependent tumor growth inhibitory effect and statistically significantly suppressed tumor growth at all doses.

TABLE 7 relative ratio of tumor volume on the last day of observation period to tumor volume before administration

| | antibody control group | $^{225}$Ac-labeled monovalent antibody group | | |
|---|---|---|---|---|
| administered radioactivity amount (kBq) | — | 2.5 | 5 | 10 |
| relative ratio (ratio) | 10.9 | 5.6 | 3.5 | 2.5 |

A dissection was performed on the last day of the observation period, and tumors were collected and weighed. The comparison results of the tumor weight are shown in the following Table. It was found that the tumor weight for the $^{225}$Ac-labeled monovalent antibody was low in a dose-dependent manner, and that the tumor weight was statistically significantly lower in all the groups to which the $^{225}$Ac-labeled monovalent antibody was administered as compared with the antibody control group.

TABLE 8

Comparison of tumor weight

Figure 7:
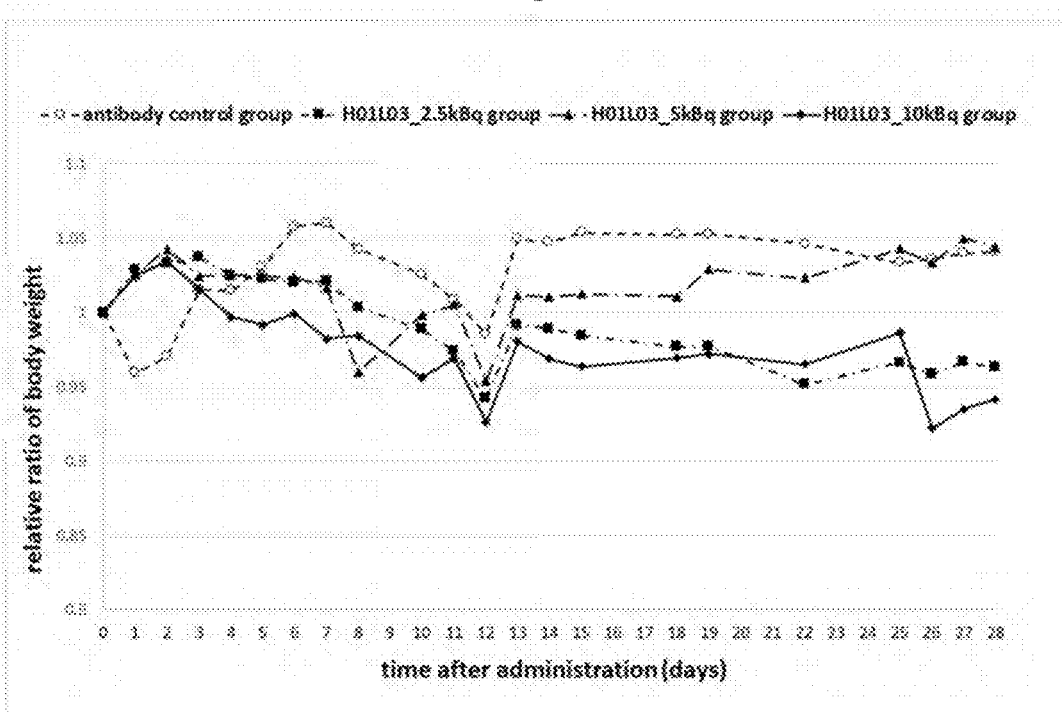
FIG. 7 is a graph showing the time-course changes in the body weight of tumor-bearing mice after administration of a $^{225}$Ac-labeled monovalent antibody, as shown in relative values with the body weight before administration as 1.0.

| | antibody control group | $^{225}$Ac-labeled monovalent antibody group | | |
|---|---|---|---|---|
| administered radioactivity amount (kBq) | — | 2.5 | 5 | 10 |
| tumor weight (g) | 2.13 ± 0.65 | 1.07 ± 0.39* | 0.71 ± 0.23* | 0.57 ± 0.21* | mean ± standard deviation,
n = 6 significance level:
*P <0.005 vs antibody control group The relative value of the change in body weight over time is shown in FIG. 7. A weight loss of 10% or more as compared with the body weight before administration was not observed in any group. Accordingly, it was shown that administration of the $^{225}$Ac-labeled monovalent antibody may have no or sufficiently low effect on the general condition.

A dissection was performed on the last day of the observation period, and liver, kidney and spleen were collected and weighed. The comparison results of the weight of each organ are shown in the following Table. It was confirmed that the weight of the liver in the group administered with 2.5 kBq of $^{225}$Ac-labeled monovalent antibody was statistically significantly lower than that in the antibody control group; however, since dose dependency was not observed, it was considered an accidental result. A statistically significant difference was not observed in the kidney or spleen, or in the liver at other doses, as compared with the antibody control group, which shows the possibility of no or sufficiently low effect on the liver, kidney and spleen.

TABLE 9

Comparison of weight of normal organ

| | antibody control group | $^{225}$Ac-labeled monovalent antibody group | | |
|---|---|---|---|---|
| administered radioactivity amount (kBq) | — | 2.5 | 5 | 10 |
| liver weight (g) | 1.00 ± 0.05 | 0.86 ± 0.05* | 0.95 ± 0.03 | 0.90 ± 0.16 |
| kidney weight (g) | 0.31 ± 0.03 | 0.26 ± 0.03 | 0.30 ± 0.02 | 0.30 ± 0.05 |
| spleen weight (g) | 0.07 ± 0.01 | 0.06 ± 0.01 | 0.07 ± 0.01 | 0.05 ± 0.02 | mean ± standard deviation,
n = 6 significance level:
*P <0.05 vs antibody control group Using blood samples collected at the end of the observation period, kidney toxicity (measurement of creatinine in plasma using Creatinine Assay Kit (manufactured by Cayman Chemical Company)), hepatic toxicity (measurement of alanine aminotransferase (ALT) in plasma using ALT activity Kit (manufactured by Bio Vision)), and blood toxicity (measurement of leukocyte count and platelet count using an automatic blood cell measuring device (model: thinka CB-1010, manufactured by ARKRAY, Inc.)) were secondarily evaluated. For each measured value, Stat PreClinica (manufactured by Takumi Information Technology Co., Ltd.) was used to confirm the homoscedasticity of the measured values. When homoscedasticity was found, analysis by the Dunnett method of parametric test was performed, and when the homoscedasticity was absent, analysis by the Steel method of the nonparametric test was performed.

Figure 8:
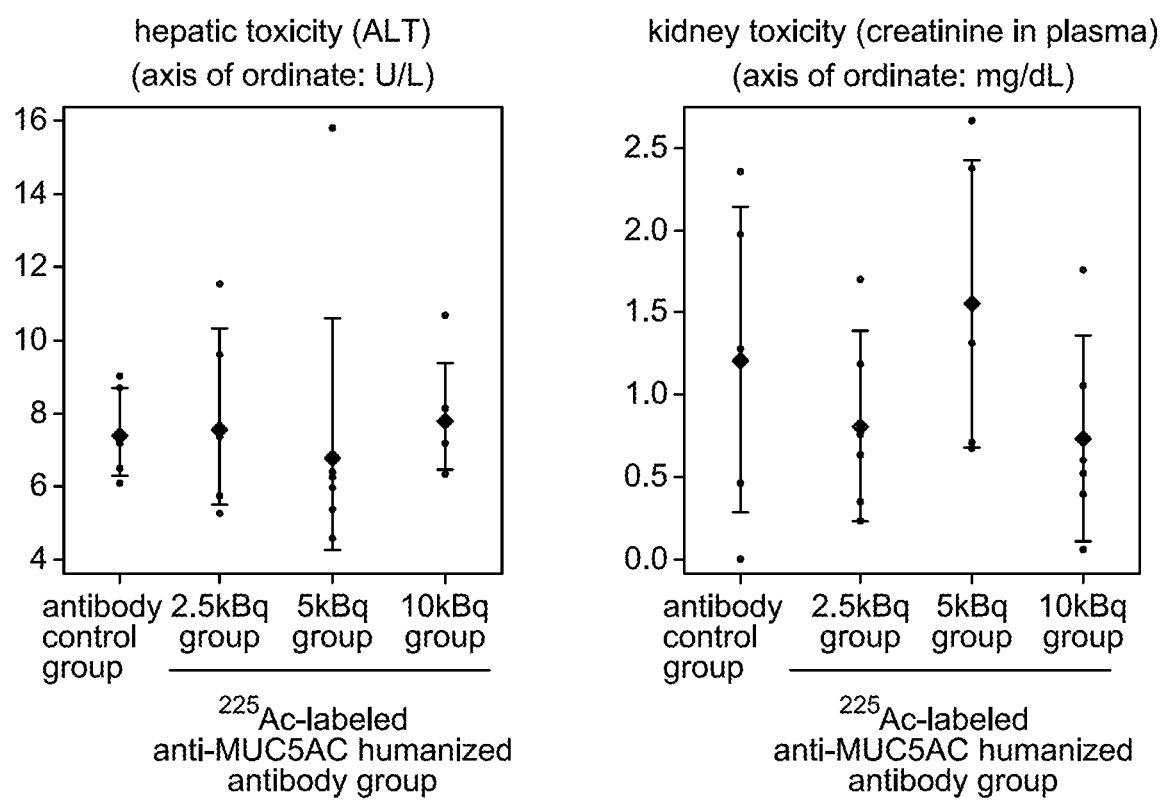
FIG. 8 is a graph showing the results of hepatotoxicity and kidney toxicity in tumor-bearing mice after administration of a $^{225}$Ac-labeled monovalent antibody.
Figure 9:
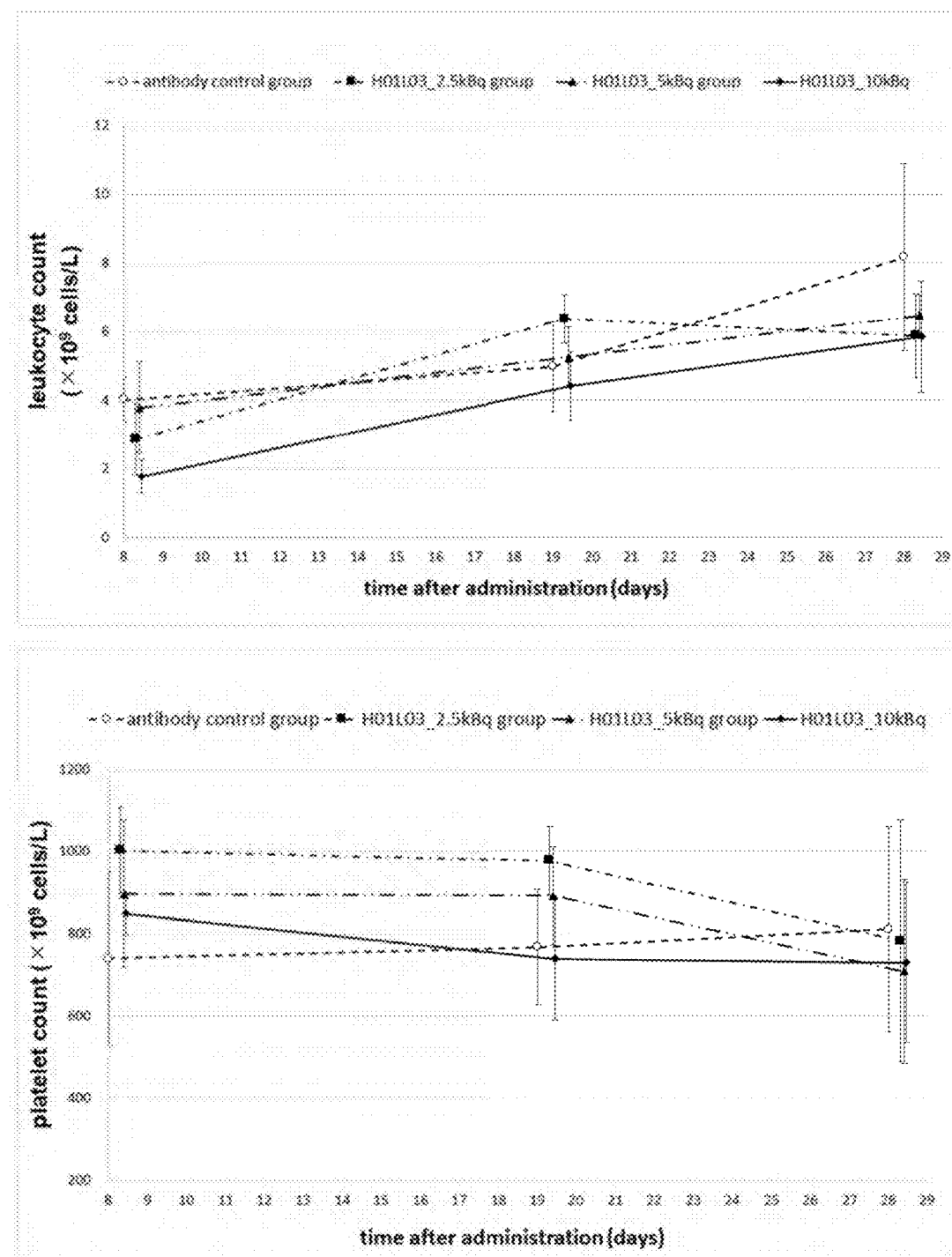
FIG. 9 is a graph showing the results of blood toxicity (leukocyte count, platelet count) in tumor-bearing mice after administration of a $^{225}$Ac-labeled monovalent antibody.

The results of hepatotoxicity and kidney toxicity are shown in FIG. 8. In all the administration groups with $^{225}$Ac-labeled monovalent antibody, a statistically significant difference was not observed at a significance level of 5% with respect to the antibody control group. The results of blood toxicity are shown in FIG. 9. A statistically significant difference was not observed at a significance level of 5% with respect to the antibody control group in each dose group of $^{225}$Ac-labeled monovalent antibody at each time point of blood sampling.

In this Example, the tumor growth inhibitory effect of the $^{225}$Ac-labeled monovalent antibody was confirmed. The inhibitory effect was dose-dependent and showed a statistically significant inhibitory effect at a significance level of 5% at all doses (2.5, 5, 10 kBq). In addition, a weight loss of 10% or more was not observed compared to the body weight before administration of the $^{225}$Ac-labeled monovalent antibody, as well as the possibility of low hepatotoxicity, low kidney toxicity, and low blood toxicity due to the $^{225}$Ac-labeled monovalent antibody was suggested. From these results, it was clarified that the $^{225}$Ac-labeled monovalent antibody has a very high antitumor effect, is highly safe, and is a very useful therapeutic agent for cancer.

Example 6: Evaluation of High Dose of $^{225}$Ac-Labeled Monovalent Antibody Using Tumor-Bearing Mice In the same manner as in Example 5 except that the administered radioactivity amount was set to 25 kBq/mice (10 times the lowest dose of Example 5), the $^{225}$Ac-labeled monovalent antibody was evaluated ($^{225}$Ac-labeled monovalent antibody administration group). In addition, a group administered with a solution of only the antibody (H01L03) produced in Production Example 1 dissolved in 20 mM ascorbic acid-containing 0.1 M acetate buffer (antibody control group) was formed. The antibody used in this Example was produced in the same manner as in Example 5. The tumor-bearing mice used for the evaluation were prepared in the same manner as in Example 4-2. Each group contained 5 mice, and observation of general condition, measurement of the body weight and tumor volume were performed for 4 weeks after administration. The animal information of each group is summarized below.

TABLE 10

| | antibody control group | $^{225}$Ac-labeled monovalent antibody group |
|---|---|---|
| administered radioactivity amount (kBq) | — | 25 |
| tumor volume (mm$^3$) | 215 ± 54 | 249 ± 67 |
| body weight (g) | 20.2 ± 1.2 | 20.8 ± 1.3 | mean ± standard deviation,
n = 5

Figure 10:
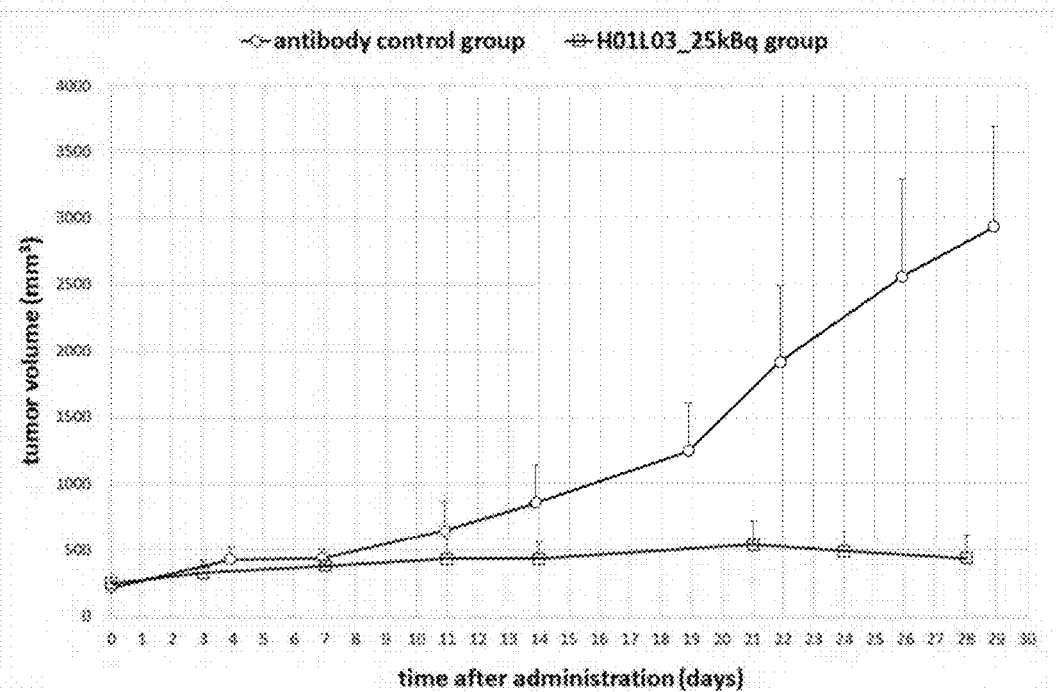
FIG. 10 is a graph showing the time-course changes in the tumor volume in tumor-bearing mice after administration of a high dose of a $^{225}$Ac-labeled monovalent antibody.

The results of the changes in tumor volume over time are shown in FIG. 10. In the $^{225}$Ac-labeled monovalent antibody administration group, a statistically significant tumor growth was suppressed, and a tumor growth inhibitory effect by the administration of a high dose of the $^{225}$Ac-labeled monovalent antibody was confirmed.

A dissection was performed on the last day of the observation period, and tumors were collected and weighed. The comparison results of the tumor weight are shown in the following Table. It was found that the tumor weight was statistically significantly low in the $^{225}$Ac-labeled monovalent antibody group as compared with the antibody control group.

TABLE 11

Comparison of tumor weight

Figure 11:
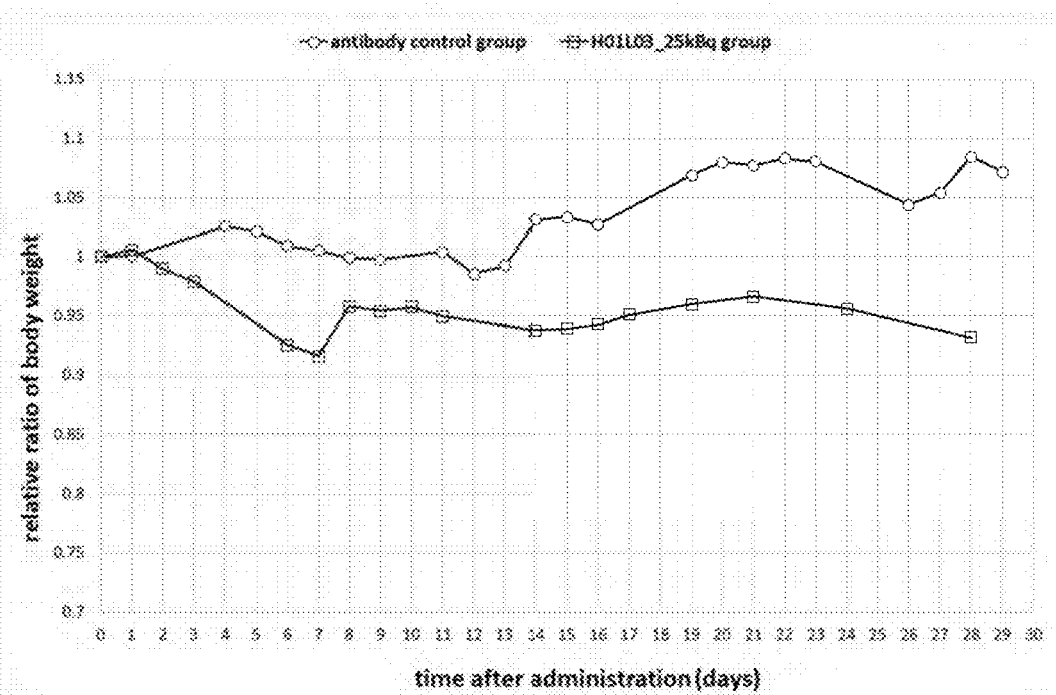
FIG. 11 is a graph showing the time-course changes in the body weight of tumor-bearing mice after administration of a high dose of a $^{225}$Ac-labeled monovalent antibody, as shown in relative values with the body weight before administration as 1.0.

|  | antibody control group | $^{225}$Ac-labeled monovalent antibody administration group |
|---|---|---|
| administered radioactivity amount (kBq) | — | 25 |
| tumor weight (g) | 2.48 ± 0.45 | 0.56 ± 0.20* | mean ± standard deviation,
n = 5 significance level:
*p <0.05 vs antibody control group The results of the changes in body weight over time are shown in FIG. 11. In the $^{225}$Ac-labeled monovalent antibody administration group, a decrease in the body weight was found at an early stage of administration; however, it was not below 0.9 in a relative ratio.

A dissection was performed on the last day of the observation period, and liver, kidney and spleen were collected and weighed. The comparison results of the organ are shown in the following Table. It was found that only the weight of spleen is statistically significantly low in the $^{225}$Ac-labeled monovalent antibody administration group as compared with the antibody control group.

TABLE 12

Comparison of normal organ weight

Figure 12:
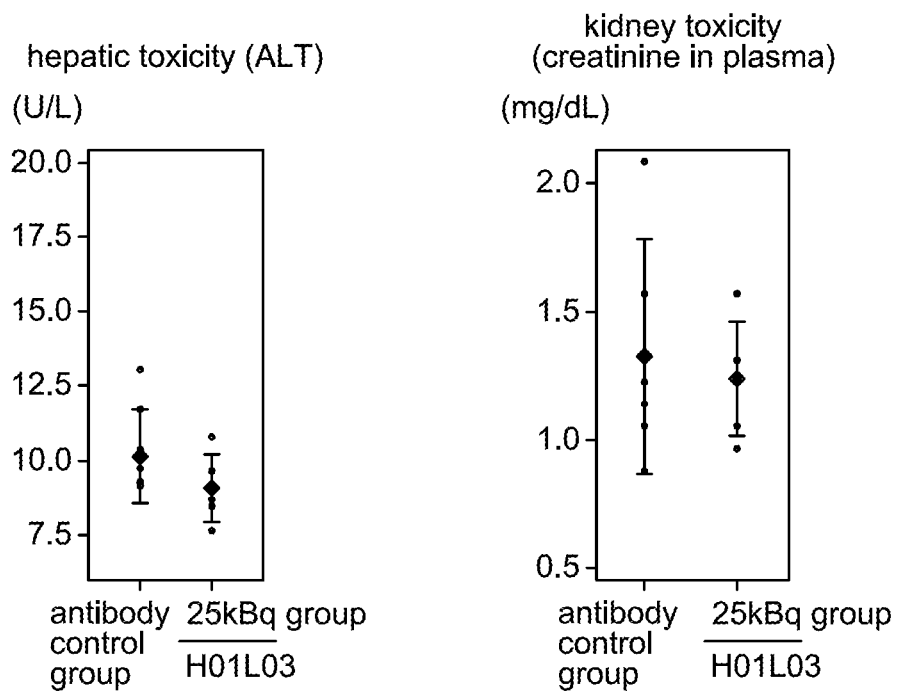
FIG. 12 is a graph showing the confirmation results of hepatotoxicity and kidney toxicity in tumor-bearing mice after administration of a high dose of a $^{225}$Ac-labeled antibody.
Figure 13:
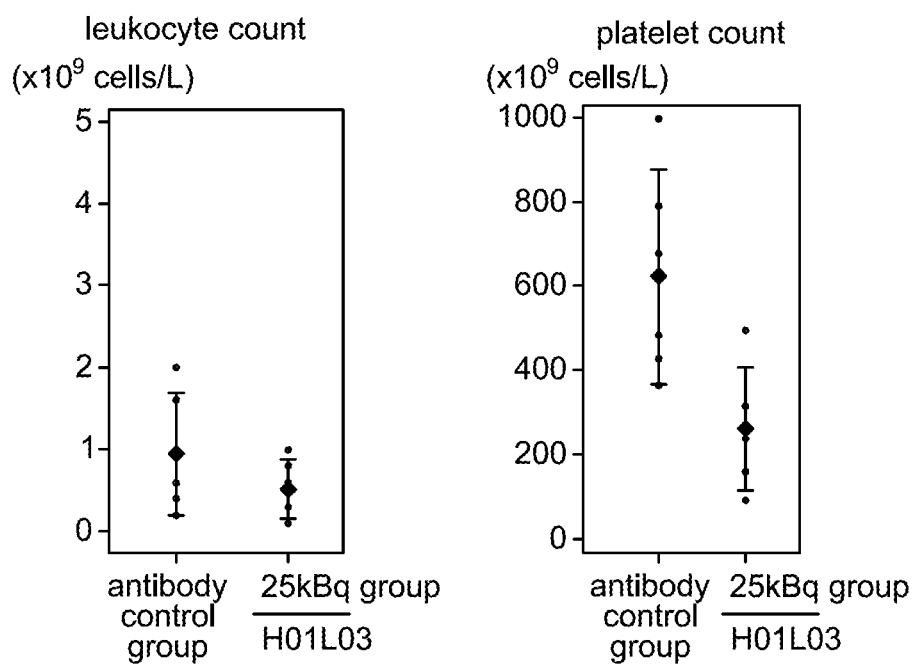
FIG. 13 is a graph showing the confirmation results of blood toxicity (leukocyte count, platelet count) in tumor-bearing mice after administration of a high dose of $^{225}$Ac-labeled antibody.

|  | antibody control group | $^{225}$Ac-labeled monovalent antibody administration group |
|---|---|---|
| administered radioactivity amount (kBq) | — | 25 |
| liver (g) | 0.99 ± 0.12 | 1.08 ± 0.03 |
| kidney (g) | 0.31 ± 0.03 | 0.31 ± 0.02 |
| spleen (g) | 0.07 ± 0.03 | 0.04 ± 0.01* | mean ± standard deviation,
n = 5 significance level:
*P < 0.05 vs antibody control group The results of hepatotoxicity and kidney toxicity are shown in FIG. 12. Since a statistically significant difference was not observed with respect to the antibody control group, it was suggested that this dose does not induce hepatopathy or renopathy. The results of blood toxicity are shown in FIG. 13. Since a statistically significant difference was not observed with respect to the antibody control group, it was suggested that this dose does not induce blood toxicity.

From these results, it was also suggested that the $^{225}$Ac-labeled monovalent antibody has a very high antitumor effect, is highly safe, and is a very useful therapeutic agent for cancer.

As a method of converting a mouse dose to a human dose, a method using the following formula can be mentioned.

Animal dose in mg/kg×(animal weight in kg/human weight in kg)×0.33

According to this formula, administration of 25 kBq/20 g to mice in this Example corresponds to administration at 89.0 kBq/kg (human).

Example 7: Evaluation of $^{225}$Ac-Labeled Monovalent Antibody and $^{225}$Ac-Labeled Divalent Antibody Using Tumor-Bearing Mice Using tumor-bearing mice, the properties of each antibody of the $^{225}$Ac-labeled monovalent antibody and $^{225}$Ac-labeled divalent antibody were evaluated. The $^{225}$Ac-labeled monovalent antibody produced according to Example 2 was administered to tumor-bearing mice produced in the same manner as in Example 4-2 at an administered radioactivity amount of 5 kBq/mouse or 10 kBq/mouse ($^{225}$Ac-labeled monovalent antibody administration group). The $^{225}$Ac-labeled divalent antibody produced according to Example 3 was administered to tumor-bearing mice produced in the same manner as in Example 4-2 at an administered radioactivity amount of 5 kBq/mouse or 10 kBq/mouse ($^{225}$Ac-labeled divalent antibody administration group). Similar to Examples 5 and 6, an antibody control group was formed. Each group contained 6 mice, and observation of general condition and measurement of the body weight and tumor volume were performed for 4 weeks after administration. The animal information of each group is summarized below.

TABLE 13

|  | antibody control group | $^{225}$Ac-labeled monovalent antibody administration group | | $^{225}$Ac-labeled divalent antibody administration group | |
|---|---|---|---|---|---|
| administered radioactivity amount (kBq) | — | 5 | 10 | 5 | 10 |
| tumor volume (mm³) | 194 ± 40 | 209 ± 21 | 203 ± 31 | 192 ± 38 | 188 ± 50 |
| body weight (g) | 21.0 ± 1.2 | 21.5 ± 0.9 | 21.9 ± 1.1 | 21.3 ± 1.6 | 21.0 ± 1.2 | mean ± standard deviation,
n = 6

Figure 14:
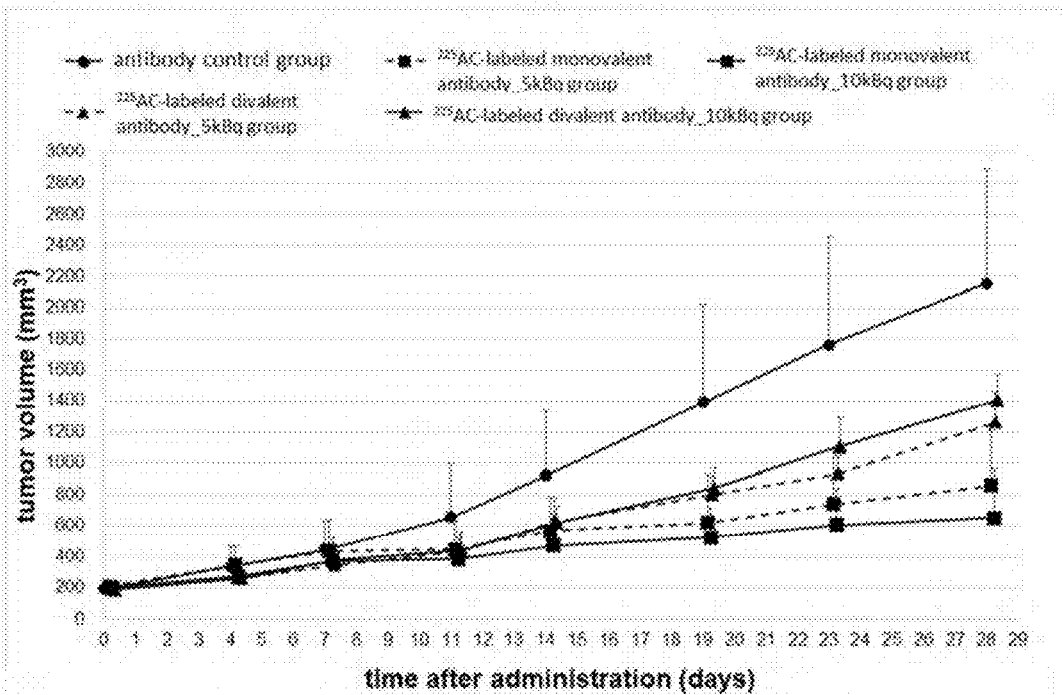
FIG. 14 is a graph showing the time-course changes in the tumor volume in tumor-bearing mice after administration of a $^{225}$Ac-labeled monovalent antibody or a $^{225}$Ac-labeled divalent antibody.

The results of the changes in tumor volume over time are shown in FIG. 14. The tumor volume on the last day of the observation period and the relative ratio when the tumor volume before administration is 1.0 is shown in the following Table. In the $^{225}$Ac-labeled monovalent antibody administration group, a statistically significant tumor growth was suppressed, and a dose-dependent tumor growth inhibitory effect was confirmed. In the $^{225}$Ac-labeled divalent antibody administration group, tumor growth was tended to be suppressed.

TABLE 14

Relative ratio of tumor volume on the last day of observation period to tumor volume before administration

|  | antibody control group | $^{225}$Ac-labeled monovalent antibody administration group | | $^{225}$Ac-labeled divalent antibody administration group | |
|---|---|---|---|---|---|
| administered radioactivity amount (kBq) | — | 5 | 10 | 5 | 10 |
| tumor volume (mm³) | 2156 ± 737 | 858 ± 357* | 654 ± 310* | 1267 ± 194 | 1406 ± 166 |
| relative ratio (ratio) | 11.1 | 4.11 | 3.22 | 6.59 | 7.48 | mean ± standard deviation,
n = 6 significance level:
*P < 0.05 vs antibody control group The mice were euthanized by exsanguination under isoflurane anesthesia on the last day of the observation period, and tumors were collected and weighed. The comparison results of the tumor weight are shown in the following Table. It was found that the tumor weight in the $^{225}$Ac-labeled monovalent antibody administration group was statistically significantly low as compared with the antibody control group, and a dose-dependent tumor growth inhibitory effect was confirmed. In the $^{225}$Ac-labeled divalent antibody administration group, the tumor weight was low as compared with the antibody control group, but a statistically significant difference was not found.

TABLE 15

Comparison of tumor weight

Figure 15:
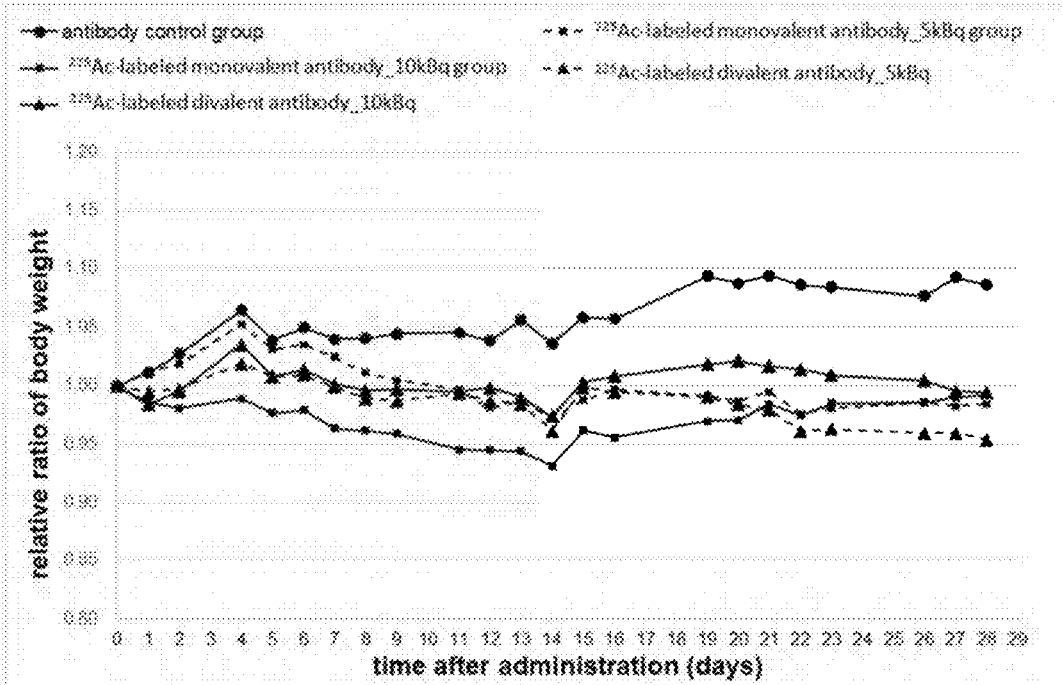
FIG. 15 is a graph showing the time-course changes in the body weight of tumor-bearing mice after administration of a $^{225}$Ac-labeled monovalent antibody or a $^{225}$Ac-labeled divalent antibody, as shown in relative values with the body weight before administration as 1.0.

| | antibody control group | $^{225}$Ac-labeled monovalent antibody administration group | | $^{225}$Ac-labeled divalent antibody administration group | |
|---|---|---|---|---|---|
| administered radioactivity amount (kBq) | — | 5 | 10 | 5 | 10 |
| tumor weight (g) | 1.96 ± 0.51 | 0.86 ± 0.25* | 0.66 ± 0.23* | 1.41 ± 0.19 | 1.39 ± 0.29 | mean ± standard deviation,
n = 6 significance level:
*P < 0.05 vs antibody control group The results of the changes in body weight over time are shown in FIG. 15. The mean of the relative ratio was not lower than 0.9. In addition, the relative ratio of each individual was not lower than 0.8.

The mice were euthanized by exsanguination under isoflurane anesthesia and a deissection was performed on the last day of the observation period. As a result of dissection, abnormal finding was absent. In addition, liver, kidney and spleen were collected and weighed. The comparison results of the weight of the normal organs are shown in the following Table. A statistically significant decrease in organ weight was not observed in any of the $^{225}$Ac-labeled antibody administration groups as compared with the antibody control group.

TABLE 16

Comparison of weight of normal organ

| | antibody control group | $^{225}$Ac-labeled monovalent antibody administration group | | $^{225}$Ac-labeled divalent antibody administration group | |
|---|---|---|---|---|---|
| administered radioactivity amount (kBq) | — | 5 | 10 | 5 | 10 |
| liver (g) | 1.10 ± 0.14 | 1.13 ± 0.13 | 1.14 ± 0.14 | 0.97 ± 0.09 | 1.01 ± 0.10 |
| kidney (g) | 0.32 ± 0.05 | 0.30 ± 0.03 | 0.32 ± 0.04 | 0.28 ± 0.03 | 0.30 ± 0.04 |
| spleen (g) | 0.077 ± 0.012 | 0.065 ± 0.017 | 0.068 ± 0.010 | 0.060 ± 0.011 | 0.061 ± 0.013 | mean ± standard deviation,
n = 6

Figure 16:
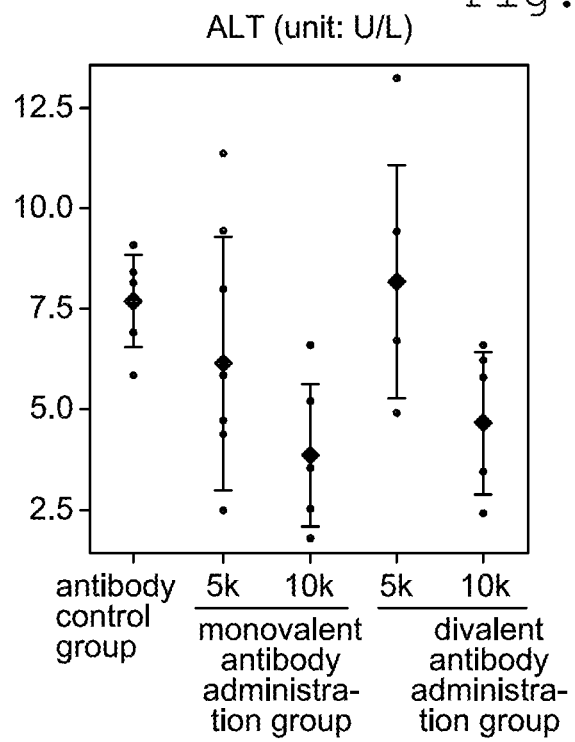
FIG. 16 is a graph showing the results of hepatotoxicity in tumor-bearing mice after administration of a $^{225}$Ac-labeled monovalent antibody or $^{225}$Ac-labeled divalent antibody.
Figure 16:
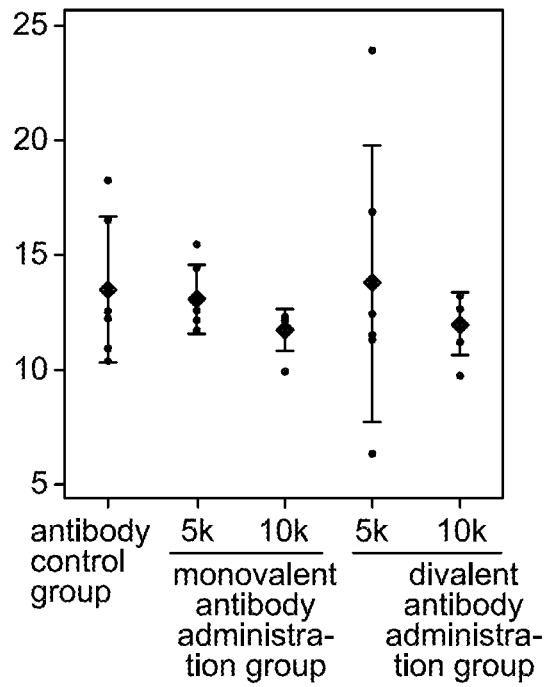
Figure 17:
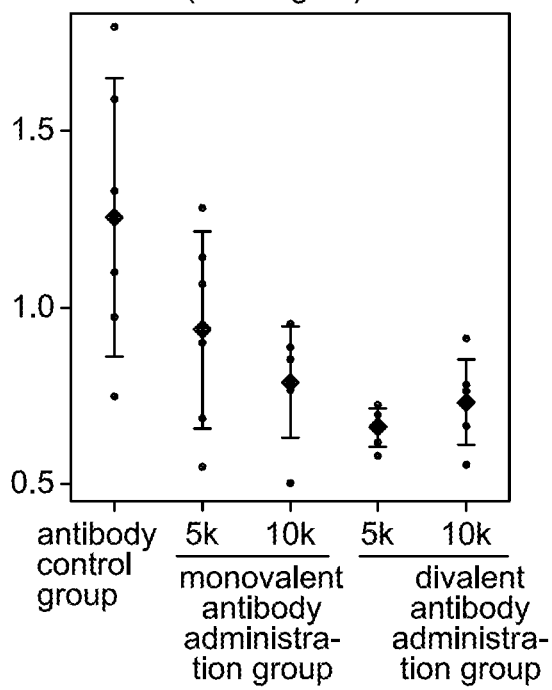
FIG. 17 is a graph showing the results of kidney toxicity in tumor-bearing mice after administration of a $^{225}$Ac-labeled monovalent antibody or $^{225}$Ac-labeled divalent antibody.
Figure 17:
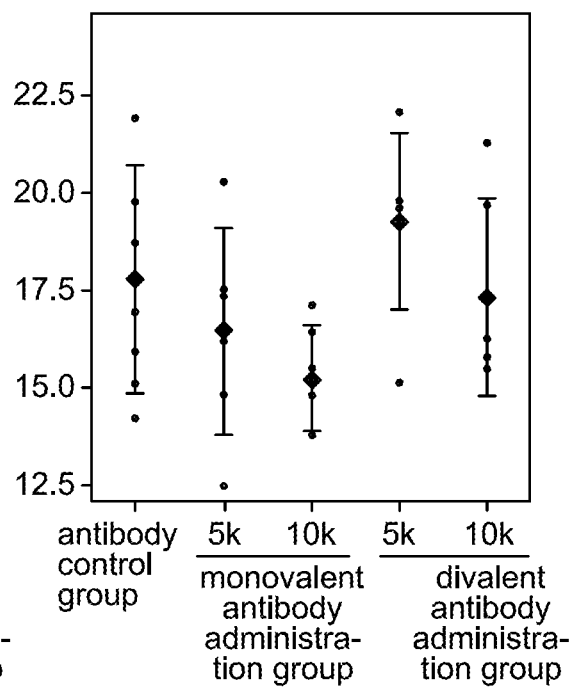
Figure 18:
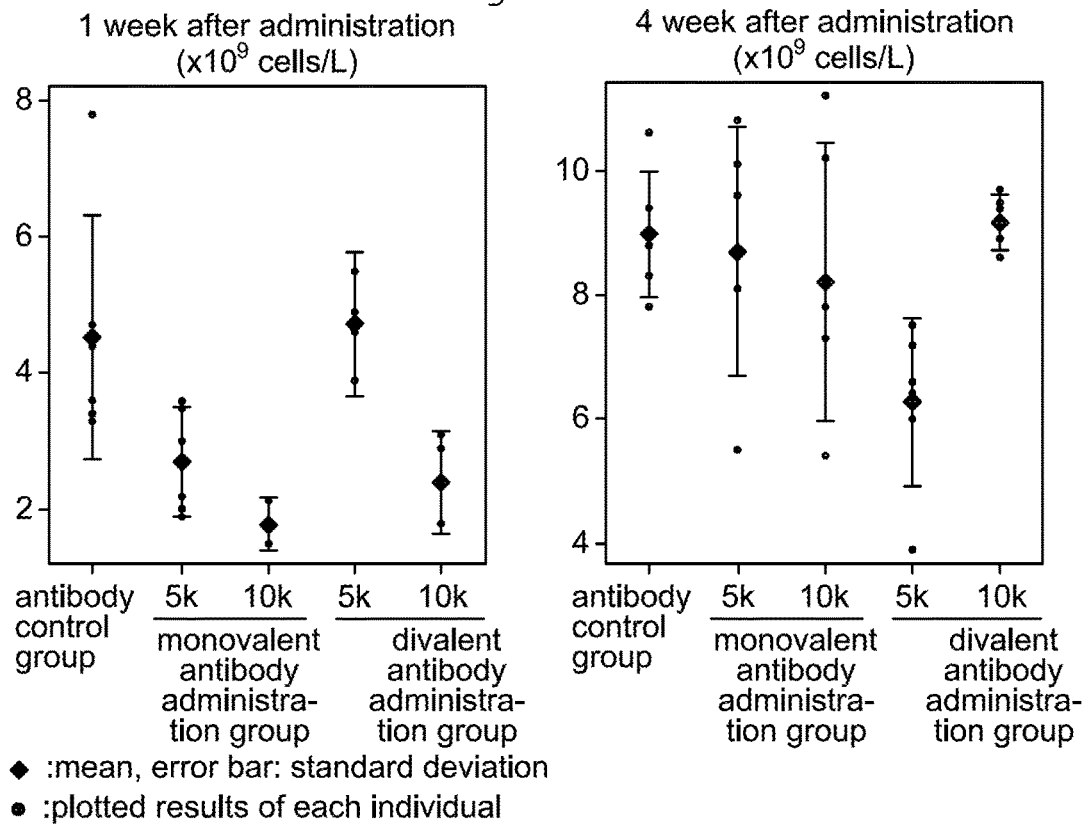
FIG. 18 is a graph showing the results of blood toxicity (leukocyte count) in tumor-bearing mice after administration of a $^{225}$Ac-labeled monovalent antibody or $^{225}$Ac-labeled divalent antibody.
Figure 19:
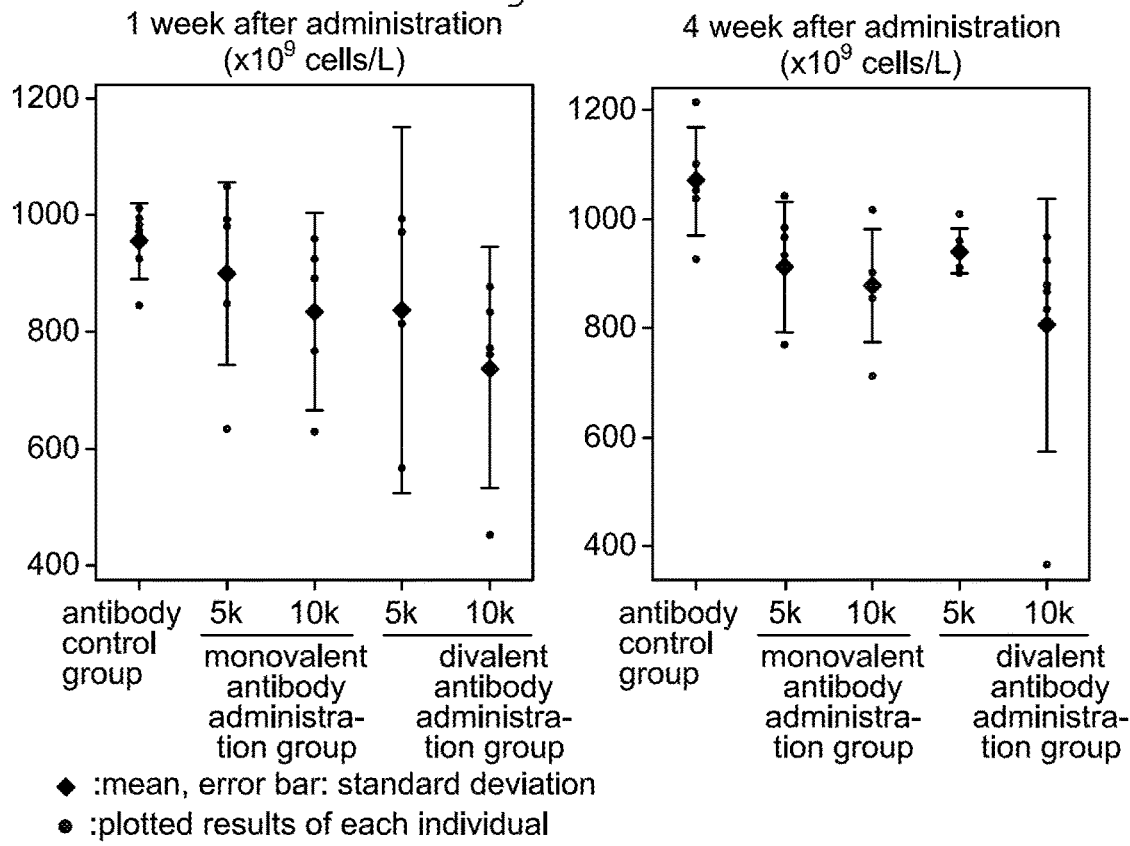
FIG. 19 is a graph showing the results of blood toxicity (platelet count) in tumor-bearing mice after administration of a $^{225}$Ac-labeled monovalent antibody or $^{225}$Ac-labeled divalent antibody.

The results of hepatotoxicity of the $^{225}$Ac-labeled monovalent antibody and $^{225}$Ac-labeled divalent antibody are shown in FIG. 16. The results of kidney toxicity are shown in FIG. 17. Since a statistically significant increase in the value was not observed with respect to the antibody control group, it was suggested that this dose does not induce hepatotoxicity or kidney toxicity. Regarding blood toxicity, the results of the leukocyte count 1 week after administration and 4 weeks after administration are shown in FIG. 18. Also, the results of the platelet count 1 week after administration and 4 weeks after administration are shown in FIG. 19. Regarding the leukocyte count, a statistically significant difference was observed 1 week after administration in the monovalent antibody administration group (5 kBq and 10 kBq) and the divalent antibody administration group (10 kBq) as compared with the antibody control group, but the count recovered in 4 weeks after administration. In the divalent antibody administration group (5 kBq), which showed a statistically significant difference from the antibody control group 4 weeks after administration, the difference was not dose-dependent. The platelet count was not fall below 500×10$^9$ cells/L (the lower limit of the normal range) at any time point except for one individual. From these, it was suggested that this dose does not induce blood toxicity.

Example 8: Comparison of Pharmacokinetics Using In-111($^{111}$In)-Labeled Monovalent Antibody and $^{111}$In-Labeled Divalent Antibody Example 8-1: Preparation of Each $^{111}$In-Labeled Antibody To compare the pharmacokinetics of monovalent antibody and divalent antibody, monovalent antibody and divalent antibody were labeled with $^{111}$In, administered to tumor-bearing mice, biodistribution experiment was performed 20, 68, and 188 hr after administration, and the pharmacokinetics of the monovalent antibody and divalent antibody were compared.

(1) Production of Each Antibody Introduced with Chelator

The antibody was produced in the same manner as in Production Example 1 and Production Example 2, and monovalent antibody and divalent antibody of the peptide-modified antibody of humanized antibody H01L03 were obtained.

A 0.1 mol/L sodium acetate buffer (pH 6.0) containing 34 nmol of chelate site (structural formula: L1-4) and a 0.1 mol/L arginine-containing 0.1 mol/L histidine buffer (pH 6.0) containing 34 nmol of monovalent antibody or divalent antibody were reacted at 37° C. for 120 min to give a chelator-introduced antibody.

This was passed through a desalting column (model number: PD-10, manufactured by GE Healthcare) and a fraction containing the chelator-introduced antibody was recovered. The recovered fraction was further purified using ultrafiltration filter (manufactured by Merck, model number:

UFC505096). The concentration of the purified monovalent antibody was 7.13 mg/mL, and the concentration of the divalent antibody was 5.07 mg/mL.

(2) Radiolabeling of Each Antibody with $^{111}$In

Using a $^{111}$In ion-containing solution (indium ($^{111}$In) chloride Injection, manufactured by Nihon Medi-Physics Co., Ltd.) as a radioactive metal source at 91-92 MBq as a radioactive amount, each chelator-introduced antibody (0.05 mL) was added, and they were mixed well. It was confirmed that the pH was 4 by using a pH test paper (manufactured by Merck). This was reacted at 45° C. for 120 min.

The reaction mixture was purified using an ultrafiltration filter (manufactured by Merck, model number: UFC505096), and the solvent was further substituted with a 20 mmol/L ascorbic acid-containing 90 mmol/L sodium acetate buffer.

The radiochemical yield of each $^{111}$In-labeled antibody was 55% for the monovalent antibody and 59% for the divalent antibody. The radiochemical purity was 97% for the monovalent antibody, and 98% for the divalent antibody. The amount of radioactivity administered to the animal is shown in Table 17. The radiochemical yield is the ratio (%) of the radioactivity count of the $^{111}$In-labeled monovalent/divalent antibody to the radioactivity amount calculated from the radioactivity count at the start of the step (1). For the radioactivity measurement, a radioisotope Doze Calibrator (manufactured by CAPINTEC, model number: CRC-15R) was used. The radiochemical purity refers to the ratio (%) of the peak radioactivity count corresponding to the $^{111}$In-labeled antibody to the total radioactivity count of the thin layer plate as analyzed by filter thin layer chromatography. For thin layer chromatography (thin layer plate: manufactured by Agilent, model number: SGI0001, developing solvent: 100 mmol/L EDTA solution (pH 5.0)/acetonitrile mixed solution (volume ratio 1:1) was developed, and the radioactivity count was detected using a radio γ-TLC analyzer (manufactured by raytest, MODEL GITA Star).

mice were euthanized at each time point by exsanguination under isoflurane anesthesia. Tumor, blood, and normal organs (including the rest of the body) were collected and weighed. The amount of radioactivity in excreted feces and excreted urine in addition to the weighed organs was measured (γ-ray well scintillation measuring apparatus: JDC-1712, manufactured by Hitachi Aloka Medical, Ltd.). The radioactivity accumulation rate (% ID) with respect to the dose was calculated from the radioactivity amount (count) of each organ (including excreted feces and excreted urine), and the amount of accumulated radioactivity (% ID/g) was calculated as the rate of radioactivity accumulation per organ weight.

(Results)

Figure 20:
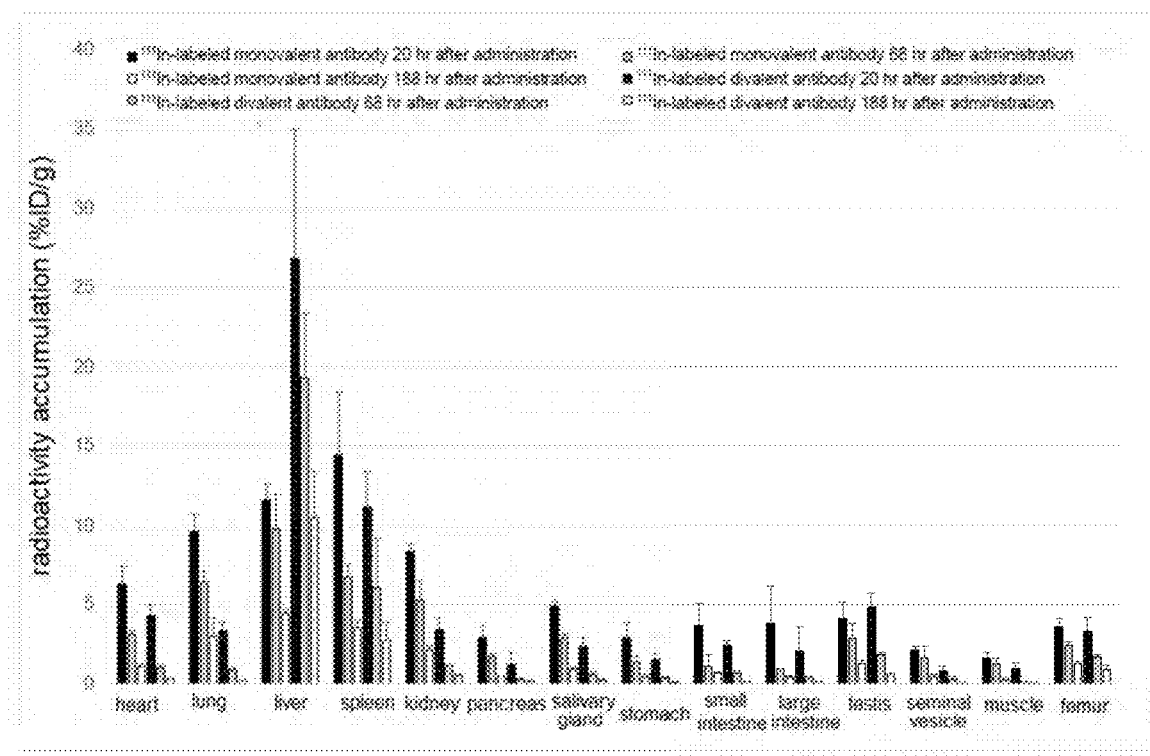
FIG. 20 is a graph showing the results of the amount of radioactivity per unit weight (% ID/g) in each organ in the biodistribution 20, 68 and 188 hr after administration of a $^{111}$In-labeled monovalent or divalent antibody.
Figure 21:
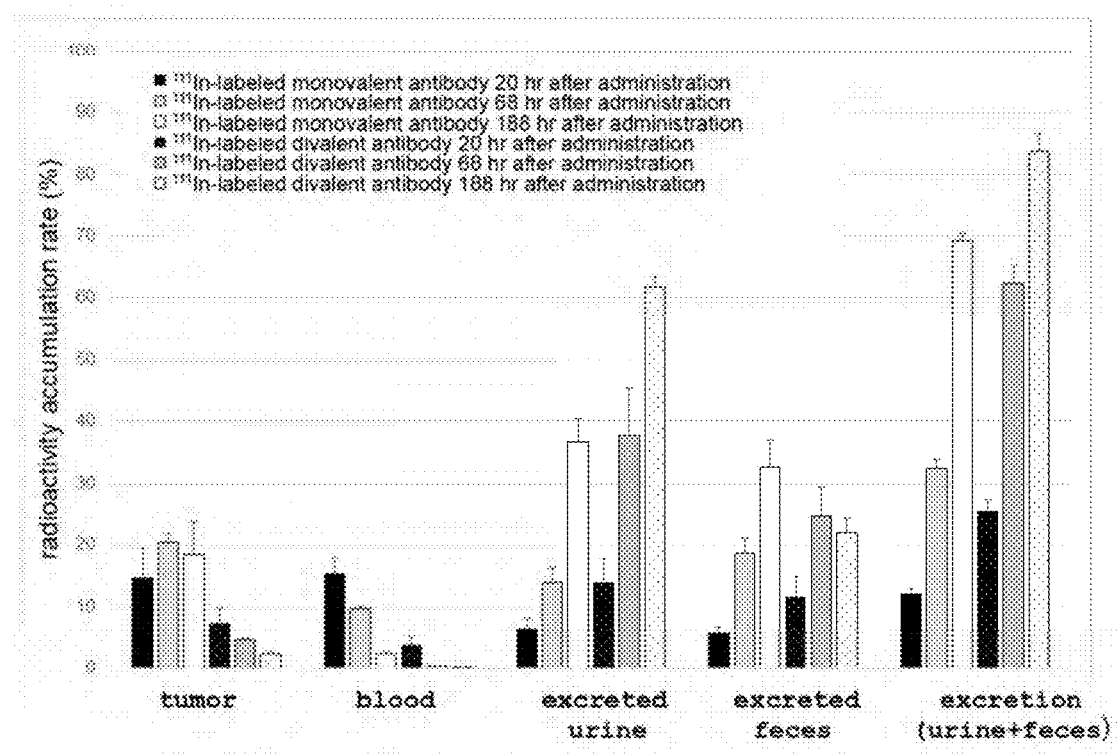
FIG. 21 is a graph showing the time-course changes in the rate of radioactivity in tumor, blood, excreted urine, excreted feces, and a total of excreted urine and excreted feces in the biodistribution 20, 68 and 188 hr after administration of a $^{111}$In-labeled monovalent or divalent antibody.

The results showing changes in the amount of radioactivity accumulated in each organ over time are shown in FIG. 20. The results showing the radioactivity accumulation rate of excreted feces and excreted urine, and changes in the total radioactivity accumulation rate over time are shown in FIG. 21.

The amount of radioactivity accumulated in blood was higher for monovalent antibody than for divalent antibody at any time point. From this, it was confirmed that the monovalent antibody has higher blood retention property than the divalent antibody. The amount of radioactivity accumulated in the tumor was higher for the monovalent antibody than for the divalent antibody at any time point. It was confirmed that the tendency of radioactivity accumulation in normal organs was higher in the order of spleen, liver, lung, and kidney for monovalent antibody. It was confirmed that the divalent antibody showed remarkably higher values in the order of liver and spleen, and higher in the order of testis, heart, kidney, and femur. It was confirmed that the radioactivity accumulation in each normal organ decreases over time. The excretion amount for the divalent antibody was higher than that for the monovalent antibody at any time point, and it was confirmed that the clearance rate for the

TABLE 17

$^{111}$In labeling information

| time point (group) | $^{111}$In-labeled monovalent antibody | | | $^{111}$In-labeled divalent antibody | | |
| --- | --- | --- | --- | --- | --- | --- |
| | 20 hr after administration | 68 hr after administration | 188 hr after administration | 20 hr after administration | 68 hr after administration | 188 hr after administration |
| radiochemical yield (%) | | 55 | | | 59 | |
| radiochemical purity (%) | | 97 | | | 98 | |
| administered radioactivity amount (MBq) | 4.76 ± 0.10 | 5.02 ± 0.08 | 4.85 ± 0.04 | 4.95 ± 0.22 | 4.91 ± 0.18 | 4.89 ± 0.14 |

Example 8-2: Biodistribution Using Tumor-Bearing Mice

Human pancreatic cancer cell line SW1990 (0.5×10$^7$ cells) were subcutaneously administered to Balb/c nude mouse (male) from the flank to the back thereof. When the tumor volume reached about 300 mm$^3$, the $^{111}$In-labeled monovalent antibody and divalent antibody prepared in Example 8-1 were administered from the tail vein.

(Evaluation Method)

The tumor-bearing mice were reared in a metabolic cage after administration of each $^{111}$In-labeled antibody, and feces and urine excreted up to each time point (20, 68, 188 hr after administration) were collected. The tumor-bearing divalent antibody was faster. With monovalent antibody, fecal and urinary excretion amounts were similar. On the other hand, it was confirmed that urinary excretion was higher than fecal excretion with divalent antibody, and that it is excreted mainly in the renal urinary tract system.

Example 9: Production of $^{225}$Ac-Labeled Anti-MUC5AC Humanized Antibody Using $^{225}$Ac-Labeled DOTAGA-DBCO (1. Chelating Agent Synthesis Step)

The structure of the chelate site (DOTAGA-DBCO) used in this Example is represented by the following formula (L1-5). DOTAGA-DBCO represented by the formula (L1-5)

was produced according to the method described in Bernhard et al. DOTAGA-Anhydride: A Valuable Building Block for the Preparation of DOTA-Like Chelating Agents Chem. Eur. J. 2012, 18, 7834-7841. The chelate site was dispersed in 0.1 mol/L sodium acetate buffer (pH 6.0) as a solvent to give a dispersion containing 1.7 mmol/L chelate site. A reaction mixture of the solution. (0.004 mL), and $^{225}$Ac ion-containing solution (0.2 mol/L aqueous hydrochloric acid solution, radioactivity concentration 1225 MBq/mL, prepared from one produced by Oak Ridge National Laboratory, liquid amount: 0.004 mL) 4.9 MBq (calculated by attenuation from the radioactivity at test date and time), and 0.1 mol/L sodium acetate buffer (pH 6.0, 0.06 mL) as a source of radioactive metal was reacted under heating conditions to give a $^{225}$Ac complex solution. The molar ratio of the chelate site and the radioactive metal ion was chelate site:$^{225}$Ac ion=about 670:1, and the heating temperature of the reaction mixture was set to 70° C., and the heating time was set to 30 min.

L1-5

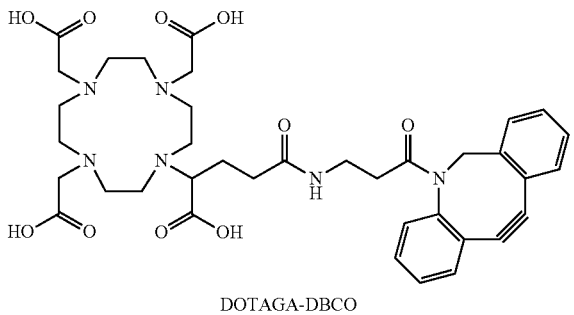

DOTAGA-DBCO

The radiochemical purity of the obtained $^{225}$Ac complex was measured in the same manner as in Example 1. As a result, the radiochemical purity of the $^{225}$Ac complex was 85%. The obtained $^{225}$Ac complex solution was directly used for the next labeling step.

(2. Radiolabeling Step)

A solution of the $^{225}$Ac complex obtained in the aforementioned (1. chelating agent synthesis step) and a solution containing the peptide-modified antibody (monovalent antibody; H01L03) produced in the same manner as in Production Example 2 except that the reaction was performed at room temperature for 60 min were mixed unpurified and click-reacted at 37° C. for 2 hr to give a $^{225}$Ac complex-labeled antibody. The amounts of the chelate site or the chelate site containing the $^{225}$Ac-labeled complex, and the peptide-modified antibody (monovalent antibody) were 68 nmol and 80 nmol, respectively, and the molar ratio of the first atomic group (DBCO) and the second atomic group (azide) was about 1:1.2.

Furthermore, a solution of the $^{225}$Ac complex-labeled antibody obtained by reacting at 37° C. for 2 hr was purified using ultrafiltration filter (manufactured by Merck, model number: UFC505096). The radiochemical purity of the $^{225}$Ac-labeled monovalent antibody after purification was 96%, and the radiochemical yield was 68%. The measurement method of the radiochemical purity and radiochemical yield of the $^{225}$Ac-labeled monovalent antibody was similar to that in Example 1.

Example 10: Production (HPLC Purification) of $^{89}$Zr-Labeled Anti-MUC5AC Humanized Antibody Using $^{89}$Zr-Labeled DOTAGA-DBCO (1-1. Chelating Agent Synthesis Step)

In this Example, a chelate site same as the chelate site shown by the above-mentioned formula (L1-5) was used. This chelate site was dispersed in DMSO solution to give a dispersion containing 2.0 mmol/L chelate site. A reaction mixture of the dispersion (0.150 mL), and $^{89}$Zr ion-containing solution (0.1 mol/L aqueous hydrochloric acid solution, radioactivity concentration 1335 MBq/mL, prepared from one produced by Nihon Medi-Physics Co., Ltd., liquid amount: 0.100 mL) 134 MBq, and 300 mmol/L gentisic acid-containing 780 mmol/L acetate buffer (0.050 mL) as a source of radioactive metal was reacted under heating conditions to give a $^{89}$Z complex solution. The molar ratio of the chelate site and the radioactive metal ion was chelate site:$^{89}$Z ion=about 3333:1, and the heating temperature of the reaction mixture was set to 70° C., and the heating time was set to 60 min.

The radiochemical purity of the obtained $^{89}$Zr complex was measured by the following method. That is, a part of the $^{89}$Zr complex solution was developed by thin layer chromatography (manufactured by Agilent, model number: SGI0001, developing solvent: acetonitrile/water mixed solution (volume ratio 1:1)), and then measured by radio γ-TLC Analyzer (manufactured by raytest, MODEL GITA Star PS). The percentage of the radioactivity (count) of the peak detected near the origin with respect to the detected total radioactivity (count) was defined as the radiochemical purity (%) of the $^{89}$Zr complex. As a result, the radiochemical purity of the $^{89}$Zr complex was 98%.

(1-2. $^{89}$Zr Complex Purification Step)

The $^{89}$Zr complex solution obtained in the aforementioned (1-1. chelating agent synthesis step) was collected by high performance liquid chromatography (HPLC), and unreacted DOTAGA-DBCO was removed. The solvent was evaporated from the obtained collected solution to about 30 μL of the solution and the solution was used in the labeling step. The method for measuring the radiochemical yield (HPLC recovery rate) in the step of removing the unreacted substance of the $^{89}$Zr complex-labeled antibody was as follows. That is, the percentage of radioactivity in the collected solution was defined as the HPLC recovery rate (%) in the unreacted substance removal step with respect to the amount of radioactivity charged at the start of step (1-1).

The HPLC conditions were as follows, and fractions with a retention time of around 27 min were collected.

<HPLC Conditions>
detector: ultraviolet absorption spectrophotometer (measurement wavelength: 220 nm, 254 nm)/scintillation detector
column: XBridge C18 3.5 μm, 4.6×100 mm, manufactured by Waters
flow rate: 0.5 mL/min
area measurement range: 45 min after sample injection
mobile phase A: 10 mmol/L histidine buffer (pH 6.5)
mobile phase B: acetonitrile for liquid chromatography
mobile phase C: acetonitrile/water mixed solution (1:1)
mobile phase feed: concentration gradient was controlled by changing the mixing ratio of mobile phase A, mobile phase B and mobile phase C as follows

TABLE 18

| time (min) after injection | mobile phase A (vol %) | mobile phase B (vol %) | mobile phase C (vol %) |
|---|---|---|---|
| 0.0-40.0 | 90 → 50 | 10 → 50 | 0 |
| 40.0-40.1 | 50 → 1 | 50 → 99 | 0 |
| 40.1-45.0 | 1 | 99 | 0 |
| 45.1-46.0 | 1 → 0 | 99 → 10 | 0 → 90 |
| 46.0-50.0 | 0 | 10 | 90 |

TABLE 18-continued

| time (min) after injection | mobile phase A (vol %) | mobile phase B (vol %) | mobile phase C (vol %) |
|---|---|---|---|
| 50.0-50.1 | 0 → 90 | 10 | 90 → 0 |
| 50.1-55.0 | 90 | 10 | 0 |

(2. Radiolabeling Step)

A solution of the $^{89}$Zr complex obtained by each of the aforementioned steps and a solution containing the peptide-modified antibody (monovalent antibody; H01L03) produced in the same manner as in Production Example 2 were mixed and click-reacted at 37° C. for 1.5 hr to give a $^{89}$Zr complex-labeled antibody. The amounts of the chelate site containing the $^{89}$Zr-labeled complex, and the peptide-modified antibody (monovalent antibody) were 73 µmol and 50 nmol, respectively, and the molar ratio of the first atomic group (DBCO) and the second atomic group (azide) was about 1:685.

Furthermore, a solution of the $^{89}$Zr complex-labeled antibody obtained by reacting at 37° C. for 1.5 hr was purified using ultrafiltration filter (manufactured by Merck, model number: UFC505096). The radiochemical purity of the $^{89}$Zr complex-labeled antibody after purification was 95%, and the radiochemical yield was 50%. The measurement method of the radiochemical purity and radiochemical yield of the $^{89}$Zr complex-labeled antibody was as follows. That is, thin layer chromatography (manufactured by Agilent, model number: SGI0001, developing solvent was mixed solution of acetonitrile:0.1 mmol/L EDTA solution (volume ratio 1:1)) was measured by radio γ-TLC Analyzer (manufactured by raytest, MODEL GITA Star PS), and the percentage of the radioactivity (count) of the peak detected near the origin to the total radioactivity (count) detected was defined as the radiochemical purity (%). In addition, the percentage of the radioactivity recovered after ultrafiltration purification relative to the total radioactivity added at the start of the labeling step was defined as the radiochemical yield (%).

Example 11: Stability Evaluation of Each $^{89}$Zr- or $^{225}$Ac-Labeled Anti-MUC5AC Humanized Antibody in Human or Mouse Plasma The $^{89}$Zr-labeled anti-MUC5AC humanized antibody prepared using $^{89}$Zr-labeled DOTAGA-DBCO was produced according to Example 10. The $^{89}$Zr-labeled anti-MUC5AC humanized antibody prepared using $^{89}$Zr-labeled DOTA-Bn-DBCO was produced according to Example 10 except that the chelate site shown by the aforementioned formula (L1-4) was used as the chelate site.

The $^{225}$Ac-labeled anti-MUC5AC humanized antibody prepared using $^{225}$Ac-labeled DOTA-Bn-DBCO was produced according to Example 2. The $^{225}$Ac-labeled anti-MUC5AC humanized antibody prepared using $^{22}$Ac-labeled DOTAGA-DBCO was produced according to Example 9.

As the solvent, 0.1 M sodium acetate buffer (pH 6.0) was used in all cases.

Various $^{89}$Zr-labeled antibodies and $^{225}$Ac-labeled antibodies were mixed with human or mouse plasma, and the stability at each elapsed time point during incubation at 37° C. was evaluated by cellulose acetate membrane electrophoresis. In addition, to evaluate degradation products in plasma other than the $^{89}$Zr-labeled antibody and $^{225}$Ac-labeled antibody, cellulose acetate membrane electrophoresis was performed by separately mixing each compound with each plasma assuming elimination of $^{89}$Zr or $^{225}$Ac from each chelator and cleavage of each linker site. Cellulose acetate membrane electrophoresis was performed using each plasma sample collected from each time point of incubation, and the cellulose acetate membrane was exposed to an imaging plate after completion of the electrophoresis. The exposed imaging plate was read by a scanner-type image analyzer (manufactured by GE Healthcare, model number: Typhoon-7000), and the radiochemical purity of various $^{89}$Zr-labeled antibodies and $^{225}$Ac-labeled antibodies was quantified and evaluated using an imaging analysis software (manufactured by GE Healthcare, software name: ImageQuant). The compositions of the evaluation samples are shown in Table 19. The percentage of the radioactivity (count) of the peak corresponding to each labeled antibody with respect to the detected total radioactivity (count) was defined as the radiochemical purity (%).

TABLE 19

RI-labeled anti-MUC5AC humanized antibody prepared using RI-labeled DOTA-Bn-DBCO

| evaluation compound (radiochemical purity %) | mixed sample | radioactivity concentration at start of incubation |
|---|---|---|
| $^{89}$Zr-labeled antibody (94%) | mouse plasma human plasma | 2.7 MBq/mL 3.4 MBq/mL |
| $^{225}$Ac-labeled antibody (77%) | mouse plasma human plasma | 2 kBq/mL | n = 3

TABLE 20

RI-labeled anti-MUC5AC humanized antibody (n = 3) prepared using RI-labeled DOTAGA-DBCO

| evaluation compound (radiochemical purity %) | mixed sample | radioactivity concentration at start of incubation |
|---|---|---|
| $^{89}$Zr-labeled antibody (94%) | mouse plasma human plasma | 0.4 MBq/mL |
| $^{225}$Ac-labeled antibody (100%) | mouse plasma human plasma | 1.6 kBq/mL | n = 3

With regard to the RI-labeled anti-MUC5AC humanized antibody prepared using RI-labeled DOTA-Bn-DBCO, the radiochemical purity of plasma samples sampled immediately after the incubation time for stability evaluation and measured by thin layer chromatography was 94% in mouse plasma and 95% in human plasma. Finally, the radiochemical purity when incubated for 378 hr was not less than 70% for both. The graph showing the results is the upper panel of FIG. 22A.

The radiochemical purity of the $^{225}$Ac-labeled antibody subjected to this evaluation was 77%, showing a differanve from the radiochemical purity of plasma samples sampled immediately after the incubation time for stability evaluation and measured by thin layer chromatography (mouse: 90%, human: 80%). It was considered that some solid component was remained to the origin and the radiochemical purity obtained was lower than the actual value. Finally, the radiochemical purity when incubated for 168 hr was not less than 60% for both. The graph showing the results is the upper panel of FIG. 22B.

With regard to the RI-labeled anti-MUC5AC humanized antibody prepared using RI-labeled DOTAGA-DBCO, the radiochemical purity of the $^{89}$Zr-labeled antibody subjected to this evaluation was 94%, and the values were generally the same as the radiochemical purity (mouse: 99%, human: 99%) of the plasma sample measured immediately after the incubation time for stability evaluation. Finally, the radiochemical purity when incubated for 336 hr was not less than 85% for both. The graph showing the results is the lower panel of FIG. 22A.

The radiochemical purity of the $^{225}$Ac-labeled antibody subjected to this evaluation was 100%, and the values were generally the same as the radiochemical purity (mouse: 97%, human: 100%) of the plasma sample measured immediately after the incubation time for stability evaluation. Finally, the radiochemical purity when incubated for 336 hr was not less than 80% for both. The graph showing the results is the lower panel of FIG. 22B.

Figure 23:
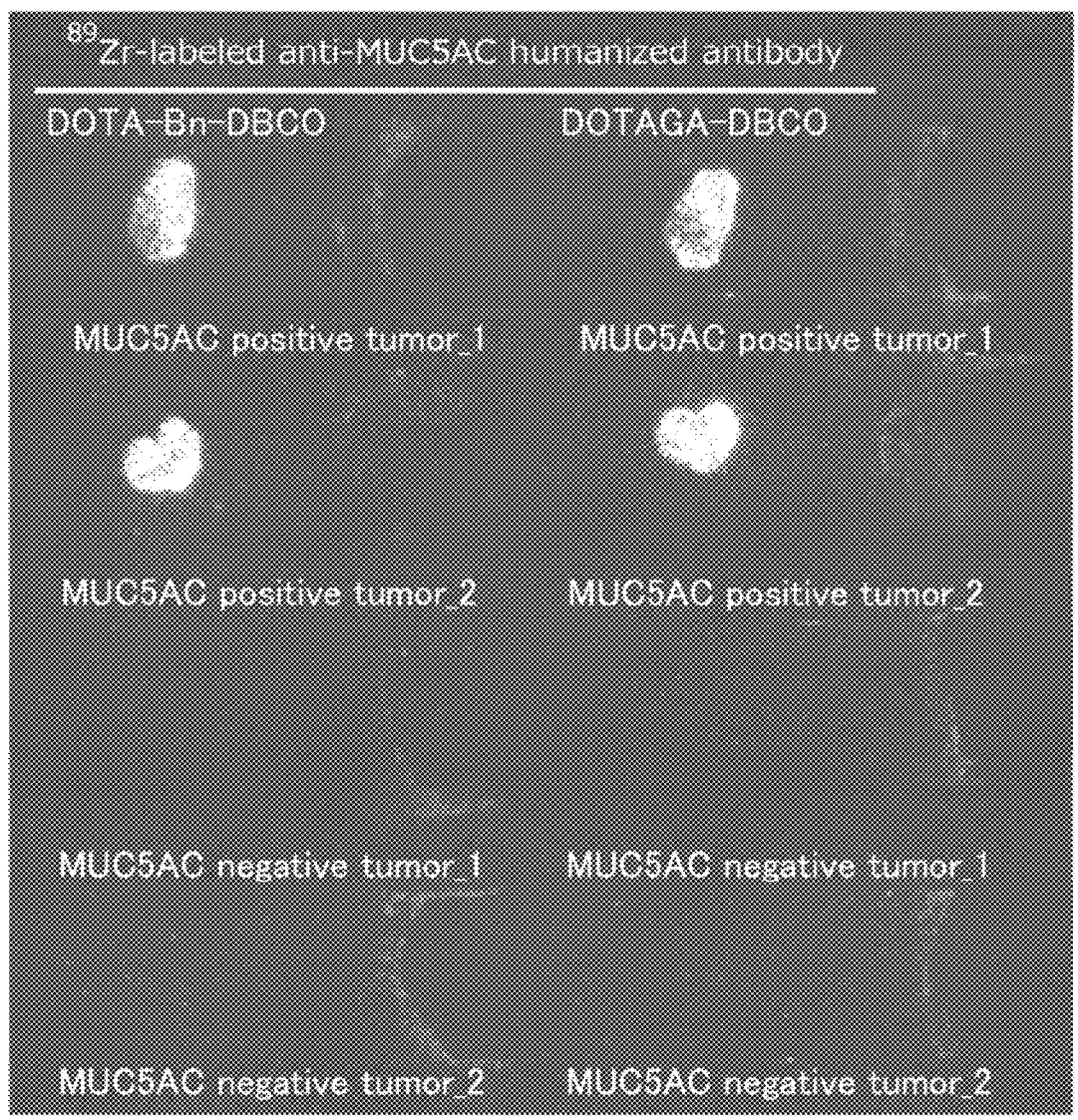
FIG. 23 is an image showing the results of the binding ability of each $^{89}$Zr-labeled antibody by in vitro ARG.
Figure 24:
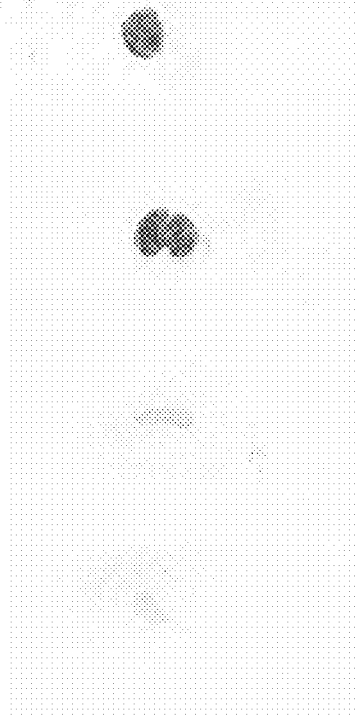
FIG. 24 is an image showing the results of the binding ability of $^{225}$Ac-labeled antibody by in vitro ARG.

Example 12: Binding Property and Specificity of RI-Labeled Anti-MUC5AC Humanized Antibody to MUC5AC RI-labeled anti-MUC5AC humanized antibody prepared using $^{225}$Ac or $^{89}$Zr-labeled DOTAGA-DBCO was produced according to Example 9 and Example 10. The RI-labeled anti-MUC5AC humanized antibody prepared using $^{89}$Zr-labeled DOTA-Bn-DBCO was produced according to Example 11. Using these RI-labeled anti-MUC5AC humanized antibodies, the binding property and specificity of each RI-labeled antibody to MUC5AC was evaluated by in vitro ARG. The evaluation of the specificity was performed according to Example 4-3 except that the above-mentioned RI-labeled anti-MUC5AC humanized antibody was used as the test substance. Images of the results of the $^{89}$Zr-labeled antibody are shown in FIG. 23, and the results of the $^{225}$Ac-labeled antibody are shown in FIG. 24. When the $^{89}$Zr-labeled antibody was used, an ROI was set for each whole section of the MUC5AC positive tumor section and the negative tumor section, and the measured value in the ROI was used to calculate the binding ratio to the MUC5AC positive tumor and the negative tumor. When the $^{225}$Ac-labeled antibody was used, a plurality of small ROIs were set in the tumor tissues of the MUC5AC positive tumor section and the negative tumor section, and the mean was used to calculate the binding ratio to the MUC5AC positive tumor and the negative tumor. As a result, the RI-labeled anti-MUC5AC humanized antibody prepared using $^{225}$Ac-labeled DOTAGA-DBCO showed a 6.5-fold binding ratio. The RI-labeled anti-MUC5AC humanized antibody prepared using $^{89}$Zr-labeled DOTAGA-DBCO showed a 138-fold binding ratio. The RI-labeled anti-MUC5AC humanized antibody prepared using $^{89}$Zr-labeled DOTA-Bn-DBCO showed a 151-fold binding ratio. It was confirmed that the $^{89}$Zr or $^{225}$Ac-labeled anti-MUC5AC humanized antibody prepared using $^{89}$Zr or $^{225}$Ac-labeled DOTAGA-DBCO, and the $^{89}$Zr-labeled anti-MUC5AC humanized antibody prepared using $^{89}$Zr-labeled DOTA-Bn-DBCO maintained the binding property and specificity to MUC5AC.

Example 13: PET-CT Imaging of $^{89}$Zr-Labeled Anti-MUC5AC Humanized Antibodies Prepared Using $^{89}$Zr-Labeled DOTA-Bn-DBCO and DOTAGA-DBCO $^{89}$Zr-labeled antibodies were produced using $^{89}$Zr-labeled DOTA-Bn-DBCO and DOTAGA-DBCO and according to Example 10, each was administered to a tumor-bearing mouse, and evaluation using PET-CT imaging was performed.

Human pancreatic cancer-derived cell line SW1990 (0.7× $10^7$ cells) which is a MUC5AC high expression tumor cell line was subcutaneously administered to Balb/c nude mouse (male) from the flank to the back thereof. When the tumor volume reached about 150-300 mm$^3$ after transplantation, the $^{89}$Zr-labeled anti-MUC5AC humanized antibodies were administered from the tail vein of the mice. The tumor volume was calculated from the following calculation formula.

tumor volume=(tumor minor axis$^2$×tumor major axis)/2

The radiochemical purity and animal information of the administered the $^{89}$Zr-labeled anti-MUC5AC humanized antibodies are shown in Table 21.

TABLE 21

Administered radioactivity amount and animal information (on administration of the $^{89}$Zr-labeled antibodies)

| name of antibody | $^{89}$Zr-labeled anti-MUC5AC humanized antibody | |
|---|---|---|
|  | DOTA-Bn | DOTAGA |
| tumor volume (mm$^3$) | 337 ± 142 | 335 ± 129 |
| body weight (g) | 21.6 ± 1.2 | 22.1 ± 0.8 |
| radiochemical purity (%) | 92% | 94% |
| administered radioactivity amount (MBq) | 4.6 ± 0.2 | 4.6 ± 0.0 |

(mean ± standard deviation, n = 4)

PET-CT imaging (small animal PET-CT apparatus: Si78, manufactured by Bruker) was performed under the conditions in the following Table. The time points for PET and CT imaging were 12, 48, 84, 168, 252 hr after administration. Image reconstruction was performed by the MLEM method for PET and the FBP method for CT. VOI analysis of the SUV (standardized uptake value) of the tumor and heart (blood), liver at each time point was performed, and the SUV profile was compared using the time activity curve.

TABLE 22

PET imaging and reconstruction conditions

| Isotope | 89-Zr |
|---|---|
| acquisition time | 600 sec |
| Energy window | 30% (357.7-664.3 keV) |
| PET image reconstruction | MLEM GPU 32 × 32 0.25 (Iterations: 12) |
| correction | Scatter, Randoms, Decay, Partial volume, Attenuation |

TABLE 23

CT imaging conditions

| Acquisition Mode | Static |
|---|---|
| Scanning Mode | Continuous (7 deg/s) |
| X-ray Source Filter | AL-1.0 mm |
| Pixel Size | 50 um |
| X-ray tube current | 771 uA |
| X-ray tube voltage | 65 kV |

Figure 25:
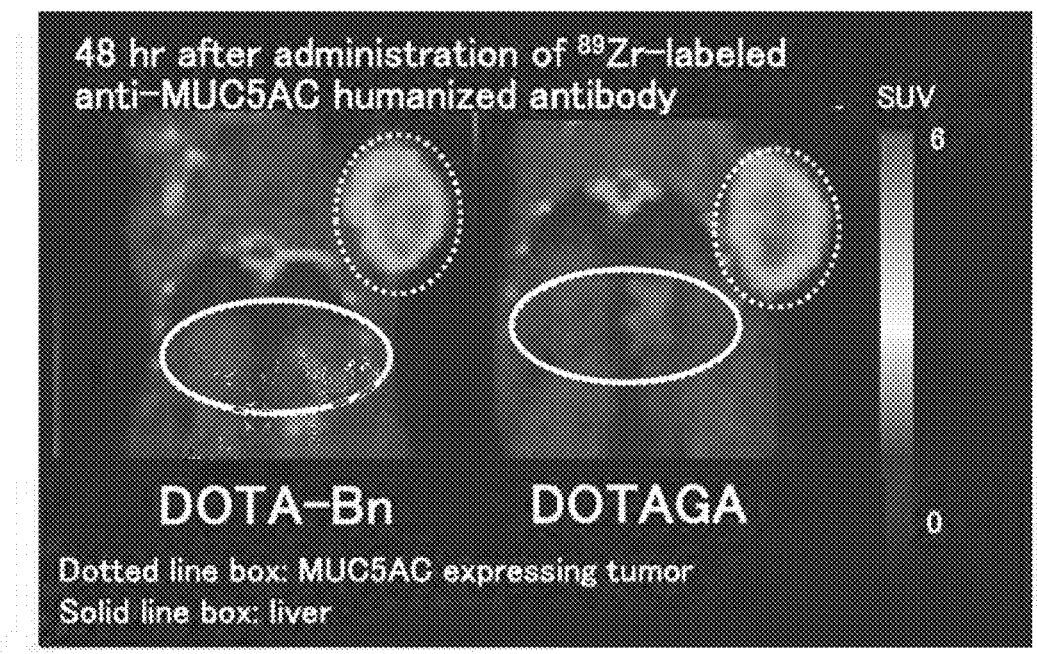
FIG. 25 is an image showing the results of PET-CT imaging 48 hr after administration of each $^{89}$Zr-labeled antibody.
Figure 26:
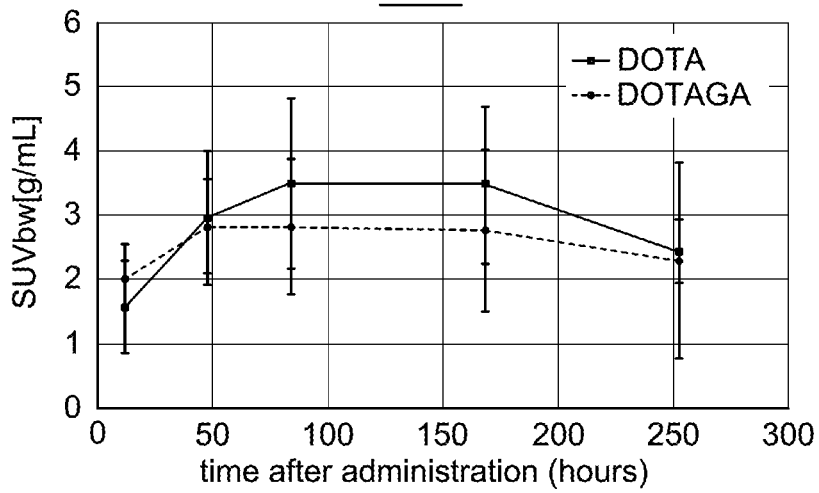
FIG. 26 shows graphs showing the results of VOI (volume of interest, three-dimensional ROI) analysis of the tumor (upper figure), heart (middle figure) and liver (lower figure) at each time point (12, 48, 84, 168 and 252 hr) in SPECT images of respective $^{89}$Zr-labeled antibodies prepared using $^{89}$Zr-labeled DOTA-Bn-DBCO (-■-) and $^{89}$Zr-labeled DOTAGA-DBCO ( ... ● ... ).
Figure 26:
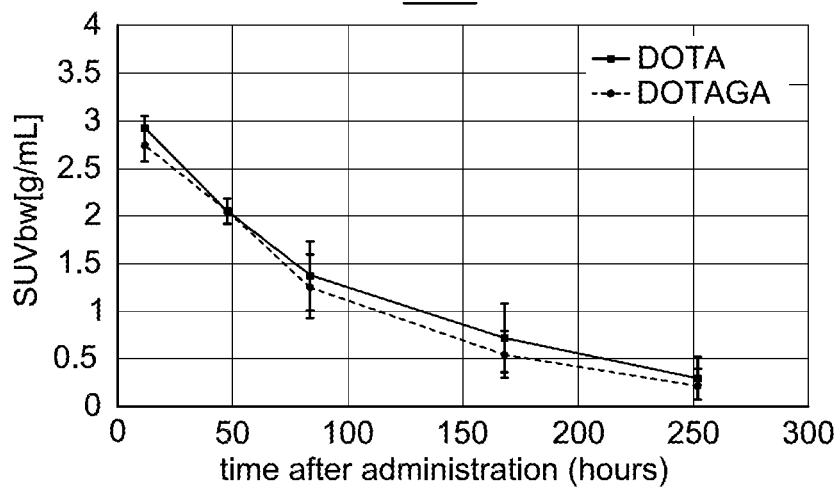
Figure 26:
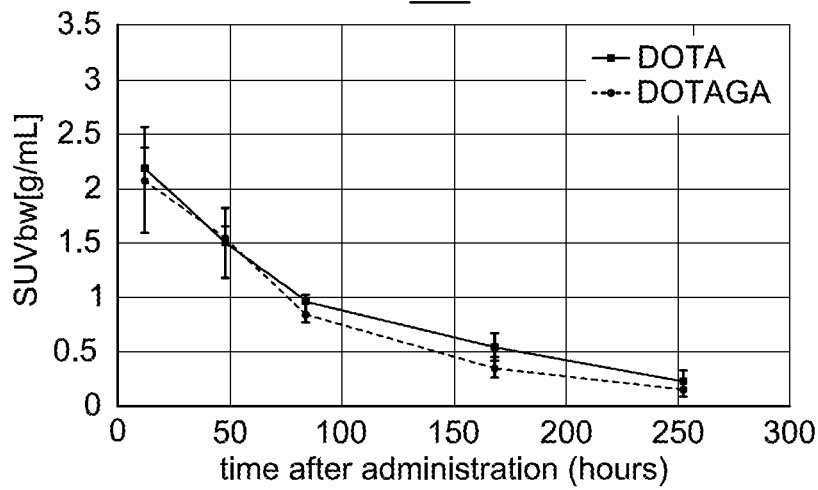
Figure 27:
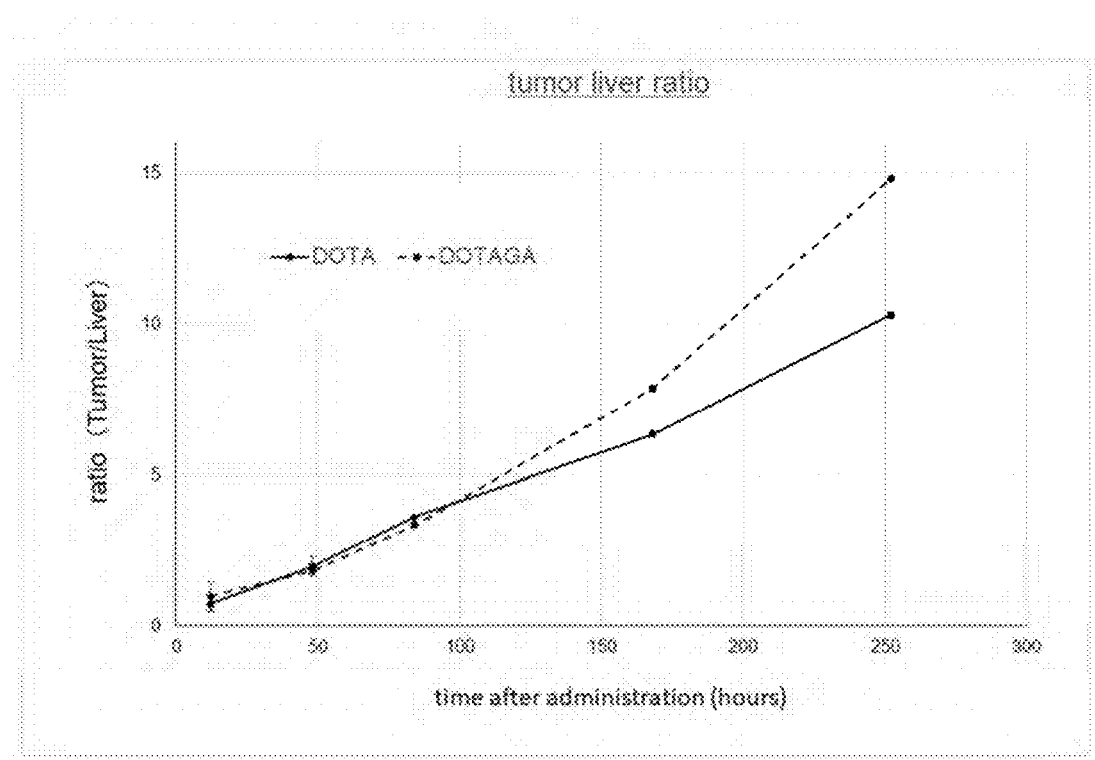
FIG. 27 is a graph showing the results of calculation of tumor-liver ratio from the accumulation at each time point (12, 48, 84, 168 and 252 hr) in the tumor and liver after administration of respective $^{89}$Zr-labeled antibodies prepared using $^{89}$Zr-labeled DOTA-Bn-DBCO (-●-) and $^{89}$Zr-labeled DOTAGA-DBCO ( ... ● ... ).

The results of performing PET-CT imaging 48 hr after $^{89}$Zr-labeled antibody administration are shown in FIG. 25. The results of VOI analysis of the tumor and heart (blood), liver at each time point are shown in FIG. 26. In addition, the results of tumor to liver ratio at each time point are shown in FIG. 27.

The maximum value of accumulation in tumor was not less than 2.8 as SUV, and the maximum value of tumor liver ratio 84 hr after administration was 3.6 for the $^{89}$Zr-labeled antibody prepared using $^{89}$Zr-labeled DOTA-Bn-DBCO, and 3.4 for the $^{89}$Zr-labeled antibody prepared using 89Zr-labeled DOTAGA-DBCO. A statistically significant difference was not found in each value.

It was confirmed that the accumulation of the $^{89}$Zr-labeled antibodies in the heart (blood) decreased with time, and that it almost disappeared from the blood 252 hr after administration. In addition, no statistically significant difference was found in accumulation in heart (blood) at each time point among the $^{89}$Zr-labeled antibodies. Similarly, it was confirmed that the accumulation of the $^{89}$Zr-labeled antibodies in the liver and muscle decreased with time, and no statistically significant difference was found in accumulation in each tissue at each time point among the $^{89}$Zr-labeled antibodies.

Example 14: Biodistribution Experiment of $^{89}$Zr-Labeled Anti-MUC5AC Humanized Antibodies Prepared Using $^{89}$Zr-Labeled DOTA-Bn-DBCO and DOTAGA-DBCO For confirmation of more detailed pharmacokinetics, $^{89}$Zr-labeled antibodies prepared using $^{89}$Zr-labeled DOTA-Bn-DBCO and DOTAGA-DBCO were administered to tumor-bearing mice, and biodistribution experiment was performed 20, 68, 188 hr after administration. The $^{89}$Zr-labeled antibodies were produced according to Example 10 as in Example 13.

For the biodistribution experiment, the $^{89}$Zr-labeled antibodies were administered from the tail vein to tumor-bearing mice prepared by a method similar to that in Example 4-2. The radiochemical purity and animal information of the administered the $^{89}$Zr-labeled anti-MUC5AC humanized antibodies are shown in Table 24. The radioactivity amount of about 5 MBq was administered to all groups.

TABLE 24

| Administered radioactivity amount and animal information (on administration of the $^{89}$Zr-labeled antibodies) | | | | | | |
|---|---|---|---|---|---|---|
| name of antibody | $^{89}$Zr-labeled anti-MUC5AC humanized antibody | | | | | |
| | DOTA-Bn | | | DOTAGA | | |
| time point (hr) | 20 | 68 | 188 | 20 | 68 | 188 |
| tumor volume (mm³) | 409 ± 78 | 441 ± 150 | 484 ± 149 | 482 ± 124 | 513 ± 206 | 505 ± 155 |
| body weight (g) | 21.5 ± 1.2 | 22.0 ± 0.5 | 22.7 ± 1.4 | 21.2 ± 1.1 | 22.5 ± 0.7 | 22.4 ± 1.2 |
| radiochemical purity (%) | | 97% | | | 95% | |

(mean ± standard deviation, n = 4)

The tumor-bearing mice were reared in a metabolic cage after administration of the $^{89}$Zr-labeled antibodies, and feces and urine excreted up to each time point (20, 68, 188 hr after administration) were collected. The tumor-bearing mice were euthanized at each time point by exsanguination under isoflurane anesthesia. Tumor, blood, and normal organs (including the rest of the body) were collected and weighed.

Figure 28D:
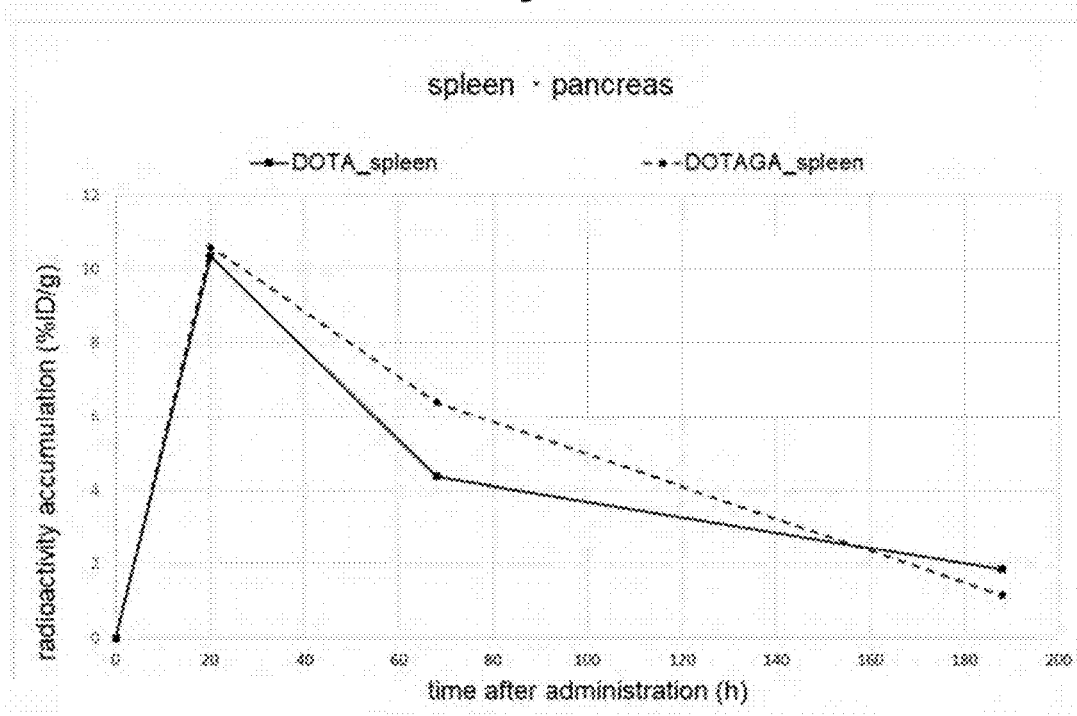
FIG. 28D shows graphs showing the results of the amount of radioactivity per unit weight (% ID/g) in each organ in the biodistribution after 20, 68 and 188 hr from the administration of respective $^{89}$Zr-labeled antibodies prepared using $^{89}$Zr-labeled DOTA-Bn-DBCO (-■-) and $^{89}$Zr-labeled DOTAGA-DBCO ( ... ● ... ). The results of spleen and pancreas are respectively shown.
Figure 29:
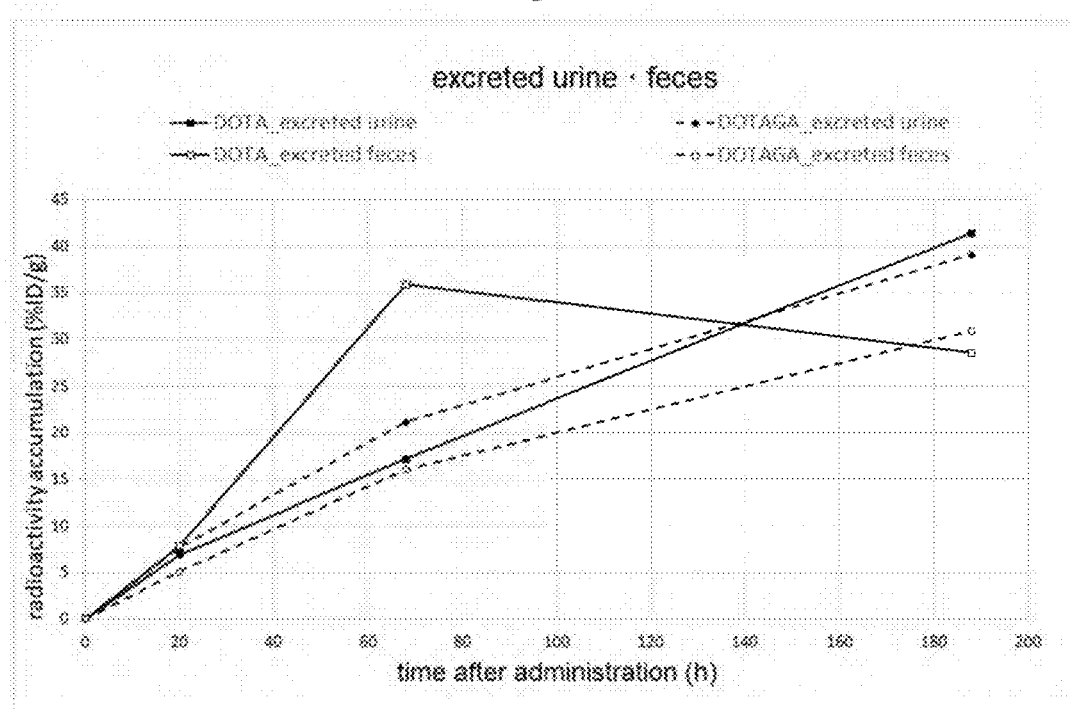
FIG. 29 is a graph showing the time-course changes in the rate of radioactivity accumulated (% ID) of excreted feces (-□-, ... ○ ... ) and excreted urine (-■-, ... ● ... ) after administration of respective $^{89}$Zr-labeled antibodies prepared using $^{89}$Zr-labeled DOTA-Bn-DBCO (-■-, -□-) and $^{89}$Zr-labeled DOTAGA-DBCO ( . . . ● . . . , . . . ○ . . . ).

The amount of radioactivity in excreted feces and excreted urine in addition to the weighed organs was measured (γ-ray well scintillation measuring apparatus: JDC-1712, manufactured by Hitachi Aloka Medical, Ltd.). The radioactivity accumulation rate (% ID) with respect to the dose was calculated from the radioactivity amount (count) of each organ (including excreted feces and excreted urine), and the amount of accumulated radioactivity (% ID/g) was calculated as the rate of radioactivity accumulation per organ weight. The results showing changes in the amount of radioactivity accumulated in tumor tissue and each organ over time are shown in FIG. 28 A-D. The radioactivity accumulation rate (% ID) with respect to the dose was calculated from the radioactivity accumulation (count) in excreted feces and excreted urine, and the results showing changes over time are shown in FIG. 29.

The amount of radioactivity accumulated in the tumor was the highest 188 hr after administration in the $^{89}$Zr-labeled antibody prepared using $^{89}$Zr-labeled DOTA-Bn-DBCO and the highest 68 hr after administration in the $^{89}$Zr-labeled antibody prepared using $^{89}$Zr-labeled DOTAGA-DBCO. The amount of radioactivity accumulated at that time showed not less than 20% ID/g. The time course changes in the radioactivity accumulation in blood tended to decrease similarly in the $^{89}$Zr-labeled antibodies, and the blood clearance can be judged to be of the same level. Regarding excretion, the radioactivity accumulation rate in feces and urine was not less than 65% ID 188 hr after administration. The radioactivity accumulated in the normal tissue was the highest 20 hr after administration and the radioactivity accumulation tended to decrease after 20 hr. The normal tissues with high radioactivity accumulation 20 hr after administration were liver, lung, and spleen in this order.

Example 15: Efficacy Evaluation of $^{225}$Ac-Labeled Anti-MUC5AC Humanized Antibody Prepared Using $^{225}$Ac-Labeled DOTAGA-DBCO A $^{225}$Ac-labeled antibody prepared using $^{225}$Ac-labeled DOTAGA-DBCO was administered to tumor-bearing mice, and study was conducted to confirm the tumor growth inhibitory effect. The $^{225}$Ac-labeled antibody was produced according to Example 9. The tumor-bearing mice were prepared in the same manner as in Example 4-2.

The $^{225}$Ac-labeled antibody was administered to tumor-bearing mice at a radioactivity amount of 5 kBq/mouse or 10 kBq/mouse, and the property of the $^{225}$Ac-labeled antibody was evaluated. In addition, a group (antibody control group) was provided to which a solution containing only the anti-MUC5AC humanized antibody dissolved in 0.1 M sodium acetate buffer (pH 6.0) was administered. Each group contained 6 mice, and observation of general condition, measurement of the body weight and tumor volume were measured for 4 weeks after administration. The results are shown in Table 25.

TABLE 25

Administered radioactivity amount and animal information (on administration of the $^{225}$Ac-labeled antibodies)

|  | antibody control group | $^{225}$Ac-labeled anti-MUC5AC humanized antibody administration group | |
| --- | --- | --- | --- |
| administered radioactivity amount (kBq) | — | 5 | 10 |
| tumor volume (mm$^3$) | 165 ± 43 | 161 ± 36 | 161 ± 29 |
| body weight (g) | 20.7 ± 0.7 | 20.8 ± 1.0 | 21.3 ± 1.2 |

Figure 30:
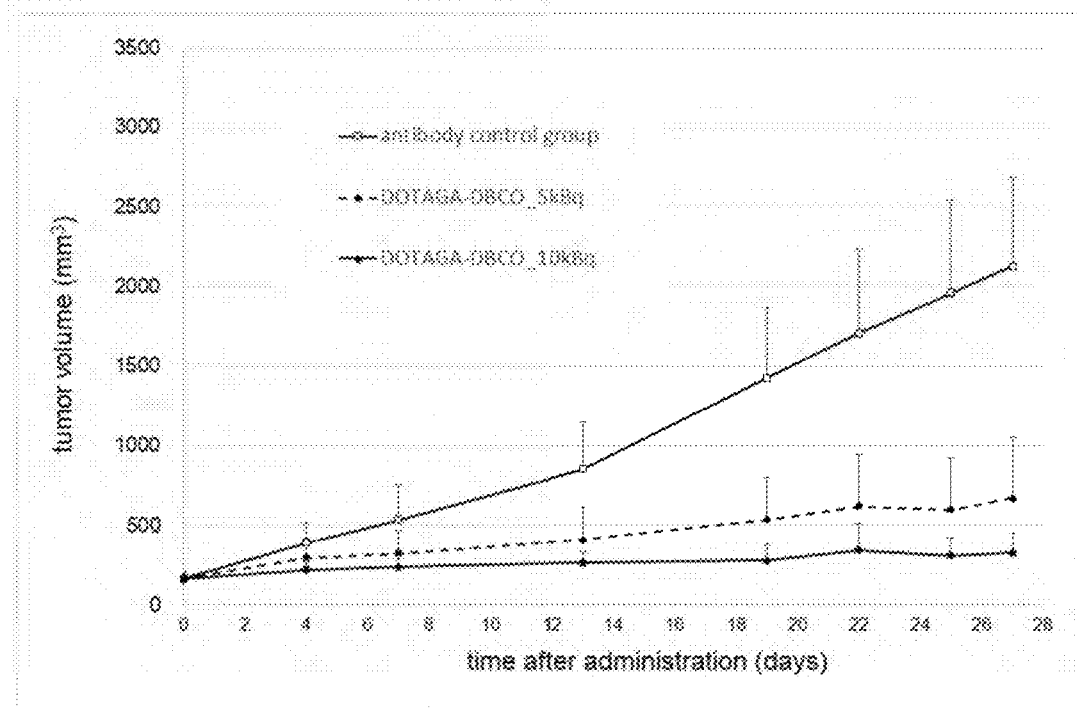
FIG. 30 shows graphs showing the time-course changes in the tumor volume (upper graph) and body weight (lower graph) after administration of a $^{225}$Ac-labeled antibody prepared using $^{225}$Ac-labeled DOTAGA-DBCO to tumor-bearing mice at administered radioactivity 5 kBq/mouse or 10 kBq/mouse.
Figure 30:
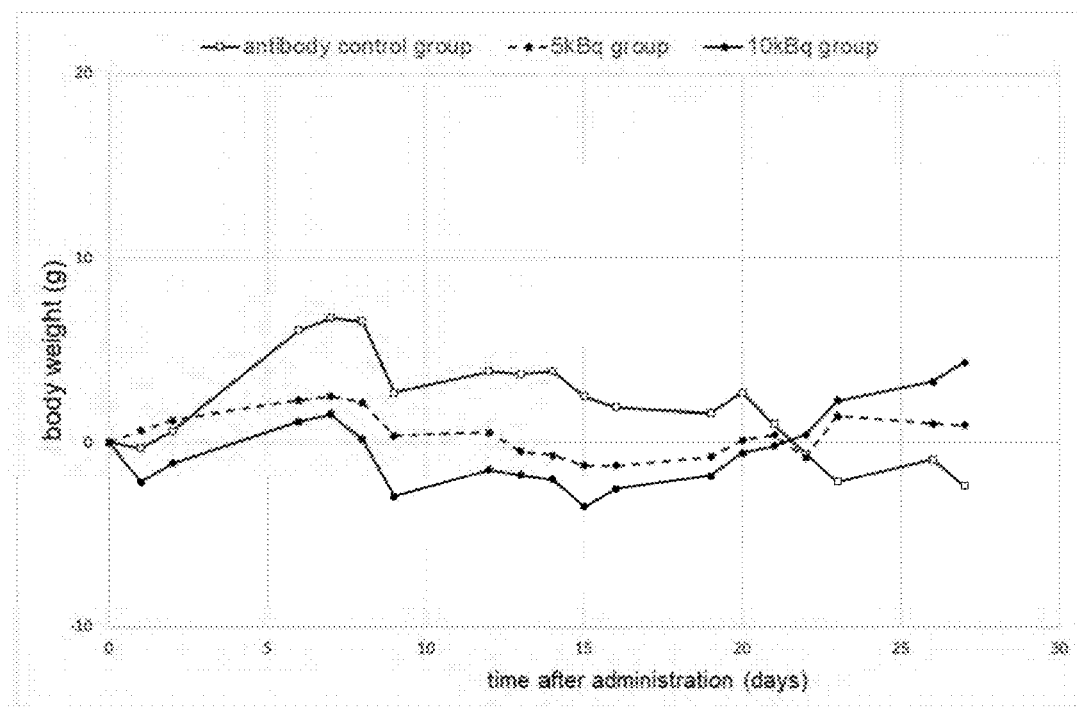

The result of confirming the changes in tumor volume with time is shown in FIG. 30 (A). Tumor growth was statistically significantly suppressed at any dose in the $^{225}$Ac-labeled antibody administration group as compared with the antibody control group, and the tumor growth inhibitory effect by the administration of the $^{225}$Ac-labeled antibody was confirmed.

An autopsy was performed on the last day of the observation period, and tumors were collected and weighed. The comparison results of the tumor weight are shown in Table 26. It was found that the tumor weight was statistically significantly low in all $^{225}$Ac-labeled antibodies administration groups as compared with the antibody control group.

TABLE 26

Comparison of tumor weight

|  | antibody control group | $^{225}$Ac-labeled anti-MUC5AC humanized antibody administration group | |
| --- | --- | --- | --- |
| administered radioactivity amount (kBq) | — | 5 | 10 |
| tumor weight (g) | 2.06 ± 0.42 | 0.75 ± 0.36* | 0.36 ± 0.15* | mean ± standard deviation,
n = 6 significance level:
*P < 0.05 vs antibody control group The results of confirmation of the changes in body weight over time are shown in FIG. 30(B). In the 10 kBq administration group in all $^{225}$Ac-labeled antibodies administration group, a decrease in the body weight was found in the early observation period; however, it was not below 0.9 in a relative ratio. In the late observation period, the body weight recovered to around that before administration.

An autopsy was performed on the last day of the observation period, and liver, kidney and spleen were collected and weighed. In all $^{225}$Ac-labeled antibody administration groups, a statistically significant decrease in the tissue weight was not found as compared with the antibody control group.

TABLE 27

Comparison of tissue weight

|  | antibody control group | $^{225}$Ac-labeled anti-MUC5AC humanized antibody administration group | |
| --- | --- | --- | --- |
| administered radioactivity amount (kBq) | — | 5 | 10 |
| liver (g) | 0.98 ± 0.09 | 1.02 ± 0.06 | 1.18 ± 0.10 |
| kidney (g) | 0.30 ± 0.02 | 0.34 ± 0.03 | 0.35 ± 0.03 |
| spleen (g) | 0.068 ± 0.012 | 0.073 ± 0.008 | 0.078 ± 0.007 |

Figure 31:
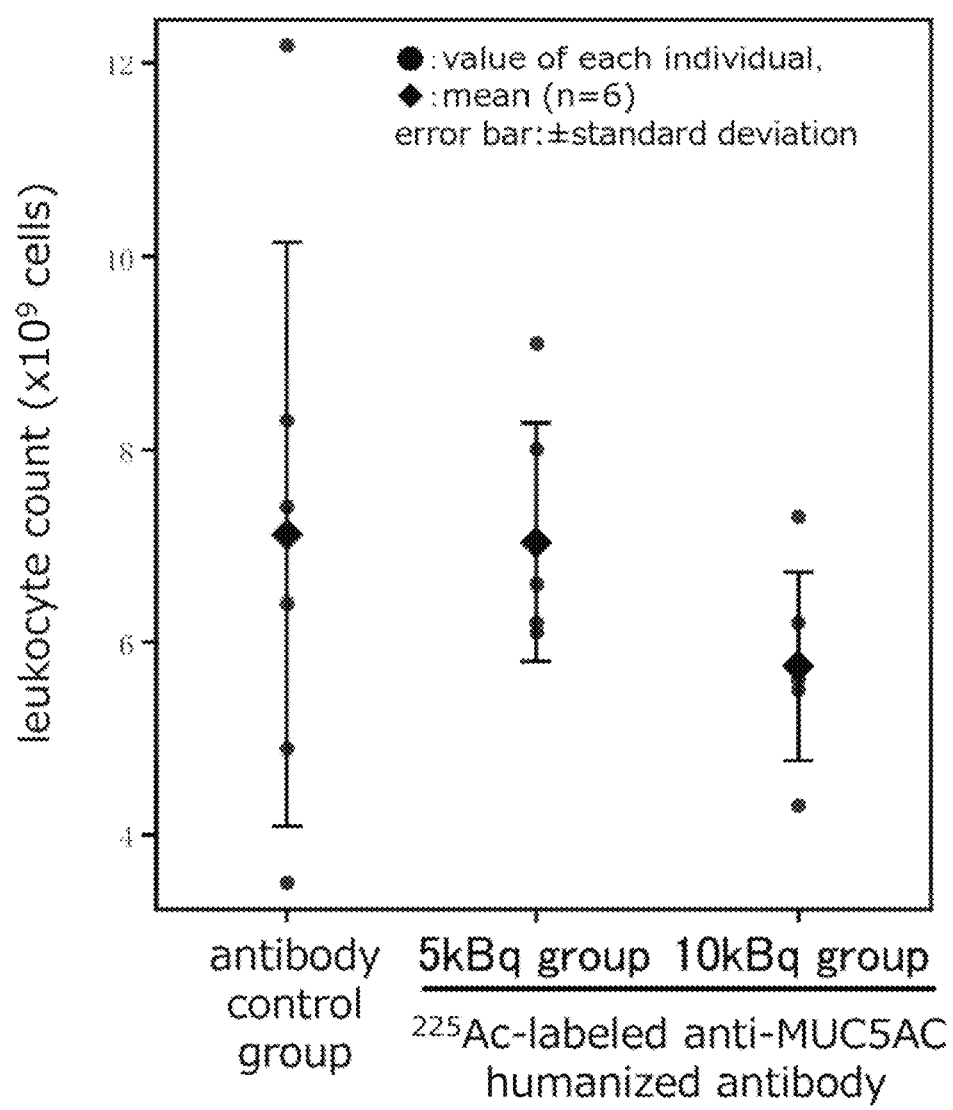
FIG. 31 is a graph showing the results of the blood toxicity (leukocyte count) in tumor-bearing mice after administration of a $^{225}$Ac-labeled antibody prepared using $^{225}$Ac-labeled DOTAGA-DBCO.
Figure 32:
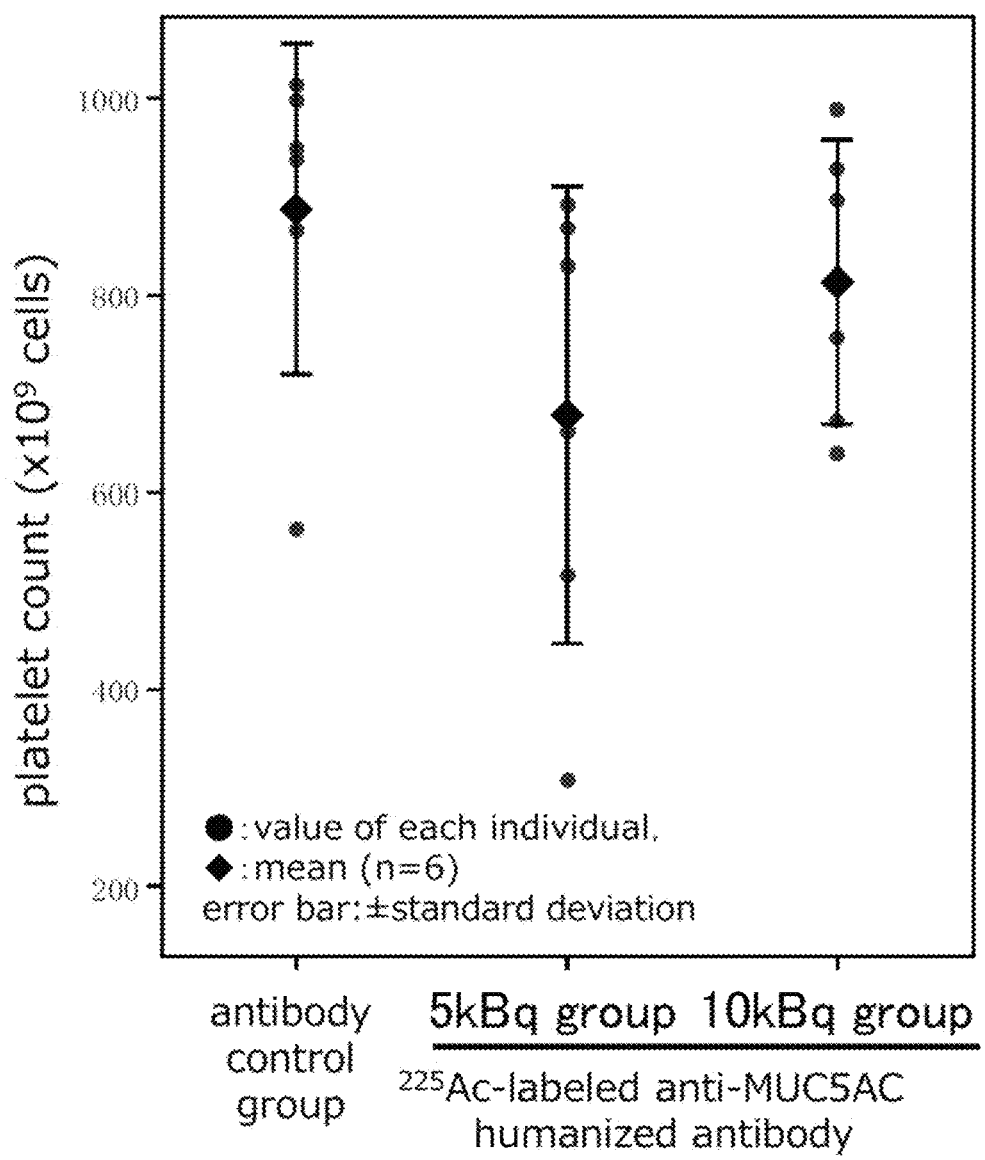
FIG. 32 is a graph showing the results of the blood toxicity (platelet count) in tumor-bearing mice after administration of a $^{225}$Ac-labeled antibody prepared using $^{225}$Ac-labeled DOTAGA-DBCO.
Figure 33:
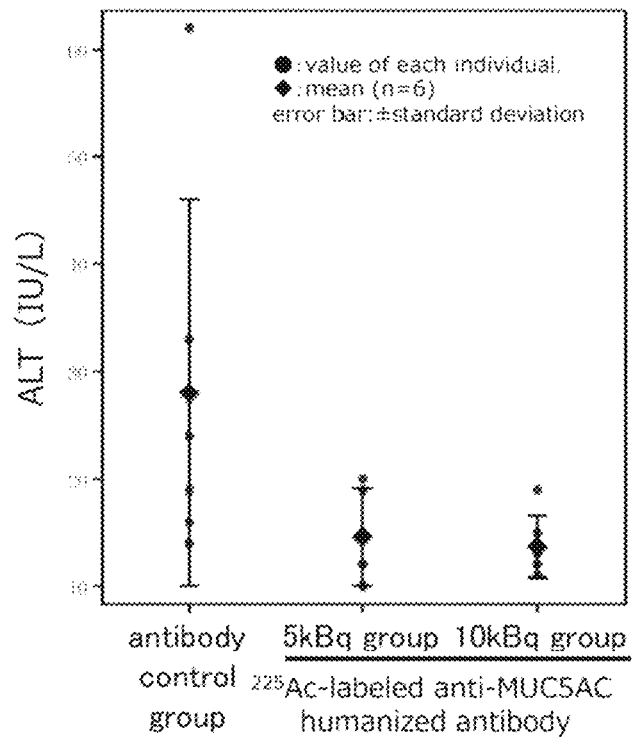
FIG. 33 is a graph showing the results of the hepatotoxicity (ALT, AST) in tumor-bearing mice after administration of a $^{225}$Ac-labeled antibody prepared using $^{225}$Ac-labeled DOTAGA-DBCO.
Figure 33:
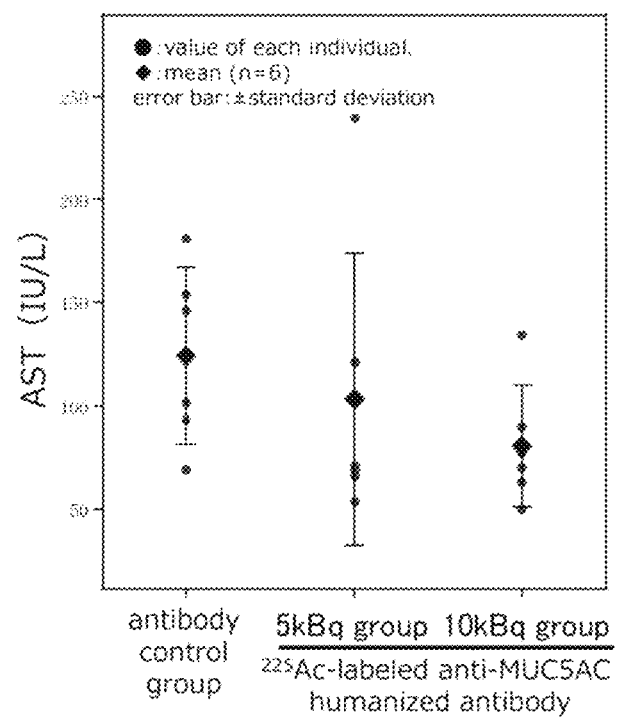
Figure 34:
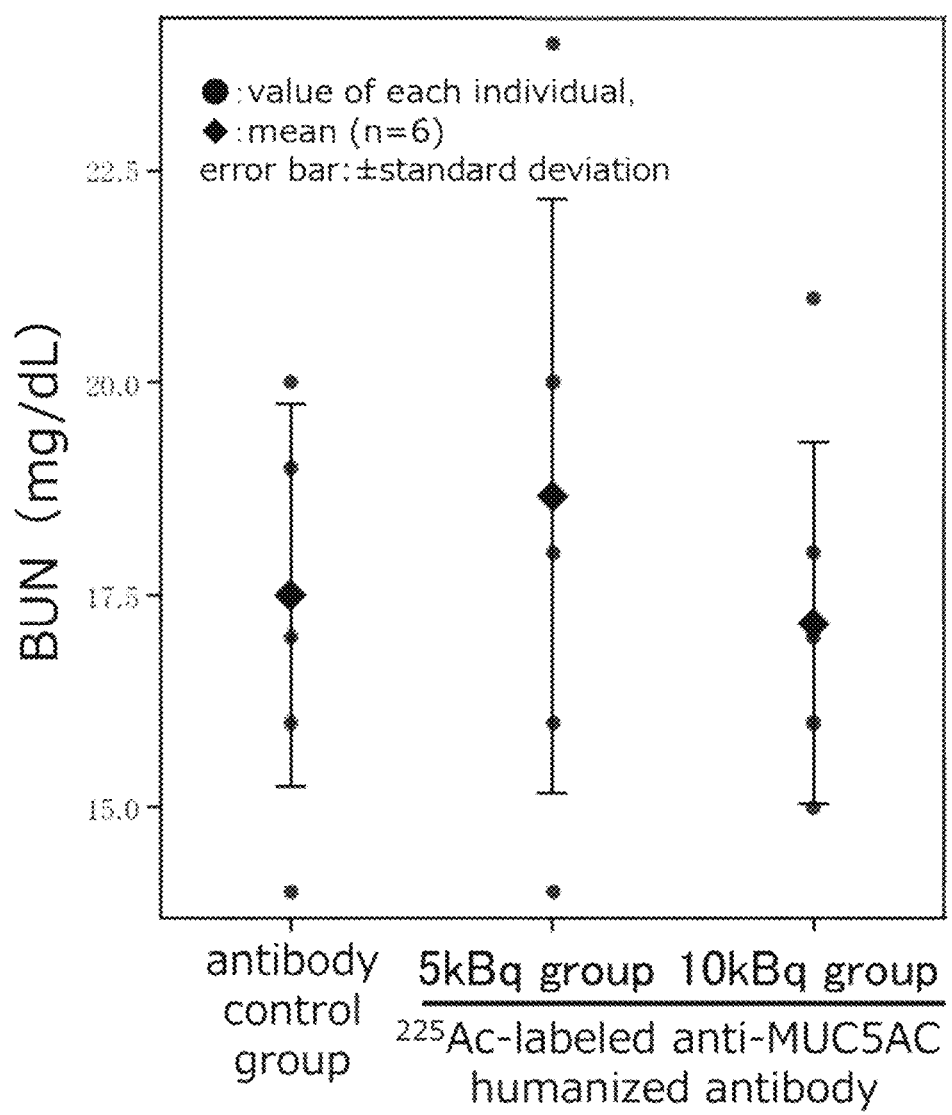
FIG. 34 is a graph showing the results of the kidney toxicity (BUN) in tumor-bearing mice after administration of a $^{225}$Ac-labeled antibody prepared using $^{225}$Ac-labeled DOTAGA-DBCO.

The results of hepatotoxicity and kidney toxicity are respectively shown in FIGS. 33 and 34. Since a statistically significant difference was not observed with respect to the antibody control group, it was suggested that this dose does not induce hepatotoxicity or kidney toxicity. The results of blood toxicity are shown in FIGS. 31 and 32. Since a statistically significant difference was not observed as compared with the antibody control group, it was suggested that this dose does not induce blood toxicity.

Example 16: Production of $^{89}$Zr Random Labeled Anti-MUC5AC Humanized Antibody ([$^{89}$Zr]Random-DFO-Anti-MUC5AC Humanized Antibody)

A peptide-modified antibody produced in the same manner as in Production Example 2 (monovalent antibody; H01L03) (0.1 mg, 0.7 nmol) and 1-(4-isothiocyanatophenyl)-3-[6,17-dihydroxy-7,10,18,21-tetraoxo-27-(N-acetyl-hydroxylamino)-6,11,17,22-tetraazaheptaeicosine]thiourea (p-SCN-Bn-DFO, Macrocyclics) (0.26 mg, 0.35 μmol) were blended in 0.1 M sodium hydrogen carbonate buffer and reacted at room temperature for 120 min. After completion of the reaction, the mixture was purified by ultrafiltration, and the solvent was substituted with 100 mmol arginine-containing 50 mmol histidine buffer (pH 6.1) (hereinafter RH buffer) to produce an anti-MUC5AC humanized antibody in which DFO is randomly bonded to the amino group of anti-MUC5AC humanized antibody (hereinafter "Random-DFO-anti-MUC5AC humanized antibody"). As a result of protein concentration measurement by Nano-Drop2000 (ThermoFisher), the protein concentration of Random-DFO-anti-MUC5AC humanized antibody solution was 1.12 mg/mL. The obtained Random-DFO-anti-MUC5AC humanized antibody solution (89.6 μL, 0.1 mg, 0.67 μmol) was mixed with 10 μL (11.8 MBq) of 89ZrCl3 solution and 301.6 μL of RH buffer to promote the complex formation reaction. After complex formation, purification was performed by ultrafiltration to obtain [$^{89}$Zr]Random-DFO-anti-MUC5AC humanized antibody. The radiochemical purity was calculated in the same manner as in Example 10, and the radiochemical purity was 97.3%. Moreover, the radiochemical yield was calculated based on the radioactivity at the start of the reaction, and the radiochemical yield was 43.0%.

Example 17: PET-CT Imaging of [$^{89}$Zr]Random-DFO-Anti-MUC5AC Humanized Antibody The [$^{89}$Zr]Random-DFO-anti-MUC5AC humanized antibody obtained in Example 16 was diluted with RH buffer and adjusted to a concentration of 1.27 MBq/22.5 μg protein/100 μL/mouse, administered to the tumor-bearing mice (n=3) produced in the same manner as in Example 4-2, and evaluation using PET-CT imaging was performed at 19, 42, 86, 158 hr after administration. The tumor volume of the animal subjected to this evaluation was calculated in the same manner as in Example 4-2. As a result, the mean of the tumor volume was 60.0±20.0 mm³. PET imaging conditions and image reconstruction method followed those in Example 13. VOI analysis of the SUV of the tumor and heart (blood), liver at each time point was performed, and the SUV profile was compared using the time activity curve.

Figure 35:
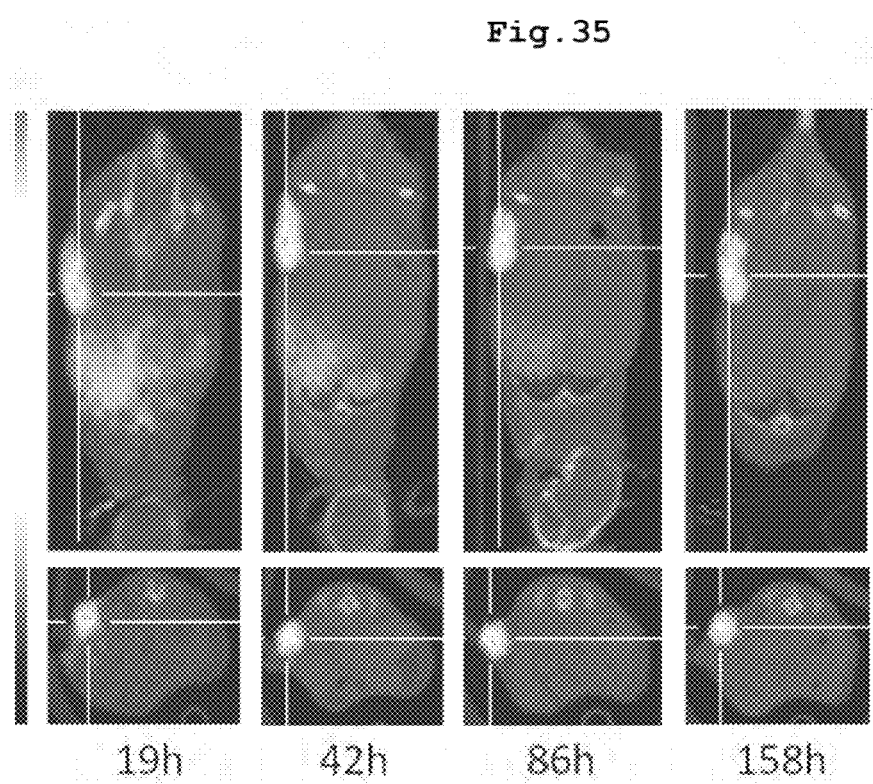
FIG. 35 shows the results of PET-CT imaging over time using a [$^{89}$Zr]Random-DFO-anti-MUC5AC humanized antibody.
Figure 36:
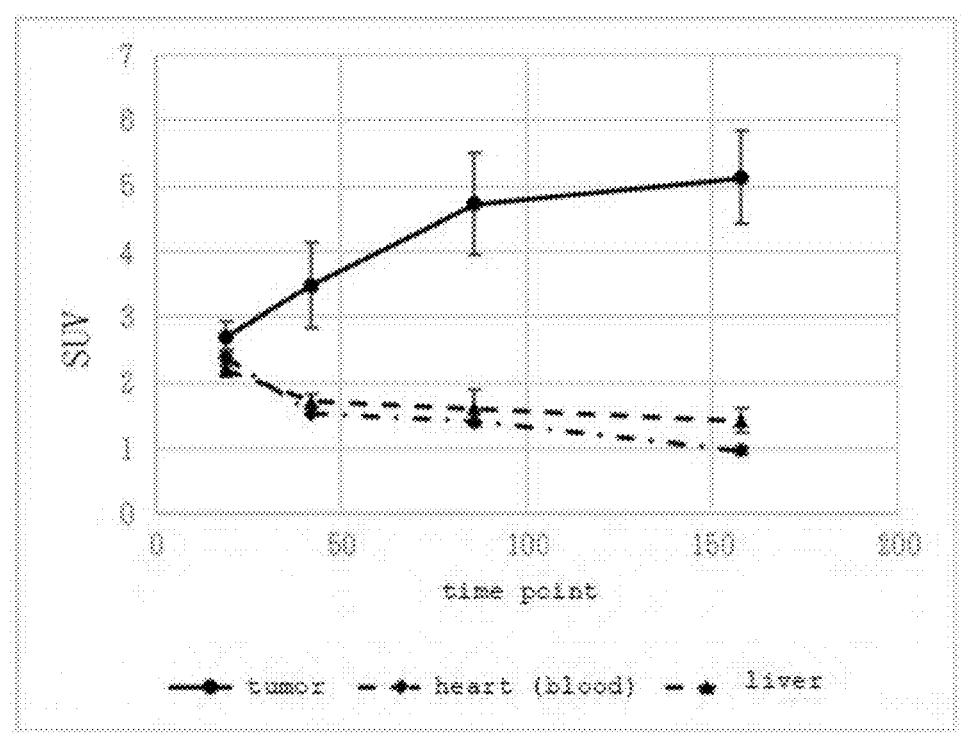
FIG. 36 is a graph showing the results of VOI (volume of interest, three-dimensional ROI) analysis of the tumor (-●-), heart (blood) ( . . . ■ . . . ) and liver ( . . . Δ . . . ) at each time point in PET images of a [$^{89}$Zr]Random-DFO-anti-MUC5AC humanized antibody.

The results of performing PET-CT imaging are shown in FIG. 35. The results of VOI analysis of the tumor, heart, and liver at each time point are shown in FIG. 36. From the results of VOI analysis, accumulation with time was found in tumor, mean of SUV was not less than 2.7 at any time point, and the maximum mean of SUV was 5.1 at 158 hr. It was confirmed that SUV in organs (heart (blood), liver) other than tumor decreases over time. The tumor to liver ratio of SUV at 158 hr after administration was 3.7.

Example 16: Biodistribution Experiment of [$^{89}$Zr]Random-DFO-Anti-MUC5AC Humanized Antibody After completion of the PET-CT imaging at 158 hr in Example 17, the mice were euthanized by exsanguination under isoflurane anesthesia. Tumor, blood, and normal organs (including the rest of the body) were collected and weighed. Furthermore, using a γ-ray well scintillation measuring apparatus (JDC-1712, Hitachi Aloka Medical, Ltd.), the radioactivity amount of each organ was measured. The radioactivity accumulation rate (% ID) with respect to the dose was calculated from the radioactivity amount (count) of each organ (including excreted feces and excreted urine), and the amount of accumulated radioactivity (% ID/g) was calculated as the rate of radioactivity accumulation per organ weight.

The evaluation results of biodistribution after completion of the PET-CT imaging are shown in Table 28. The radioactivity distribution rate of tumor at 158 hr after administration was 5.1±2.3% ID, and the radioactivity distribution rate per unit weight was 49.5±5.2% ID. High radioactivity distribution in the liver was confirmed, and the radioactivity distribution rate in the liver was 5.1% ID, and the radioactivity distribution rate per unit weight was 10.4% ID/g. Normal organs with high radioactivity distribution rate except for tumor were liver, kidney, and lung in this order.

TABLE 28

|  | radioactivity distribution rate (% ID) | radioactivity distribution rate per unit weight (% ID/g) |
| --- | --- | --- |
| blood | 4.30 | 5.25 |
| heart | 0.41 | 3.68 |
| lung | 1.01 | 7.76 |
| spleen | 0.64 | 14.68 |
| pancreas | 0.13 | 0.90 |
| liver | 12.86 | 10.40 |
| kidney | 1.47 | 4.06 |
| tumor | 5.06 | 49.52 |
| rest of the body | 29.17 | 6.23 |
| excreted substance | 44.21 | — |

While the present invention has been described above with reference to the embodiments, the present invention is not limited to the above-mentioned embodiments. Various changes that can be understood by those skilled in the art can be made to the constitution and details of the present invention within the scope of the present invention.

The contents disclosed in any publication cited herein, including patents and patent applications, are hereby incorporated in their entireties by reference, to the extent that they have been disclosed herein.

The RI-labeled anti-MUC5AC humanized antibody of the present invention is superior in specificity and accumulation in tumor. Therefore, it is extremely useful for the treatment and/or diagnosis of diseases in which MUC5AC is overexpressed, particularly cancer.

The invention claimed is:
1. A conjugate of an antibody and a chelating agent chelated with a radionuclide,
wherein the radionuclide is Zr-89;
wherein the antibody is a humanized antibody specifically binding to MUC5AC, which having a heavy chain variable region consisting of
(1) the amino acid sequence shown in SEQ ID NO: 1 (H01)
(2) the amino acid sequence shown in SEQ ID NO: 2 (H02)
(3) the amino acid sequence shown in SEQ ID NO: 3 (H03) or
(4) the amino acid sequence shown in SKI ID NO: 4 (H04) and a light chain variable region consisting of
(5) the amino acid sequence shown in SEQ ID NO: 5 (L01),
(6) the amino acid sequence shown in SEQ ID NO: 6 (L02),
(7) the amino acid sequence shown in SEQ ID NO: 7 (L03) or
(8) the amino acid sequence shown in SEQ ID NO: 8 (L04);
wherein the chelating agent site-specifically modifies an Fc region of the antibody via a linker;
wherein the linker comprises a peptide consisting of not less than 13 and not more than 17 amino acid residues, is formed by a crosslinking reaction between the peptide modified with a crosslinking agent and the antibody, and is represented by the following formula (i);

(Xa)-Xaa1-(Xb)-Xaa2-(Xc)-Xaa3-(Xd)　　(i)

wherein Xa, Xb, Xc and Xd are each continuous X in the number of a, continuous X in the number of b, continuous X in the number of c, and continuous X in the number of d, respectively,
X is an amino acid residue having neither a thiol group nor a haloacetyl group in the side chain,
a, b, c and d are each independently an integer of not less than one and not more than 5, and satisfy a+b+c+d≤14,
Xaa1 and Xaa3 are each independently an amino acid residue derived from an amino acid having a thiol group in the side chain, or
one is an amino acid residue derived from an amino acid having a thiol group in the side chain and the other is an amino add residue derived from an amino acid having a haloacetyl group in the side chain, and Xaa1 and Xaa3 are linked, and
Xaa2 is a lysine residue, arginine residue, cysteine residue, aspartic acid residue, glutamic acid residue, 2-aminosuberic acid, or diamino propionic acid, and modified with the crosslinking agent; and
wherein the chelating agent has a structure derived from a compound represented by the following formula (A) or a salt thereof:

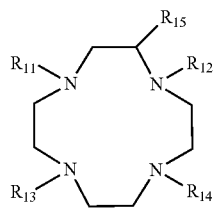

(A)

wherein in the formula (A), $R_{11}$, $R_{13}$ and $R_{14}$ are each independently a group consisting of —$(CH_2)_p$COOH, —$(CH_2)_p C_5 H_5 N$, —$(CH_2)_p PO_3 H_2$, —$(CH_2)_p CONH_2$ or —(CHCOOH)$(CH_2)_p$COOH, one of $R_{12}$ and $R_{15}$ is a hydrogen atom, a carboxyl group, or a carboxyalkyl group having 2 or 3 carbon atoms, the other is a substituent for conjugating with the aforementioned antibody, p is an integer of not less than 0 and not more than 3, $R_{15}$ is a hydrogen atom when $R_{12}$ is a substituent for conjugating with the aforementioned antibody, and $R_{15}$ is a substituent for conjugating with the aforementioned antibody when $R_{12}$ is not a substituent for conjugating with the aforementioned antibody.

2. The conjugate according to claim 1, wherein the antibody is a humanized antibody having
(1) a heavy chain variable region consisting, of the amino acid sequence shown in SEQ ID NO:1 (H01), and
(7) a light chain variable region consisting of the amino acid sequence shown in SEQ ID NO: 7 (L03).

3. The conjugate according to claim 1, wherein the peptide has any one of the following amino acid sequences;

(SEQ ID NO: 9)
(1) DCAYH(Xaa2)GELVWCT, (SEQ ID NO: 10)
(2) GPDCAYH(Xaa2)GELVWCTFH, (SEQ ID NO: 11)
(3) RCAYH(Xaa2)GELVWCS, (SEQ ID NO: 12)
(4) GPRCAYH(Xaa2)GELVWCSFH, (SEQ ID NO: 13)
(5) SPDCAYH(Xaa2)GELVWCTFH, (SEQ ID NO: 14)
(6) GDDCAYH(Xaa2)GELVWCTFH, (SEQ ID NO: 15)
(7) GPSCAYH(Xaa2)GELVWCTFH, (SEQ ID NO: 16)
(8) GPDCAYH(Xaa2)GELVWCSFH, (SEQ ID NO: 17)
(9) GPDCAYH(Xaa2)GELVWCTHH, (SEQ ID NO: 18)
(10) GPDCAYH(Xaa2)GELVWCTFY, (SEQ ID NO: 19)
(11) SPDCAYH(Xaa2)GELVWCTFY, (SEQ ID NO: 20)
(12) SDDCAYH(Xaa2)GELVWCTFY
and (SEQ ID NO: 21)
(13) RGNCAYH(Xaa2)GQLVWCTYH, wherein Xaa2 is a lysine residue.

4. The conjugate according to claim 3, wherein the peptide has any one of the following amino acid sequences;

(SEQ ID NO: 10)
(2) GPDCAYH(Xaa2)GELVWCTFH, (SEQ ID NO: 16)
(8) GPDCAYH(Xaa2)GELVWCSFH,

```
                                            (SEQ ID NO: 17)
(9)  GPDCAYH(Xaa2)GELVWCTHH
and (SEQ ID NO: 18)
(10) GPDCAYH(Xaa2)GELVWCTFY,
``` wherein Xaa2 is a lysine residue.

5. The conjugate according to claim 1, in the formula in the formula (A), $R_{11}$, $R_{13}$ and $R_{14}$ are each independently a group consisting of —$(CH_2)_p$COOH, or —(CHCOOH)$(CH_2)_p$COOH, p is 1 $R_{12}$ and is a substituent for conjugating with the antibody and $R_{15}$ is a hydrogen atom.

6. The conjugate according to claim 5, wherein a linkage site between the chelate site and the substituent for conjugating with the antibody comprises an amide bond or a thiourea bond, and the linkage site is derived from the amide bond formed by the reaction of an N-hydroxysuccinimidoester (NHS) group, or a 2,6-dioxo tetrahydro-2H-pyranyl group with primary amine, or thiourea bond formed by the reaction of an isothiocyanate group with primary amine or a maleimide group.

7. The conjugate according to claim 1, wherein the chelating agent has a structure derived from a compound represented by the following formula (A-9) or a salt thereof:

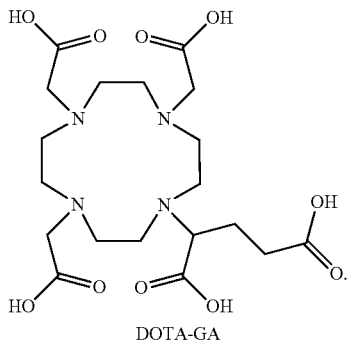

(A-9)

DOTA-GA

8. The conjugate according to claim 1, wherein the linker has a chelate linker connecting to a chelating agent, a first atomic group connecting to the linker, a second atomic group that can perform click reaction with the first atomic group, and an antibody-modification linker connecting to the second atomic group, which includes the antibody-modification peptide, and
wherein the linker has a chemical structure represented by the following formula (10a), (10b) or (10c) as a chemical structure derived from the first atomic group and the second atomic group:

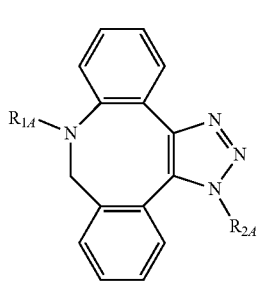

(10a)

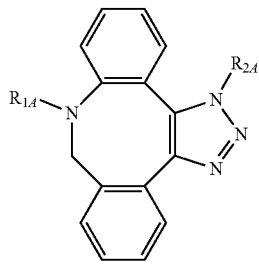

(10b)

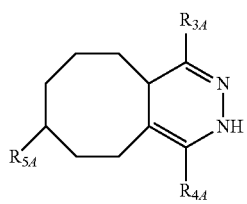

(10c)

wherein in the formula (10a) and the formula (10b), $R_{1A}$, is a binding site with a chelate linker, and $R_{2A}$ is a binding site with an antibody-modification linker, and wherein in the formula (10c), one of $R_{3A}$ and $R_{4A}$ is a hydrogen atom, a methyl group, a phenyl group or a pyridyl group, and the other is a binding site with a chelate linker, and $R_{5A}$ is a binding site with an antibody-modification linker.

9. The conjugate according to claim 1,
wherein the antibody is a humanized antibody having
(1) a heavy chain variable region consisting of the amino acid sequence shown in SEQ ID NO: 1 (H01), and
(7) a light chain variable region consisting of the amino acid sequence shown in SEQ ID NO: 7 (L03);
wherein the peptide has the following amino acid sequence,
2) GPDCAYH(Xaa2)GELVWCTFH (SEQ ID NO: 10),
wherein Xaa2 is a lysine residue;
wherein the chelating agent has a structure derived from a compound represented by the following formula (A-9) or a salt thereof:

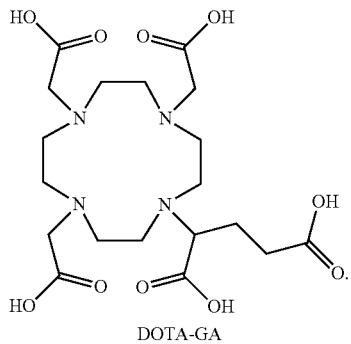

(A-9)

DOTA-GA

10. The conjugate according to claim 1,
wherein the antibody is a humanized antibody having
(1) a heavy chain variable region consisting of the amino acid sequence shown in SEQ ID NO: 1 (H01), and
(7) a light chain variable region consisting of the amino acid sequence shown in SEQ ID NO: 7 (L03);
wherein the peptide has the following amino acid sequence, (8) GPDCAYH(Xaa2)GELVWCSFH (SEQ ID NO: 16),
wherein Xaa2 is a lysine residue;
wherein the chelating agent has a structure derived from a compound represented by the following formula (A-9) or a salt thereof:

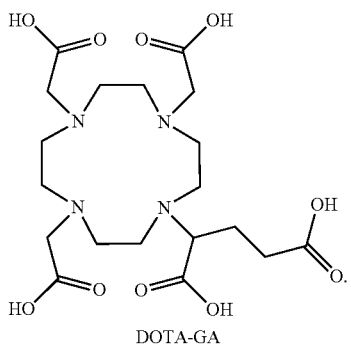
DOTA-GA

11. The conjugate according to claim 1,
wherein the antibody is a humanized antibody having
(1) a heavy chain variable region consisting of the amino acid sequence shown in SEC ID NO: 1 (H01), and
(7) a light chain variable region consisting of the amino acid sequence shown in SEQ ID NO: 7 (L03);
wherein the peptide has the following amino acid sequence,
(9) GPDCAYH(Xaa2)GELVWCSFH (SEQ ID NO: 17),
wherein Xaa2 is a lysine residue;
wherein the chelating agent has a structure derived from a compound represented by the following formula (A-9) or a salt thereof:

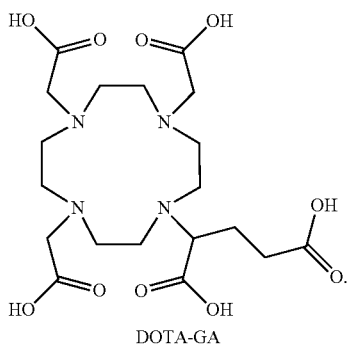
DOTA-GA

12. The conjugate according to claim 1,
wherein the antibody is a humanized antibody having
(I) a heavy chain variable region consisting of the amino acid sequence shown in SEQ ID NO: 1 (H01), and
(7) a light chain variable region consisting of the amino acid sequence shown in SEQ ID NO: 7 (L03);
wherein the peptide has the following amino acid sequence,
(10) GPDCAYH(Xaa2)GELVWCSFH (SEQ ID NO: 1$),
wherein Xaa2 is a lysine residue;
wherein the chelating agent has a structure derived from a compound represented by the following formula (A-9) or a salt thereof:

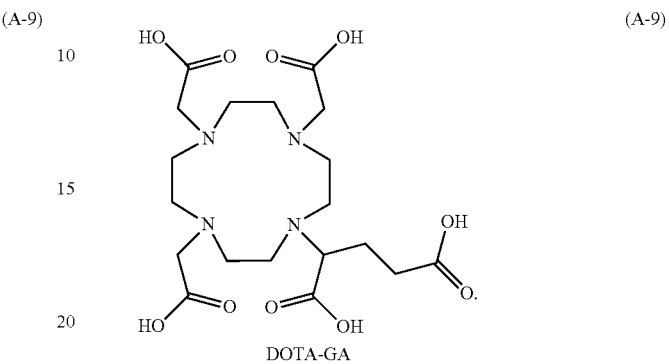
DOTA-GA

13. A method for diagnosing cancer using the conjugate according to claim 1.

14. A kit for producing a conjugate according to claim 1, comprising a chelating agent capable of chelating a radionuclide and an anti-MUC5AC antibody.

15. The kit according to claim 14, further comprising a first atomic group capable of click reaction and a second atomic group capable of click reaction.

16. The kit according to claim 15, wherein the first atomic group capable of click reaction and the second atomic group capable of click reaction comprise any one of alkyne, azide, 1,2,4,5-tetrazine and alkene, respectively.

17. The kit according to claim 14, further comprising a radionuclide capable of chelating with the chelating agent.

18. A modified antibody with an Fc region of the antibody specifically modified by an antibody-modification linker provided with an antibody-modification peptide, wherein the antibody is a humanized antibody specifically binding to MUC5AC, which having a heavy chain variable region consisting of
(1) the amino acid sequence shown in SEQ ID NO: 1 (H01),
(2) the amino acid sequence shown in SEQ ID NO: 2 (H02),
(3) the amino acid sequence shown in SEQ NO: (H03), or
(4) the amino acid sequence shown in SEQ II) NO: 4 (H04), and
a light chain variable region consisting of
(5) the amino acid sequence shown in SEQ ID NO: 5 (L01),
(6) the amino acid sequence shown in SEQ ID NO: 6 (L02),
(7) the amino acid sequence shown in SEQ ID NO: 7 (L03), or
(8) the amino acid sequence shown in SEQ ID NO: 8 (L04); and
wherein the antibody-modification linker has an atomic group to connect to a chelate linker of a chelating agent chelated with a radionuclide by a click reaction.

\* \* \* \* \*

UNITED STATES PATENT AND TRADEMARK OFFICE
CERTIFICATE OF CORRECTION

PATENT NO. : 11,369,701 B2  
APPLICATION NO. : 17/367077  
DATED : June 28, 2022  
INVENTOR(S) : Norihito Nakata et al.

Page 1 of 1

It is certified that error appears in the above-identified patent and that said Letters Patent is hereby corrected as shown below:

In the Claims

Column 89, Line 14, Claim 1, delete "SKI" and insert --SEQ--.

Column 89, Line 46, Claim 1, delete "add" and insert --acid--.

Column 91, Line 8, Claim 5, delete "in the formula".

Column 92, Line 38, Claim 9, delete "2)" and insert --(2)--.

Column 93, Line 57, Claim 12, delete "I" and insert --1--.

Column 94, Line 2, Claim 12, delete "1$)" and insert --18)--.

Column 94, Line 47, Claim 18, delete "SEQ NO:" and insert --SEQ ID NO: 3--.

Column 94, Line 48, Claim 18, delete "SEQ II)" and insert --SEQ ID--.

Signed and Sealed this  
Twenty-sixth Day of August, 2025

Coke Morgan Stewart  
*Acting Director of the United States Patent and Trademark Office*